(12) United States Patent
Ehrenreich et al.

(10) Patent No.: US 9,011,355 B2
(45) Date of Patent: *Apr. 21, 2015

(54) METHODS AND DEVICES FOR TREATING HYPERTENSION

(71) Applicant: Sympara Medical, Inc., San Francisco, CA (US)

(72) Inventors: Kevin Joe Ehrenreich, San Francisco, CA (US); Randolf von Oepen, Aptos, CA (US); Kelly Justin McCrystle, Menlo Park, CA (US)

(73) Assignee: Sympara Medical, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/266,410

(22) Filed: Apr. 30, 2014

(65) Prior Publication Data

US 2014/0236057 A1    Aug. 21, 2014

Related U.S. Application Data

(63) Continuation of application No. 13/973,834, filed on Aug. 22, 2013, now Pat. No. 8,740,825, which is a continuation of application No. 13/656,344, filed on Oct. 19, 2012.

(Continued)

(51) Int. Cl.
*A61H 1/00* (2006.01)
*A61H 23/00* (2006.01)
(Continued)

(52) U.S. Cl.
CPC .................. *A61H 23/00* (2013.01); *A61H 1/00* (2013.01); *A61H 2201/5028* (2013.01);
(Continued)

(58) Field of Classification Search
CPC ......... A61H 1/00; A61H 23/00; A61H 23/02; A61H 23/0236; A61H 23/0245
USPC ........... 601/15–18, 39, 46, 67–71, 78, 79, 81, 601/84, DIG. 11; 607/14, 15; 381/151
See application file for complete search history.

(56) References Cited

U.S. PATENT DOCUMENTS 3,085,568 A   4/1963   Whitesell
3,650,277 A   3/1972   Sjostrand et al.
(Continued)

FOREIGN PATENT DOCUMENTS

EP   2130525 A1   12/2009
EP   1569722 B1   4/2013
WO   WO 2010/003223   1/2010

OTHER PUBLICATIONS

Abraham, William T.; Barostim Therapy (presentation); Ohio State Univ.; Columbus, OH; 11 pgs.; http://www.cvrx.com/wp-contentluploads/2013/05/Dr.-Abraham-Slides.pdf; (this web address was available to applicant(s) at least as of May 2013).

(Continued)

*Primary Examiner* — Valerie L Skorupa
(74) *Attorney, Agent, or Firm* — Knobbe, Martens, Olson & Bear, LLP

(57) ABSTRACT

Devices, systems and methods are described which control blood pressure and nervous system activity by stimulating baroreceptors. By selectively and controllably activating baroreceptors and/or nerves, the present invention reduces blood pressure and alters the sympathetic nervous system; thereby minimizing deleterious effects on the heart, vasculature and other organs and tissues. A baroreceptor activation device or other sensory activation device is positioned near a dermal bone to provide the treatment.

20 Claims, 17 Drawing Sheets

Related U.S. Application Data

(60) Provisional application No. 61/549,007, filed on Oct. 19, 2011, provisional application No. 61/648,060, filed on May 16, 2012, provisional application No. 61/681,469, filed on Aug. 9, 2012, provisional application No. 61/681,513, filed on Aug. 9, 2012.

(51) Int. Cl.
*A61H 23/02* (2006.01)
*A61H 23/04* (2006.01)

(52) U.S. Cl.
CPC ............... A61H 2201/0196 (2013.01); *A61H 2201/1614* (2013.01); *A61H 23/0236* (2013.01); *A61H 23/0245* (2013.01); *A61H 23/04* (2013.01); A61H 2201/0207 (2013.01); A61H 2201/1609 (2013.01); A61H 2201/165 (2013.01); A61H 2201/5007 (2013.01); A61H 2201/5015 (2013.01); A61H 2201/5035 (2013.01); A61H 2201/5038 (2013.01); A61H 2201/5041 (2013.01); A61H 2201/5043 (2013.01); A61H 2201/5058 (2013.01); A61H 2201/5084 (2013.01); A61H 2201/5092 (2013.01); A61H 2201/5097 (2013.01); A61H 2230/045 (2013.01); A61H 2230/065 (2013.01); A61H 2230/208 (2013.01); A61H 2230/305 (2013.01); A61H 2230/505 (2013.01); A61H 2230/705 (2013.01); A61H 2023/002 (2013.01)

(56) References Cited

U.S. PATENT DOCUMENTS

| | | | |
|---|---|---|---|
| 3,664,331 A | 5/1972 | Filipovici |
| 3,880,152 A | 4/1975 | Nohmura |
| 4,023,566 A | 5/1977 | Martinmaas |
| 4,064,376 A | 12/1977 | Yamada |
| 4,343,303 A | 8/1982 | Williams |
| 4,495,638 A | 1/1985 | Yamada et al. |
| 4,674,482 A | 6/1987 | Waltonen et al. |
| 4,697,580 A | 10/1987 | Terauchi |
| 4,750,208 A | 6/1988 | Yamada et al. |
| 4,753,225 A | 6/1988 | Vogel |
| 4,895,149 A | 1/1990 | Morez |
| 5,012,816 A | 5/1991 | Lederer |
| 5,036,858 A | 8/1991 | Carter et al. |
| 5,076,260 A | 12/1991 | Komatsu |
| 5,113,852 A | 5/1992 | Murtonen |
| 5,125,033 A | 6/1992 | Lee |
| 5,132,942 A | 7/1992 | Cassone |
| 5,261,422 A | 11/1993 | Kelly |
| 5,442,710 A | 8/1995 | Komatsu |
| 5,727,558 A | 3/1998 | Hakki et al. |
| 5,879,314 A | 3/1999 | Peterson et al. |
| 5,891,181 A | 4/1999 | Zhu |
| 5,895,348 A | 4/1999 | Hosaka |
| 6,050,952 A | 4/2000 | Hakki et al. |
| 6,053,879 A | 4/2000 | Leban et al. |
| 6,178,352 B1 | 1/2001 | Gruzdowich et al. |
| 6,256,397 B1 | 7/2001 | Komatsu |
| 6,369,312 B1 | 4/2002 | Komatsu |
| 6,424,864 B1 | 7/2002 | Matsuura |
| 6,500,134 B1 | 12/2002 | Cassone |
| 6,522,926 B1 | 2/2003 | Kieval et al. |
| 6,537,234 B1 | 3/2003 | Komatsu |
| 6,544,165 B1 | 4/2003 | McNew |
| 6,545,384 B1 | 4/2003 | Pelrine et al. |
| 6,620,117 B1 | 9/2003 | Johnson et al. |
| 6,633,779 B1 | 10/2003 | Schuler et al. |
| 6,681,136 B2 | 1/2004 | Schuler et al. |
| 6,735,480 B2 | 5/2004 | Giuntoli et al. |
| 6,751,501 B1 | 6/2004 | Schuler et al. |
| 6,775,573 B2 | 8/2004 | Schuler et al. |
| 6,814,709 B2 | 11/2004 | Schwartz et al. |
| 6,819,771 B2 | 11/2004 | Menzies |
| 6,850,801 B2 | 2/2005 | Kieval et al. |
| 6,892,428 B2 | 5/2005 | Reiter |
| 6,957,106 B2 | 10/2005 | Schuler et al. |
| 7,011,638 B2 | 3/2006 | Schuler et al. |
| 7,058,446 B2 | 6/2006 | Schuler et al. |
| 7,062,324 B2 | 6/2006 | Schuler et al. |
| 7,077,815 B1 | 7/2006 | Cassone |
| 7,141,028 B2 | 11/2006 | McNew |
| 7,166,070 B2 | 1/2007 | Lawlis et al. |
| 7,211,060 B1 | 5/2007 | Talish et |
| 7,261,693 B2 | 8/2007 | Wilcox et al. |
| 7,273,458 B2 | 9/2007 | Prausnitz et al. |
| 7,300,409 B2 | 11/2007 | Kopanic et al. |
| 7,407,488 B2 | 8/2008 | Cassone |
| 7,452,335 B2 | 11/2008 | Wells et al. |
| 7,499,747 B2 | 3/2009 | Kieval et al. |
| 7,517,328 B2 * | 4/2009 | Hoffmann ............. 601/46 |
| 7,571,002 B2 | 8/2009 | Thrope et al. |
| 7,608,989 B2 | 10/2009 | Heydt et al. |
| 7,654,949 B2 | 2/2010 | McNew |
| 7,681,578 B2 | 3/2010 | Nashwan |
| 7,713,295 B2 | 5/2010 | Ahn et al. |
| 7,749,171 B2 | 7/2010 | Gozani et al. |
| 7,846,084 B2 | 12/2010 | McNew |
| 7,909,785 B2 | 3/2011 | Podrazhansky et al. |
| 7,917,201 B2 | 3/2011 | Gozani et al. |
| 7,990,022 B2 | 8/2011 | Heim |
| 8,060,206 B2 | 11/2011 | Kieval et al. |
| 8,079,968 B2 * | 12/2011 | Hoffmann ............. 601/46 |
| 8,113,517 B2 | 2/2012 | Canterbury et al. |
| 8,139,803 B2 * | 3/2012 | Afshar ............. 381/333 |
| 8,140,170 B2 | 3/2012 | Rezai et al. |
| 8,175,712 B2 | 5/2012 | Tang et al. |
| 8,233,988 B2 | 7/2012 | Errico et al. |
| 8,337,432 B2 | 12/2012 | Nashwan |
| 8,442,632 B2 | 5/2013 | Kullok et al. |
| 8,478,414 B2 | 7/2013 | Kieval et al. |
| 8,788,041 B2 | 7/2014 | Yun et al. |
| 2002/0091339 A1 | 7/2002 | Horzewski et al. |
| 2003/0067197 A1 | 4/2003 | Komatsu |
| 2004/0010303 A1 | 1/2004 | Bolea et al. |
| 2004/0019364 A1 | 1/2004 | Kieval et al. |
| 2004/0167446 A1 | 8/2004 | Podrazhansky et al. |
| 2004/0173220 A1 | 9/2004 | Harry et al. |
| 2004/0230252 A1 | 11/2004 | Kullok et al. |
| 2004/0254616 A1 | 12/2004 | Rossing et al. |
| 2005/0054958 A1 * | 3/2005 | Hoffmann ............. 601/46 |
| 2005/0085879 A1 | 4/2005 | Ahn et al. |
| 2005/0087194 A1 | 4/2005 | Scott |
| 2005/0148906 A1 | 7/2005 | Skover et al. |
| 2005/0249667 A1 | 11/2005 | Tuszynski et al. |
| 2005/0251212 A1 | 11/2005 | Kieval et al. |
| 2005/0267388 A1 | 12/2005 | Hanna |
| 2006/0047229 A1 | 3/2006 | Dussaussoy |
| 2006/0113879 A1 | 6/2006 | Ren et al. |
| 2006/0119225 A1 | 6/2006 | Heim et al. |
| 2006/0211955 A1 | 9/2006 | Horzewski et al. |
| 2006/0258962 A1 | 11/2006 | Kopanic et al. |
| 2007/0021797 A1 | 1/2007 | Kieval et al. |
| 2007/0038164 A1 | 2/2007 | Afshar |
| 2007/0093732 A1 | 4/2007 | Venturi et al. |
| 2007/0142879 A1 | 6/2007 | Greenberg et al. |
| 2007/0178771 A1 | 8/2007 | Goetz et al. |
| 2007/0213645 A1 | 9/2007 | Zumeris et al. |
| 2007/0232191 A1 | 10/2007 | Smith et al. |
| 2007/0232962 A1 | 10/2007 | Zumeris et al. |
| 2008/0039749 A1 | 2/2008 | Kopanic, Jr. et al. |
| 2008/0065167 A1 | 3/2008 | Boggs, II et al. |
| 2008/0086187 A1 | 4/2008 | Baxter et al. |
| 2008/0167696 A1 | 7/2008 | Cates et al. |
| 2008/0177364 A1 | 7/2008 | Bolea et al. |
| 2008/0195007 A1 | 8/2008 | Podrazhansky et al. |
| 2008/0214968 A1 | 9/2008 | Milne et al. |
| 2008/0219468 A1 | 9/2008 | Williams et al. |
| 2008/0275343 A1 | 11/2008 | Hoffmann |
| 2008/0287793 A1 * | 11/2008 | Hoffmann ............. 600/439 |
| 2008/0288035 A1 | 11/2008 | Gill et al. |

(56) References Cited

U.S. PATENT DOCUMENTS

| | | | |
|---|---|---|---|
| 2009/0005713 | A1 | 1/2009 | Podrazhansky et al. |
| 2009/0006713 | A1 | 1/2009 | Royer et al. |
| 2009/0069728 | A1 | 3/2009 | Hoffmann et al. |
| 2009/0076421 | A1 | 3/2009 | Grant |
| 2009/0200501 | A1 | 8/2009 | Heim et al. |
| 2009/0270773 | A1 | 10/2009 | Hoffmann |
| 2010/0106156 | A1 | 4/2010 | Laufer et al. |
| 2010/0217295 | A1 | 8/2010 | Forsell |
| 2010/0222723 | A1 | 9/2010 | Hoffmann |
| 2010/0256436 | A1 | 10/2010 | Partsch et al. |
| 2010/0260371 | A1 | 10/2010 | Afshar |
| 2010/0292527 | A1 | 11/2010 | Schneider et al. |
| 2011/0046432 | A1* | 2/2011 | Simon et al. .......... 600/14 |
| 2011/0125204 | A1 | 5/2011 | Louise |
| 2011/0196271 | A1 | 8/2011 | Forsell |
| 2011/0301662 | A1 | 12/2011 | Bar-Yoseph et al. |
| 2012/0035513 | A1* | 2/2012 | Afshar .......... 601/46 |
| 2012/0253236 | A1 | 10/2012 | Snow et al. |
| 2013/0072834 | A1 | 3/2013 | Afshar |
| 2013/0102937 | A1 | 4/2013 | Ehrenreich et al. |
| 2013/0281897 | A1 | 10/2013 | Hoffmann et al. |
| 2013/0345606 | A1 | 12/2013 | Ehrenreich et al. |
| 2013/0345608 | A1 | 12/2013 | Ehrenreich et al. |
| 2014/0107542 | A1 | 4/2014 | Schubert et al. |
| 2014/0148872 | A1 | 5/2014 | Goldwasser et al. |
| 2014/0163439 | A1 | 6/2014 | Hoffmann et al. |
| 2014/0180181 | A1 | 6/2014 | von Oepen et al. |
| 2014/0207219 | A1 | 7/2014 | Dunbar et al. |
| 2014/0228721 | A1 | 8/2014 | Ehrenreich et al. |
| 2014/0288472 | A1 | 9/2014 | Ehrenreich et al. |

OTHER PUBLICATIONS

Aftershokz (Lee, Nicole); AfterShokz to debut 'world's first' bone-conducting Bluez headphones at CES 2013 (press release), 3 pgs.; Dec. 22, 2012.

Alfrey, Karen D., Characterizing the Afferent Limb of the Baroreflex, Thesis Submitted in Partial Fulfillment of the Requirements for the Degree, Rice University, Houston Texas; pp. 1-177; Apr. 2000.

Amatoury et al.; Snoring-related energy transmission to the carotid artery in rabbits; J Appl Physiol; 100; pp. 1547-1553; Feb. 2006.

Annunziata et al.; Fetal vibroacoustic stimulation in computerized cardiotocographic analysis: The role of short-term varibility and approximate entropy; Journal of Pregnancy; vol. 2012; ID 814987; 7 pgs.; 2012 (Accepted for publn. Oct. 12, 2011).

Arabin, S.; Opinion: Music during pregnancy; Ultrasound Obstet Gynecol; 20 (5); pp. 425-430; Nov. 2002.

Arasteh et al.; The effects of carotid baroreceptor stimulation on blood pressure variability in young male athletes and non-athletes; African Journal of Pharmacy and Pharmacology; 5(6); pp. 737-741; Jun. 2011.

Bakris, George; Barostim Therapy (presentation); Univ. of Chicago Medicine; Chicago, IL; 9 pgs.; http://www.cvrx.com/wp-contentluploads/2013/05/Dr.-Bakris-Slides.pdf; (this web address was available to applicant(s) at least as of May 2013).

Beglyarov et al.; Vibroacoustic impact in the Treatment of Arterial Hypertension; 2 pgs.; printed Sep. 23, 2013 from http://web-archive-net.com/page/303146/20 12-09-17/http://www.lowfreqsoundresearch.net/forum/topic/vibroacoustic-impact-in-the-treatment-of-arterial-hypertension.

Bellman, Michael; Perception of whole-body vibrations: from basic experiments to effects of seat and steering-wheel vibrations on the passenger's comfort inside vehicles (dissertation); University of Oldenburg; 209 pgs.; Nov. 1972.

Bergström-Isacsson, Märith; Music and vibroacoustic stimulation in people with Rett Syndrome—A Neurophysiological Study (Thesis); Alborg Univ., DK; 199 pgs.; 2011; http://www.aau.dkldigitalAssets/29/29534_english-summary.pdf (This web address was available to applicant(s) at least as of Jul. 11, 2012).

Bernardi et al.; Cardiovascular autonomic modulation and activity of carotid baroreceptors at altitude; Clinical Science; 95(5); pp. 565-573; Nov. 1998.

Bernardi et al.; Dynamic interactions between musical, cardiovascular, and cerbral rhythms in humans; Circulation; 119; pp. 3171-3180; Jun. 2009.

Bertog et al; Renal denervation for hypertension; J. Am. Coll. Cardiol. Intv.; 5(3); pp. 249-258; Mar. 2012.

Bisognano et al.; Results from the Rheos Pivotal Trial (presentation); 19 pgs.; www.cardiosource.orgHmedia/Files/.../ACC11_RHEOS_PIVOTAL.ashx?; this web address was available to applicant(s) at least as of Aug. 2013).

Blankenship, Tim; Tactile feedback solutions using piezoelectric actuators; Maxim Integrated Products; 11 pgs.; Jan. 17, 2011.

Bobrie, G.; Device-based antihypertensive therapy; 56 pgs.; 2011; HEGP; Paris, FR; printed Aug. 19, 2013 (http://www.soc-nephrologie.org/PDF/epro/formation/FMC/2011/bobrie.pdf).

Bosch et al.; The management of portal hypertension: rational basis, available treatments and future option; Journal of hepatology; 48(suppl. 1); pp. S68-S92; Feb. 2008.

Bourgalt et al.; Persistence and discontinuation patterns of antihypertensive therapy among newly treated patients: a population-based study; Journal of Human Hypertension; 19(8); pp. 607-613; Aug. 2005.

Boyd, J. D.; The carotid sinus mechanism; Ulter Med J; 3(1); pp. 14, 17-20; Jan. 1934.

Bradt et al.; Music for stress and anxiety reduction in coronary heart disease patients (review); Cochrane Database Syst Rev; Issue 2; 77 pgs.; Apr. 2009.

Brandão Rondon et al.; Postexercise blood pressure reduction in elderly hypertensive patients; J. Am. Coll. Cardiol.; 39(4); pp. 676-682; Feb. 2002.

Brandes et al.; The effect of receptive music therapy on heart rate variability in hypertensive patients; 1 pge.; project No. 7111; http://www.musik-medizin.atJBrandes%20et.al. %20APS%200308.pdf (This web address was available to applicant(s) at least as of Mar. 29, 2012).

Braunwald, Eugene; Introduction to Symposium (presentation); 11 pgs.; Aug. 30, 2011; http://www.cvrx.com/wp-contentJuploads/2013/05/Braunwald_Slides_Final.pdf; (this web address was available to applicant(s) at least as of May 2013).

Brown et al., The Relative Sensitivity to Vibration of Muscle Receptors of the Cat, J Physiol, 192(3), pp. 773-800; Oct. 1967.

Calhoun et al.; Resistant hypertension: Diagnosis, evaluation, and treatment: A scientific statement from the american heart association professional education committee of the council for high blood pressure research; Circulation; 117; e510-e526; Jun. 2008.

Cardinale et al.; The use of vibration as an exercise intervention; Exerc. Sport Sci. Rev.; 31 (1); pp. 3-7; Jan. 2003.

Cartner, Benjamin W.; Effects of aerobic exercise on nocturnal blood pressure dipping in prehypertensive individuals (thesis); Appalachian State University; pp. 1-28; Dec. 2011.

CBC News; Scientists Say Nerves use Sound, not Electricity, 1 pg.; Mar. 9, 2007; printed Jun. 13, 2013; www .cbc.ca/news/technology/story/2007/03/09/science-nervessound-20070309. html.

Chapleau et al.; Contrasting effects of static and pulsatile pressure on carotid baroreceptor activity in dogs; Circ res; 61 (5); pp. 648-658; Nov. 1987.

Chapman et al.; Effect of spironalactone on blood pressure in subjects with resistant hypertension; Hypertension; 49; pp. 839-845; Apr. 2007.

Chapter 14: The Cutaneous Senses; presentation/lecture slides; 41 slides; Aug. 1984 (downloaded from http://www.radford.edu).

Cho et al.; Tissue vibration induces carotid artery endothelial dysfunction: A mechanism linking snoring and carotid atherosclerosis?; Sleep; 34(6); pp. 751-757; Jun. 2011.

Chobanian el al.(committee); The seventh report of the joint national committee on prevention, detection, evaluation, and treatment of high blood pressure (JNC 7); Hypertension; 42; pp. 1206-1252; Dec. 2003.

Cochrane, 0.; The potential neural mechanisms of acute indirect vibration; Journal of Sports Science and Medicine; 10; pp. 19-30; Mar. 2011.

Cooper et al.; Carotid baroreceptor reflexes in humans during orthostatic stress; Experimental Physiology; 86(5); pp. 677-681; Sep. 2001.

(56) References Cited

OTHER PUBLICATIONS

Cooper et al.; Carotid baroreflex testing using the neck collar device; Clin Auton Res; 19(2); pp. 102-112; Apr. 2009.

Costa et al.; Microneurographic evidence of sudden sympathetic withdrawal in carotid sinus syncope; treatment with ergotamine; Chest; 106(2); pp. 617-620; Aug. 1994.

CVRx; First generation BAT results in resistant hypertension; 22 pgs.; http://www.29984.com/htm1/12_SwCPowerPoint_Presentation_CVRx_8419.html; this web address was available to applicant(s) at least as of Aug. 2013).

Daugherty et al.; Incidence and prognosis of resistant hypertension in hypertensive patients; Circulation; 125; pp. 1635-1642; Apr. 2012.

DeLeeue, Peter; Barostim neo} System (presentation); 16 pgs.; http://www.cvrx.com/wp-contentluploads/2013/05/Dr.-de-Leeuw-Slides.pdf; (this web address was available to applicant(s) at least as of May 2013).

DiBona et al.; Chaotic behavior of renal sympathetic nerve activity: effect of baroreceptor denervation and cardiac failure; Am J Physiol Renal Physiol; 279(3); pp. F491-F501; Sep. 2000.

Dirix et al.; Aspects of fetal learning and memory; Child Development; 80 (4); pp. 1251-1258; Jul./Aug. 2009.

Donadio et al.; Inhibition of human muscle sympathetic activity by sensory stimulation; J. Physiol.; 544.1; pp. 285-292; Oct. 2002.

Drew, Rachel; The effects of muscle mechanoreflex stimulation via passive muscle stretch on baroreflex function in humans (thesis); Univ. of Birmingham; 141 pgs.; Apr. 2008.

Ead et al.; A comparison of the effects of pulsatile and non-pulsatile blood flow through the carotid sinus on the reflexogenic activity of the sinus baroceptors in the cat; J Physiol; 118(4); pp. 509-519; Dec. 1952.

Egizio, Victoria, The Effects of Baroreceptors Stimulation on Short-Term Verbal Memory, University of Pittsburg thesis presentation, pp. i-ix & 1-76; Sep. 9, 2008.

Egloff et al., A Vibrotactile Music System Based on Sensory Substitution (w/ associated paper), Journal Acoust. Soc. Am., vol. 129, No. 4, Pt. 2, abstract No. 4aMU10, p. 2582 (Apr. 2011).

Ekenvall et al.; Is vibration white finger a primary sympathetic nerve injury?; British Journal of Medicine; 43(10); pp. 702-706; Oct. 1986.

Elbert et al., What Goes Up (from heart to brain) must calm down (from brain to heart)! From the Heart to the Brain/ Dieter Vaitl . . . (eds.). Frankfurt am Main; Lang, pp. 133-149, 1995 (year of pub. sufficiently earlier than effective US filing date and any foreign priority date).

Ellis et al.; Music and autonomic nervous system (dys)function; Music Percept.; 27(4); pp. 317-326; Apr. 2010 (14 pgs. / author manuscript).

Emotional Sound Techniques; Vibroacoustic Therapy Systems & Soundpads (product information); 10 pgs.; printed Aug. 15, 2013 from webpage (http://emotionalsoundtechniques.com/producllchair-back-sound-pad-vts-1000-vibroacoustic-therapysystem/).

Esler et al.; Renal sympathetic denervation for treatment of resistant hypertension: one-year results from the symplicity HTN-2 randomized controlled trial; Circulation; 126; pp. 2976-2982; Dec. 2012.

Fadel et al.; Recent insights into carotid baroreflex function in humans using the variable pressure neck chamber; Experimental Physiology; 88(6); pp. 671-680; Nov. 2003.

Fadel, Paul; Arterial baroreflex control of the peripheral vasculature in humans: rest and exercise; Med Sci Sports Exerc; 40(12); pp. 2055-2062; Dec. 2008.

Farrar et al.; Evolution of peripheral nerve function in humans: novel insights from motor nerve excitability; The Journal of Physiology; 591(Pt 1); pp. 273-286; Jan. 1, 2013 (Epub Sep. 24, 2012).

Fisher et al.; Carotid baroreflex control of arterial blood pressure at rest and during dynamic exercise in aging humans; Am J Physiol Regul Integr Comp Physiol; 299(5); pp. R1241-R1247; Nov. 2010.

Gandevia et al.; Motoneuronal output and gradation of *effort* in attempts to contract acutely paralysed leg muscles in man; J. Physiol.; 471; pp. 411-427; Nov. 1993.

Gassler et al.; The role of baroreflex activation therapy in sympathetic modulation for the treatment of resistant hypertension; Heart; 98(23); pp. 1689-1692; Dec. 2012.

Geisler et al.; Cost-effectiveness and clinical effectiveness of catheter-based renal denervation for resistant hypertension; J Am Coll Cardiol; 60(14); pp. 1271-1277; Oct. 2012.

Geisler, D., A Model of the Peripheral Auditory System Responding to Low-Frequency Tones, Biophysical Journal, 8(1), pp. 1-15; Jan. 1968.

Gernandt et al.; Spinal motor responses to acoustic stimulation (research report); US Naval Aviation Med. Center; Bureau of Med. and Surgery; project MR005. 13-2005, subtask 4, report No. 2, NASA order No. R-93; 15 pgs. Apr. 22, 1964.

Ghetti, Claire; Music therapy as procedural support for invasive medical procedures: toward the development of music therapy theory; Nordic Journal of Music Therapy; 21 (1); pp. 3-35; Feb. 2012.

Gilman, S., Joint Position Sense and Vibration Sense: Anatomical Organisation and Assessment, Journal Neural Neurosurg Psychiatry; 73(5): pp. 473-477, Nov. 2002.

Godlewski, Jacek; Catheter-based treatment for hypertension (presentation); euro PCR; 10 pgs.; http://cardio.nIINAS/Jacek_20100527_1728_room252A.pdf; 2010 (This web address was available to applicant(s) al least as of Oct. 22, 2011).

Golgher, Lior; Synchronous neural oscillations and motor vehicle vibrations (preliminary literature survey); Weizmann Institute of Science—Feinberg Graduate School; 90 pgs.; Jun. 2006.

Goodwin et al.; Cardiovascular and respiratory responses to changes in central command during isometric exercise at contant muscle tension; J. Physiol.; 226(1); pp. 173-190; Oct. 1972.

Grassi et al.; Baroreflex control of sympathetic nerve activity in essential and secondary hypertension; Hypertension; 31(1); pp. 68-72; Jan. 1998.

Grassi et al.; Dissociation between muscle and skin sympathetic nerve activity in essential hypertension, obesity, and congestive heart failure; Hypertension; 31 (1); pp. 64-67; Jan. 1998.

Grassi et al.; Mechanisms responsible for sympathetic activation by cigarette smoking in humans; Circulation; 90; pp. 248-253; Jul. 1994.

Grassi et al.; Muscle and skin sympathetic nerve traffic during the "white-coat" effect; Curculation; 100; pp. 222-225; Jul. 1999.

Greenwood et al.; Single-unit sympathetic discharge: quantitative assessment in human hypertensive disease; Circulation; 100; pp. 1305-1310; Sep. 1999.

Haneke et al. (contributors); Infrasound toxicological summary; National Toxicology Program; No. P266J; pp. 1-51; Nov. 2001.

Hart et al.; Baroreflex control of muscle sympathetic nerve activity: a nonpharmacological measure of baroreflex sensitivity; Am J Physiol Heart Circ Physiol; 298; pp. H816-H822; Mar. 2010.

Hasenfuss. Gerd; New Generation Barostim neo} System (presentation); 23 pgs.; http://www.cvrx.com/pdf/meetings/Hasenfuss_Slides_Final.pdf; (this web address was available to applicant(s) at least as of May 2013).

Health Protection Agency; Health effects of exposure to ultrasound and infrasound, Report of the independent advisory group on non-ionising radiation; RCE-14; pp. 1-180; Feb. 2010.

Heidenreich et al.; KCNQ4 K+ channels tune mechanoreceptors for normal touch sensation in mouse and man; Nature Neuroscience, 15; pp. 138-145; Jan. 2011.

Hepper et al.; Development of fetal hearing; Arch. Dis. Child. Fetal Neonatal Ed.; 71(2); pp. F81-F87; Sep. 1994.

Hering et al.; Smoking is associated with chronic sympathetic activation in hypertension; Blood Pressure; 19(3); pp. 152-155; Jun. 2010.

Hering et al.; Substantial reduction in single sympathetic nerve firing after renal denervation in patients with resistant hypertension (*wl* online data suppl.); Hypertension; 61; pp. 457-464; (online data suppl. 6 pgs.); Feb. 2013.

Hermida et al.; Bedtime dosing of antihypertensive medications reduces cardiovascular risk in CKD; J Am Soc Nephrol; 22(12); pp. 2313-2321; Dec. 2011.

Hermida et al.; Decreasing Sleep-Time Blood Pressure Determined by Ambulatory Monitoring Reduces Cardiovascular Risk. JACC, 58(11), pp. 1165-1173, Sep. 6, 2011.

(56) References Cited

OTHER PUBLICATIONS

Hermida et al.; Influence of time of day of blood pressure-lowering treatment on cardiovascular risk in hypertensive patients with type 2 diabetes; Diabetes Care; 34; pp. 1270-1276; Jun. 2011.
Heusser et al.; Carotid baroreceptor stimulation, sympathetic activity, baroreflex function, and blood pressure in hypertensive patients; Hypertension; 55; pp. 619-626; Mar. 2010.
Heusser et al.; Sympathetic vasomotor tone determines blood pressure response to long-term sibutramine treatment; J. Clin Endocrinol Metab; 92; pp. 1560-1563; Apr. 2007.
Hill, Ian G. W.; Stimulation of the vagus nerve and carotid sinus in man; Exp Physiol; 22(1); pp. 79-93; May 1932.
Hiraba et al. Optimal Vibrotactile Stimulation Activates the Parasympathetic Nervous System, in Advances in Vibration Engineering and Structural Dynamics (Eds. Beltran-Carbajal), Chapter 14; pp. 355-369; Oct. 2012.
Houix et al; Perceptual influence of the vibratory component on the audio component of alarms produced by rumble strips, by measuring reaction times; Proceedings of the Acoustics 2012 Nantes Conf.; Nantes, FR; pp. 1083-1088; Apr. 23-27, 2012.
Howitt et al.; Oscillatory pressure wave transmission from the upper airway to the carotid artery; J Appl Physiol; 103; pp. 1622-1627; Aug. 2007.
I. Interni Klinika Kardiologie; Addition of spironolaetone in patients with resistant arterial hypertension (ASPIRANT): a randomized, double-blind, placebo-controlled trial; 30 pgs.; http://spo.escardio.org/eslides/view.aspx? eevtid=48&fp=3041 (This web address was available to applicant(s) at least as of Feb. 22, 2013).
Ichinose et al.; Arterial baroreflex control of muscle sympathetic nerve activity under orthostatic stress in humans; Frontiers in Physiology; 3 (Art. 314); 10 pgs.; Aug. 2012.
Indiana University, K562 Hypertension, © 1998, 20 pgs.; printed Jun. 13, 2013 (http://www.indiana.edu/-k562/htn.html).
International Search Report, PCT/US2012/061118, Jan. 8, 2013, 7 pgs.
James et al.; Fetal learning: a prospective randomized controlled study; Ultrasound Obstet Gynecol; 20(5); pp. 431-438; Nov. 2002.
JS&A Group, Inc.; Bone Fone (product information); 1 pg.; © 1979; printed Jun. 1, 2012 (blog.mondermechanix.com/mags/MechanixIllustrated/11-198O/bone_phone.jpg).
Kaniusas, E., Acoustical Signals of Biomechanical Systems, Biomechanical Systems Technology, vol. 4; World Scientific publishing, Singapore; Chapter 1; pp. 1-44; Nov. 2007.
Kaufman, Mare; Mechanoreceptors and central command; Am J Physiol Heart Circ Physiol; 292; pp. H117-H118; Jan. 2007.
Kenny et al.; Carotid sinus massage in carotid sinus syndrome; Ulster Medical Journal, 59(1); pp. 93-95; Apr. 1990.
Kerschan-Schindl et al.; Whole-body vibration exercise leads to alteration in muscle; Clinical Physiology; 21 (3); pp. 377-382; May 2001.
Keyl et al.; Sinusoidal neck suction for evaluation of baroreflex sensitivity during desflurane and sevoflurane anesthesia; Anesth Analg; 95(6); pp. 1629-1636; Dec. 2002.
Kisilevsky et al.; Maturation of fetal responses to music; Developmental Science; 7(5); pp. 550-559; Nov. 2004.
Kreuzer et al.; Transcutaneous vagus nerve stimulation: retrospective assessment of cardiac safety in a pilot study; Frontiers in Psychiatry; 3 (Art. 70); 7 pgs.; Aug. 2012.
Krum, Henry; Renal Denervation (presentation); 29 pgs.; http://www.medtronic.com/rdn/pdfs/Krum%20-%20Renal%20Denervation%20%28ESC%202008%29.pdf; ESC 2008 (This web address was available to applicant(s) at least as of Oct. 22, 2011).
Lambert et al.; Advances in sympathetic nerve recording in humans; Frontiers in Physiology; 3 (Art. 11); 5 pgs.; Feb. 2012.
Lambert et al.; Single-unit muscle sympathetic nervous activity and its relation to cardiac noradrenaline spillover; J Physiol; 589(Pt. 10); pp. 2597-2605; May 2011.
LaRovere et al.; Baroreflex sensitivity: measurement and clinical implication; Ann Noninvasive Electrocardiol; 13(2); pp. 191-207; Apr. 2008.
Laude et al.; Comparison of various techniques used to estimate spontaneous baroreflex sensitivity (the EuroBaVa study); Am J Physiol Regul Integr Comp Physiol; 286; pp. R226-R201; Jan. 2004.
Lecanuet et al.; Fetal discrimination of low-pitched musical notes; Dev Psychobiol; 36(1); pp. 29-39; Jan. 2000.
Leduc et al.; Effect of chest wall vibration on the canine diaphragm during breathing; Eur Respir J; 19(3); 429-433; Mar. 2002.
Lehmkuhl et al.; Reproducibility of postexercise ambulatory blood pressure in State 1 hypertension; Journal of Human Hypertension; 19; pp. 589-595; May 2005.
Liu et al; Systemic and renal-specific sympathoinhibition in obesity hypertension (meeting abstract); The FASEB Journal; 25(mtg abstract supply; 1078.2; Apr. 2011.
Linz et al.; Renal sympathetic denervation suppresses postapneic blood pressure rises and atrial fibrillation in a model for sleep apnea; Hypertension; 60; pp. 172-187; Jul. 2012.
Lloyd-Jones et al.; Heart Disease and Stroke Statistics—2010 update; Circulation; 121; pp. e46-e215; Feb. 2010.
Lloyd-Jones et al.; Heart Disease and Stroke Statistics—2009 update; Circulation; 119; pp. e1-e161; Jan. 2009.
Lohmeier et al.; Disparate effects of systemic and renal-specific sympathoinhibition in obesity hypertension; Hypertension; 58; pp. e69; abstract No. P136; HBPR 2011; Orlando, FL; Sep. 20-24, 2011.
Lohmeier et al.; Prolonged activation of the baroreflex abolishes reduced kidney mass, salt-induced hypertension; Conf. Abstracts 61st Ann. High Blood Pressure Research Conf. 2007; Hypertension; 50(4); p. e85; abstract No. 050; Oct. 2007.
Majmaah University; Physical Exam Study Guides; 45 pgs.; http://faculty.mu.edu.sa/public/uploads/1331302627.864physical%20assessment%20guide.pdf (This web address was available to applicant(s) at least as of Apr. 4, 2012).
Mancia et al.; Arterial baroreflexes and blood pressure and heart rate variabilities in humans; Hypertension; 8(2); pp. 147-153; Feb. 1986.
Mancia et al.; Arterial baroreflexes in humans; in Handbook of Physiology (The Cardiovascular System, vol. 3); Chap. 20; pp. 755-793; Oxford Univ. Press, USA; Feb. 1988.
Mancia et al.; Carotid sinus baroreceptor control of arterial pressure in renovascular hypertensive subjects; Hypertension; 4(1); pp. 47-50; Jan./Feb. 1982.
Mancia et al.; Sympathetic activation in the pathogenesis of hypertension and progression of organ damage; Hypertension; 34; pp. 724-728; Oct. 1999.
Mancia, Giuseppe; Blood pressure reduction and cardiovascular outcomes: past, present, and future; Am J Cardiol; 100(3A) [suppl]; pp. 3J-9J; Aug. 2007.
Mark et al.; Microneurographic studies of the mechanisms of sympathetic nerve responses to static exercise in humans; Circ Res.; 57(3); pp. 461-469; Sep. 1985.
McCarren et al.; Vibration and its effect on the respiratory system; Australian Journal of Medicine; 52(1); pp. 39-43; Mar. 2006.
McCloskey et al.; Reflex cardiovascular and respiratory responses originating in exercising muscle; J. Physiol.; 224(1); pp. 173-186; Jul. 1972.
Medscape; Achieving guideline goals in the patient with diabetes; novel insights into CV risk reduction (CME/CE course for healthcare professionals); 95 pgs.; Nov. 2004 (www.medscape.org).
Mense et al.; Responses in muscle afferent fibres of slow conduction velocity to contractions and ischaemia in the cat; J. Physiol.; 342; pp. 383-397; Sep. 1983.
Morokuma et al.; Developmental change in fetal response to repeated low-intensity sound; Developmental Science 11 (1); pp. 47-52; Jan. 2008.
Muenter Swift et al.; Baroreflex control of muscle sympathetic nerve activity in postural orthostatic thachycardia syndrome; Am J Physiol Heart Circ Physiol; 289; pp. H1226-H1233; Sep. 2005.
Müller-Ehmsen, Jochen; Baroreflex activation therapy (BAT): Clinical experience in heart failure (presentation); American College of Cardiology, 61st Annual Scientific Sessions; Chicago, IL; 16 pgs.; Mar. 25, 2012.

(56) References Cited

OTHER PUBLICATIONS

Murai et al.; Advantage of recording single-unit muscle sympathetic nerve activity in heart failure; Frontiers in Physiology; 3 (Art. 109); 7 pgs.; May 2012.
Narayan et al.; Snoring effects on the baroreflex: an animal model; Respiratory Physiology & Neurobiology; 180(2-3); pp. 342-351; Mar. 2012.
Narkiewicz et al.; Cigarette smoking increases sympathetic outflow in humans; Circulation; 98; pp. 528-534; Aug. 1998.
Nat. Center for Health Services; Health, United States, 2010; Ca!. No. 76-641496; 563 pgs.; http://www.cdc.gov/nchs/data/hus/hus10.pdf; 2010 (This web address was available to applicant(s) at least as of Nov. 2, 2011).
Nat. Heart, Lung, and Blood Inst.; The 4th report on high blood pressure in children and adolescents; 50 pgs.; 2004; printed Aug. 19, 2013 (http://hp2010.nhlbihin.net/nhbpep_slds/bpped/download/hbp-ch.pdf).
Neldam et al. Telmisartan plus HCTZ vs. amlodipine plus HCTZ in older patients with systolic hypertension: results from a large ambulatory blood pressure monitoring study; AJGC; 15(3); pp. 151-160; May 2006.
New York Medical College; Microneurography and muscle sympathetic nerve activity (MSNA); 2 pgs.; downloaded Aug. 27, 2012 from http://www.nymc.edu/fhp/centers/syncope/microneurography.htm.
Nilsson, Ulrica; Music: a nursing intervention; Eur J Cardiovasc Nurs; 10; pp. 73-74; Oct. 2011.
Nishizaka et al.; Efficacy of low-dose spironalactone in subjects with resistant hypertension; AJH; 16(11); pp. 925-930; Nov. 2003.
Okada et al.; Experimental studies on the effects of vibration and noise on sympathetic nerve activity in skin; Eur J Appl Physiol; 62(5); pp. 324-331; May 1991.
Orion Med. Group, Inc.; Transcutaneous Mechanical Nerve Stimulator (User's Guide); 11 pgs.; printed Aug. 15, 2013 from website (http://www.medicalvibrator.com/sitebuildercontenUsitebuilderfiles/tmnsusermanual.pdf) This web address was available to applicant(s) at least as of Jul. 2013.
Panasonic Corp.; Panasonic announces wireless bone conduction headphones to the 2013 product lineup (press release); 1 pg.; Jan. 7, 2013; (http://www2.panasonic.com/webapp/wcs/stores/servleUprModelDetail? storeId= 11301&catalogId= 13251 &itemId= 693505&modelNo=Content01072013033005787 &surfModel=Content01072013033005787).
Papademetriou et al.; Carotid baroreceptor stimulation for the treatment of resistant hypertension; Intl J Hypertension; vol. 2011; Art. ID 964394; 5 pgs.; 2011 (Accepted for publn. Feb. 28, 2011).
Parati et al.; Blood pressure variability. Importance in research and in clinical hypertension; Arq Bras Cardiol; 67(2); pp. 131-133; Aug. 1996.
Park et al.; Contribution of the tonic vibration reflex to muscle stress and muscle fatigue; Scand J Work Envion Health; 19(1); pp. 35-42; Feb. 1993.
Park et al.; Differential distribution of muscle and skin sympathetic nerve activity in patients with end-stage renal disease; J Appl Physiol; 105; pp. 1873-1876; Dec. 2008.
Park et al.; Time of day for exercise on blood pressure reduction in dipping and nondipping hypertension; Journal of Human Hypertension; 19(8); pp. 597-605; Aug. 2005.
Pearson et al.; Spinal reflexes; Chapter 36; 16 pgs.; http://homepage.psy.utexas.edu/homepage/elass/psy394U/hayhoe/IntroSensoryMotorSystems/week5/ Kandel%20Ch% 2036.pdf (This web address was available to applicant(s) at least as of Oct. 9, 2012).
Pedersen, Christian; Human hearing at low frequencies (Ph.D. thesis); Aalborg Univ., DK; 100 pgs.; Mar. 2008.
Pedersen, Christian; Noise from large wind turbines (with focus on low frequencies); 40 pgs.; presentation slides; http://dasam.dklDasam_upload/dokumenter/noise_from_wind_turbines.pdf (this web address was available to applicant (s) at least as of Mar. 29, 2012).
Perkovic et al; The burden of blood pressure-related disease: a neglected priority for global health; Hypertension; 50; pp. 991-997; Dec. 2007.
PFCD; Almanac of chronic disease 2008 edition; pp. 1-78; 2008 (year of pub. sufficiently earlier than effective US filing date and any foreign priority date).
Pimenta et al.; Resistant hypertension: Incidence, prevalence, and prognosis; Circulation; 125; pp. 1594-1596; Apr. 2012.
Poole et al.; Temporary threshold shifts as indicators of hand-arm vibration exposure (research report 479); Health and Safety Laboratory; HSE Books; pp. 1-47; Nov. 2006.
Popular Science; Jawbone radio; Popular Science; 197(1); p. 41; Jul. 1970.
Potthoff et al.; Novel approaches in hypertension treatment-modulation of the sympathetic overactivity; in Aspects of Pacemakers—Functions and Interactions in Cardiac and Non-Cardiac Indication (Ed. Oliver Vonend); InTech; pp. 1-18; Sep. 2011.
Querry et al.; Anatomical and functional characteristics of carotid sinus stimulation in humans; Am J Physiol Heart Circ Physiol; 280(5); pp. H2390-H2398; May 2001.
Raine et al.; A simplified paired neck chamber for the demonstration of baroreflex blood pressure regulation; Am J Physiol; 277 (Advan in Physiol Educ, 22); pp. S60-S66; Dec. 1999.
Ranjbar et al.; Vibrotactile detection, identification and directional perception of signal-processed sounds from environmental events: A pilot field evaluation in five cases; Iranian Rehabilitation Journal; 6(7&8); pp. 89-107; Dec. 2008.
Ranjbar et al.; Vibrotactile identification of signal-processed sounds from environmental events; J Rehanil Res Dev; 46(8); pp. 1021-1036; 2009 (year of pub. sufficiently earlier than effective US filing date and any foreign priority date).
Ranjbar, P., Sensing the Environment: Development of Monitoring Aids for Persons with Profound Deafness of Deafblindness, Doctoral Dissertation; Örebro University; 93 pgs.; Sep. 2009.
Rau et al.; Psychophysiology of arterial baroreceptors and the etiology of hypertension; Biological Psychology; 57(1-3); pp. 179-201; Jul.-Aug. 2001.
Reflexonic; Viberect® product brochure; 2 pgs.; © 2013; printed Aug. 15, 2013 from website (http://reflexonic.com/pdf/Brochure%20Doctors%20Trifold%20Reflexonic.pdf) This web address was available to applicant(s) at least as of Jul. 2013.
Ribot-Ciscar et al.; Alteration of human cutaneous afferent discharges as the result of long-lasting vibration; J Appl Physiol; 80(5); pp. 1708-1715; May 1996.
Roger et al. (writing group members); Heart disease and stroke statistics—2012 update: a report from the american heart association; Circulation; 125; pp. e2-e220; Jan. 2012.
Romm et al.; Learn the brachial plexus in five minutes or less; 21 pgs.; http://www.ama-assn.org/resources/doc/mss/brachiaLplex_how_to.pdf (This web address was available to applicant(s) at least as of Apr. 1, 2012).
Sabbah, Hani; Baroreflex activation therapy for the treatment of heart failure; Intl. Academy of Cardiology, 13th World Congress on Heart Disease, Ann. Scientific Sessions 2007; Vancouver, BC, Canada; 21 pgs.; Jul. 31, 2007.
Sajous, Charles E.; Chapter XX: The internal secretions in their relation to pharmacodynamics; in The internal secretions and the Principles of medicine (2nd Vol., 6th Ed.); FA Davis Co.; pp. 1259-1306; 1914 (year of pub. sufficiently earlier than effective US filing date and any foreign priority date).
Salvetti et al.; Thiazide diuretics in the treatment of hypertension: an update; J Am Soc Nephrol; 17(4)(supp 2); pp. 825-829; Apr. 2006.
Sanders et al.; Arterial baroreflex control of sympathetic nerve activity during elevation of blood pressure in normal man: dominance of aortic baroreflexes; Circulation; 77(2); pp. 279-288; Feb. 1988.
Sarafidis et al.; Resistant hypertension; J Am Coll Cardiol; 52(22); 1749-57; Nov. 2008.
Sato, M., Response of Pacinian Corpuscles To Sinusoidal Vibration, J Physiol, 159; pp. 391-409; Dec. 1961.
Schust, M.; Effects of low frequency noise up to 100 Hz; Noise Health; 6(23); pp. 73-85; Apr.-Jun. 2004.
Seagard et al.; Acute resetting in two functionally different types of carotid baroreceptors; Circ Res; 70(3); pp. 559-565; Mar. 1992.

(56) References Cited

OTHER PUBLICATIONS

Shamsuzzaman et al.; Elevated C-reactive protein in patients with obstructive sleep apnea; Circulation; 105; pp. 2462-2464; May 2002.
Shamsuzzaman et al.; Obstructive sleep apnea; JAMA; 290(14); pp. 1906-1914; Oct. 2003.
Siegal et al.; Noninvasive, transthoracic, low-frequency ultrasound augments thrombolysis in a canine model of acute myocardial infarction; Circulation; 101; pp. 2026-2029; May 2000.
Sievert et al.; Results from symplicity HTN-1 and symplicity HTN-2; CardioVascular Center Frankfurt; Frankfurt, Germany; 38 pgs.; printed Aug. 19, 2013 (www.leipzig-interventional-course.com/index.php).
Somers et al.; Sympathetic neural mechanisms in obstructive sleep apnea; J. Clin. Invest.; 96; pp. 1897-1904; Oct. 1995.
Somers et al.; Sympathetic-nerve activity during sleep in normal subjects; N Engl J Med; 328(5); pp. 303-307; Feb. 1993.
St. Jude Medical; Investor Conference (presentation); 299 pgs.; Feb. 4, 2011.
Staras et al., Resetting of Sympathetic Rhythm by Somatic Afferents Causes Post-Reflex Coordination of Sympathetic Activity in Rat, Journal of Physiology, 533.2, pp. 537-545, Jun. 2001.
Stillman, Barry; Vibratory motor stimulation; Aust. J. Physiother.; 16; pp. 118-123; Sep. 1970.
Stoyneva et al.; Current pathophysiological views on vibration-induced Raynaud's phenomenon; Cardiovascular Research; 57(3); pp. 615-624; Mar. 2003.
Stuart, Mary; Masterminds of Ardian: An interview with inventors Mark Gelfand and Howard Levin; Start-Up; Article #2011900004; 16 pgs.; Jan. 2011; (http://sis.windhover.com/document.php?id=2011900004).
Suchkova et al.; Ultrasound improves tissue perfusion in ischemic tissue through a nitric oxide dependent mechanism; Thromb Haemost; 88(5); pp. 865-870; Nov. 2002.
Syntichaki et al., Genetic Models of Mechanotransduction: The Nematode *Caenorhabditis elegans*, Physiol Rev, 84: pp. 1097-1153, Oct. 2004.
Tank et al.; Limited effect of systemic ?-blockade on sympathetic outflow; Hypertension; 38; pp. 1377-1381; Dec. 2001.
Tank et al.; Selective impairment in sympathetic vasomotor control with norepinephrine transporter inhibition; Circulation; 107; pp. 2949-2954; Jun. 2003.
Thrasher, Terry; Baroreceptors and the long-term control of blood pressure; Exp Physiol; 89(4); pp. 331-341; Jul. 2004.
Toorop, Raechel; Surgical interventions and studies of the carotid sinus (dissertation); Utrecht University; 175 pgs.; Feb. 2012.
Torvinen, Saila, Effect of Whole Body Vibration on Muscular Performance, Balance, and Bone (Academic Dissertation), Acta Universitatis Tamperensis, University of Tampere, pp. 1-59; Feb. 8, 2003.
Tsioufis et al.; Increased nighttime blood pressure or nondipping profile for prediction of cardiovascular outcomes; J Hum Hypertens; 25(5); pp. 281-293; May 2011.
Tufail et al.; Ultrasonic neuromodulation by brain stimulation with transcranial ultrasound; Nature Protocols; 6(9); pp. 1453-1470; Sep. 2011.
Tufail, Yusuf Zahid; Development of a neurostimulation method using pulsed ultrasound (dissertation); Arizona State Univ.; 205 pgs.; May 2011.
Van Der Linden et al.; Buzzing to play: lessons learned from an in the wild study of real-time vibrotactile feedback; CHI 2011; Proceedings of the SIGCHI Conf. o Human Factors in Computing Systems; Vancouver, BC; pp. 533-542; May 7-12, 2011.
Verdecchia et al.; Day-night dip and early-morning surge in blood pressure in hypertension: prognostic implications; Hypertension; 60; pp. 34-42; Jul. 2012.
Wallin et al.; Renal noradrenaline spillover correlates with muscle sympathetic activity in humans; Journal of Physiology; 491.3; pp. 881-887; Mar. 1996.
Walsh et al.; Carotid sinus massage—How safe is it?; Age and Ageing; 35(5); pp. 518-535; Sep. 2006.
Watson et al. (committee); Speech-perception aids for hearing-impaired people: Current status and needed research; J. Acoust. Soc. Am.; 90(2) Pt. 1; pp. 637-685; Aug. 1991.
Weerakkody et al., Impairment of Human Proprioception by High-Frequency Cutaneous Vibration, J. Physiol; 581 (Pt. 3); pp. 971-980, Jun. 15, 2007.
Westerhof et al.; Time-domain cross-correlation baroreflex sensitivity: performance on the EUROBAVAR data set; J. Hypertens; 22(7); pp. 1371-1380; Jul. 2004.
White et al.; "The nighttime might be the right time" for cardiovascular event prediction; Hypertension; 60(1); pp. 8-9; Jul. 2012.
Wigram, Anthony L.; The effects of vibroacoustic therapy on clinical populations (thesis); London University; 290 pgs.; 1997 (year of pub. sufficiently earlier than effective US filing date and any foreign priority date).
Wilfred Laurier University; Sound effects (annual newsletter); vol. 4; 28 pgs; Fall 2007 (Sept.).
Winkler et al.; newborn infants detect the beat in music; PNAS/ 106(7); pp. 2468-2471; Feb. 2009.
Wustmann et al.; Effects of chronic baroreceptor stimulation on the autonomic cardiovascular regulation in patients with drug-resistant arterial hypertension; Hypertension; 54; pp. 530-536; Sep. 2009.
Yoshimoto et al.; Functional role of diverse changes in sympathetic nerve activity in regulating arterial pressure during REM sleep; Sleep; 34(8); pp. 1093-1101; Aug. 2011.
Young et al.; Cost-effectiveness of treating resistant hypertension with an implantable carotid body stimulator; Journal of Clinical Hypertension; 11 (1 0); pp. 555-563; Oct. 2009.
Yu, et al. Implementation of Portable Monitor based on Mobile Phone for Music Therapy on Hypertension, 2010 3rd International Conference on Biomedical Engineering and Informatics (BMEI); Yantai, China; vol. 5; pp. 1923-1926; Oct. 16-18, 2010.
Zanchetti, Alberto; Carotid baroreflex physiology and baroreflex activation therapy mechanism of action; Paris, FR; ESC; 1759Z-1778Z; Aug. 30, 2012 (http://www.cvrx.com/wp-contentluploads/2013/05/Zanchetti_Slides_Final.pdf).
Jul. 21, 2014 Office Action in related Australian Application No. 2012325893, 4 pages.
Jun. 5, 2014 International Search Report and Written Opinion for related International Application No. PCT/US2014/021631 (12 pages).
U.S. Appl. No. 14/401,481, filed Nov. 14, 2014, Ehrenreich.
Jul. 21, 2014 Office Action in Australian App. No. 2012325893 (4 pages).
Aug. 9, 2013 International Search Report for Int'l App. No. PCT/US2013/041465 (8 pages).

\* cited by examiner

METHODS AND DEVICES FOR TREATING HYPERTENSION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

This invention relates generally to methods and devices for the treatment of hypertension. More specifically, methods and devices which treat hypertension using devices disposed extra corporally.

Hypertension, or high blood pressure, affects millions of people every day and is a serious health hazard. Hypertension is associated with an elevated risk for heart attack, heart failure, arterial aneurysms, kidney failure and stroke. There are many factors that may affect blood pressure, such as: salt intake, obesity, occupation, alcohol intake, smoking, pregnancy, stimulant intake, sleep apnea, genetic susceptibility, decreased kidney perfusion, arterial hardening and medication(s). Many times people are unaware that they suffer from hypertension until it is discovered during a medical check-up with their health care practitioner (HCP), or worse, it is discovered when they are hospitalized for a hypertension related condition such as a heart attack or stroke.

Blood pressure is controlled by a complex system within the body, one component of this system is known as the arterial baroreflex (ABR). The baroreflex is the fastest autonomic reflex responding to changes in blood pressure. The baroreceptor nerve endings are embedded in vessels throughout the circulatory system and encode both mean pressure and rate of change of pressure as a frequency. Centers in the brainstem process spikes in the frequency information, integrating it with other information and providing a signal to the sinoatrial (SA) pacemaking node of the heart via efferent fibers in the vagus nerve. When blood pressure becomes too high, the resulting vagal nerve signal triggers the release of acetylcholine at the SA node of the heart, slowing the heart rate and thus lowering the blood pressure.

Baroreceptors are located in the transverse aortic arch and the carotid sinuses of the left and right internal carotid arteries. The baroreceptors found within the aortic arch monitor the pressure of blood delivered to the systemic circuit, and the baroreceptors within the carotid arteries monitor the pressure of the blood being delivered to the brain.

As described above, the arterial baroreceptors are stretch receptors that are stimulated by distortion of the arterial wall when pressure changes. The baroreceptors can identify the changes in the average blood pressure or the rate of change in pressure with each arterial pulse. Action potentials triggered in the baroreceptor endings are then conducted to the brainstem where central terminations (synapses) transmit this information to neurons within the solitary nucleus. Reflex responses from such baroreceptor activity can trigger increases or decreases in the heart rate. Arterial baroreceptor (ABR) sensory endings are simple, sprayed nerve endings that lie in the tunica adventitia of the artery. An increase in the mean arterial pressure increases depolarization of these sensory endings, which results in action potentials. These action potentials are conducted to the solitary nucleus in the central nervous system by axons and have a reflex effect on the cardiovascular system through autonomic neurons.

At normal resting blood pressures, baroreceptors discharge at approximately 1 out of every 3 heart beats. If blood pressure falls, the arteries retract in diameter and the baroreceptor firing rate decreases with the drop in blood pressure the brain send a signal to the heart to increase blood pressure by increasing heart rate. Signals from the carotid baroreceptors are sent via the glossopharyngeal nerve (cranial nerve IX). Signals from the aortic baroreceptors travel through the vagus nerve (cranial nerve X). Arterial baroreceptors inform reflexes about arterial blood pressure.

The arterial baroreflex system is a dynamic system that is capable of adapting to ever changing situations. The ABR is the reason why we do not pass out when moving from a seated to standing position. In this instance the ABR senses a change in blood pressure and accommodates the change by sending the appropriate signal to regulate blood pressure. The ABR system also performs an essential function to regulate blood pressure during exercise, wherein during exercise your heart rate increases as well as your blood pressure, however, at a certain point during exercise the ABR will intervene, allowing the heart rate to further increase but not allowing the blood pressure to further increase.

As stated above, hypertension currently affects a large and growing population. Currently treatments for hypertension range from prescribed lifestyle changes and the use of pharmaceutical products. Within the past couple of years, new surgical therapies are emerging. These surgical therapies either lead to the implantation of a device for stimulating a patient's carotid baroreceptor or to the disconnection of the nerves of the renal arteries.

If prescribed lifestyle changes do not address a patient's hypertension, their HCP will typically prescribe drug therapy to treat their hypertension. There are multiple classes of pharmaceutical products that can be utilized to treat hypertension. These include vasodilators to reduce the blood pressure and ease the workload of the heart, diuretics to reduce fluid overload, inhibitors and blocking agents of the body's neurohormonal responses, and other medicaments. Many times, a HCP will prescribe one or more of these products to a patient to be taken in combination in order to lower their blood pressure. However, the use of pharmaceutical products is not without their risks. Many of these products carry severe warnings of potential side effects. Additionally, each patient may respond differently to the products, therefore multiple office visits may be required before the right dosage and type of pharmaceutical products are selected, which leads to greater health care costs. Further still there are a number of patients who either do not respond to medication, refuse to take medication, or over time the medication no longer provides a therapeutic effect. Recently, new clinical trial data has drawn correlations between the use of diuretic pharmaceutical products to treat high blood pressure and the formation of diabetes within the patient.

For patients who do not respond to drug therapy, there are medical devices and treatments that can be utilized to treat high blood pressure. Some of these devices involve invasive surgical procedures including the implantation of a permanent medical device within a patient's artery to impart a force at a specific location within the artery which then may cause a lowering of blood pressure. However, these devices are relatively new or are still under development and have not been proven over a long period of time. Also, since the device is a permanent implant, there is always the possibility of complications during the implantation process or infections related to the implantation.

As described above, another type of invasive medical device is an electrical signal generating implant, where electrodes are placed adjacent to the carotid artery. With this process, the surgeon must be careful not to sever any of the nerves while implanting the device. If the nerves are severed, then the device will not function properly and may lead to long term health complications for the patient. However, even more troubling is that the patient has now permanently lost a baroreceptor for controlling blood pressure naturally, which may lead to complications later, which are currently unknown. Additionally, the implant device requires regular battery replacement, which to do so requires another invasive surgical procedure.

Another type of invasive medical device and procedure being developed is the use of ablation catheter to denervate the carotid body, specifically the chemoreceptors of the carotid body. Similar to the device and procedure described above, this device permanently causes a disconnection between the chemoreceptors and the nervous system/brain. The long term effects are unknown, additionally, other nerves maybe destroyed or disconnected during the procedure which may lead to other side effects.

Another type of invasive medical procedure to treat hypertension being developed is to use an ablation catheter placed within the renal artery, where a series of energy pulses are performed to ablate (sever) the nerves surrounding the artery, thereby effectively disconnecting the nerves of the kidney from the body. This procedure results in a permanent and non-reversible change to the patient's nervous system, this procedure is being referred to as renal nerve ablation or renal denervation. The long term effects of such a permanent treatment are unknown at this time as this approach is relatively new on the market. Recently published data has shown that not all patients respond to this surgical procedure, that is after the procedure, some of the patients show little to no changes in their blood pressure. This may be concerning as now these patients have had their renal arteries permanently disconnected from their kidneys, which may lead to long term effects which are unknown at this time. Additionally, the costs associated with an invasive medical procedure are not insignificant, only to prove that the procedure had no effect, thus, instead of potentially lowering the cost of treatment for these patients, the cost of treating their hypertension was significantly added to.

Additionally, the recently published data also shows that patients who respond to renal denervation may still remain hypertensive. Thus, the renal denervation procedure may not be a "cure," instead it may be seen as an adjunctive therapy, as such these patients may remain on drug therapies or are recommended to remain on drug therapy after having undergone renal denervation.

Yet another invasive surgical approach to address hypertension is a combination of a device and a pharmaceutical product, wherein a catheter with a needle disposed near its distal end are placed within the renal artery. Once in position, a liquid pharmaceutical product is injected into the wall of the artery, whereby the pharmaceutical product is designed to chemically ablate the renal nerves. Here again, this treatment procedure is considered to be a permanent solution, whereby the nerves are permanently severed. Long term efficacy of the severing of the renal nerves is unknown. Additionally, long term effects of the procedure are also unknown.

Human skin acts as the protective barrier between our internal body systems and the outside world. Our skin in combination with our bodies nerves provides for the ability to perceive touch sensations and gives our brains a wealth of information about the environment around us, such as temperature, pain, and pressure. Without such a nervous system, we wouldn't be able to feel our feet hitting the floor when we walked, we wouldn't sense when something sharp cut us, and we wouldn't feel the warmth of the sun on our skin.

Human skin is composed of several layers. The very top layer is the epidermis and is the layer of skin you can see. In Latin, the prefix "epi-" means "upon" or "over," thus the epidermis is the layer upon which the dermis is disposed (the dermis is the second layer of skin). The epidermis, made of dead skin cells, is waterproof and serves as a protective wrap for the underlying skin layers and the rest of the body. It contains melanin, which protects against the sun's harmful rays and also gives skin its color. When you are in the sun, the melanin builds up to increase its protective properties, which also causes the skin to darken. The epidermis also contains very sensitive cells called touch receptors that give the brain a variety of information about the environment the body is in.

The second layer of skin is the dermis. The dermis contains hair follicles, sweat glands, sebaceous (oil) glands, blood vessels, nerve endings, and a variety of touch receptors. The dermis' primary function is to sustain and support the epidermis by diffusing nutrients to it and replacing the skin cells that are shed off the upper layer of the epidermis. New cells are formed at the junction between the dermis and epidermis, and they slowly push their way towards the surface of the skin so that they can replace the dead skin cells that are shed. Oil and sweat glands eliminate waste produced at the dermis level of the skin by opening their pores at the surface of the epidermis and releasing the waste.

The bottom skin layer is the subcutaneous tissue which is composed of fat and connective tissue. The layer of fat acts as an insulator and helps regulate body temperature. It also acts as a cushion to protect underlying tissue from damage when you bump into things. The connective tissue keeps the skin attached to the muscles and tendons underneath.

Our sense of touch is controlled by a huge network of nerve endings and touch receptors disposed within the skin which is known as the somatosensory system. This system is responsible for all the sensations we feel: cold, hot, smooth, rough, pressure, tickle, itch, pain, vibrations, and more. Within the somatosensory system, there are four main types of receptors; mechanoreceptors, thermoreceptors, nociceptors, and proprioceptors.

It is important to understand how specialized receptors adapt to a change in stimulus (anything that touches the skin and causes sensations such as hot, cold, pressure, tickle, etc.). A touch receptor is considered rapidly adapting if it responds to a change in stimulus very quickly. This means that it can sense right away when the skin is touching an object and when it stops touching that object. However, rapidly adapting receptors can't sense the continuation and duration of a stimulus touching the skin (how long the skin is touching an object). These receptors best sense vibrations occurring on or within the skin. A touch receptor is considered slowly adapting if it does not respond to a change in stimulus very quickly. These receptors are very good at sensing the continuous pressure of an object touching or indenting the skin but are not very good at sensing when the stimulus started or ended.

Mechanoreceptors are receptors which perceive sensations such as pressure, vibrations, and texture. There are four known types of mechanoreceptors whose only function is to perceive indentions and vibrations of the skin: Merkel's disks, Meissner's corpuscles, Ruffini's corpuscles, and Pacinian corpuscles.

The most sensitive mechanoreceptors, Merkel's disks and Meissner's corpuscles, are found in the very top layers of the dermis and epidermis and are generally found in non-hairy skin such as the palms, lips, tongue, soles of feet, fingertips, eyelids, and the face. Merkel's disks are slowly adapting receptors and Meissner's corpuscles are rapidly adapting receptors so your skin can perceive both when you are touching something and how long the object is touching the skin.

Located deeper in the dermis and along joints, tendons, and muscles are Ruffini's corpuscles and Pacinian corpuscles. These mechanoreceptors can feel sensations such as vibrations traveling down bones and tendons, rotational movement of limbs, and the stretching of skin.

Another type of receptors are thermoreceptors, as their name suggests, these receptors perceive sensations related to the temperature of objects the skin feels. They are found in the dermis layer of the skin. There are two basic categories of thermoreceptors: hot and cold receptors.

Cold receptors start to perceive cold sensations when the surface of the skin drops below 95° F. They are most stimulated when the surface of the skin is at 77° F. and are no longer stimulated when the surface of the skin drops below 41° F. This is why your feet or hands start to go numb when they are submerged in icy water for a long period of time.

Hot receptors start to perceive hot sensations when the surface of the skin rises above 86° F. and are most stimulated at 113° F. But beyond 113° F., pain receptors take over to avoid damage being done to the skin and underlying tissues.

Thermoreceptors are found all over the body, but cold receptors are found in greater density than heat receptors. The highest concentration of thermoreceptors can be found in the face and ears.

Another type of receptor are pain receptors, commonly known as nociceptors, "Noci-" in Latin means "injurious" or "hurt." These receptors detect pain or stimuli that can or does cause damage to the skin and other tissues of the body. There are over three million pain receptors throughout the body, found in skin, muscles, bones, blood vessels, and some organs. They can detect pain that is caused by mechanical stimuli (cut or scrape), thermal stimuli (burn), or chemical stimuli (poison from an insect sting).

These receptors cause a feeling of sharp pain to encourage you to quickly move away from a harmful stimulus such as a broken piece of glass or a hot stove stop. They also have receptors that cause a dull pain in an area that has been injured to encourage you not to use or touch that limb or body part until the damaged area has healed. While it is never fun to activate these receptors that cause pain, these receptors play an important part in keeping the body safe from serious injury or damage by sending these early warning signals to the brain.

Another receptor type are proprioceptors, the word "proprius" means "one's own" and is used in the name of these receptors because they sense the position of the different parts of the body in relation to each other and the surrounding environment. Proprioceptors are found in tendons, muscles, and joint capsules. This location in the body allows these special cells to detect changes in muscle length and muscle tension. Without proprioceptors, we would not be able to do fundamental things such as feeding or clothing ourselves.

While many receptors have specific functions to help us perceive different touch sensations, almost never is just one type active at any one time. When drinking from a freshly opened can of soda, your hand can perceive many different sensations just by holding it. Thermoreceptors are sensing that the can is much colder than the surrounding air, while the mechanoreceptors in your fingers are feeling the smoothness of the can and the small fluttering sensations inside the can caused by the carbon dioxide bubbles rising to the surface of the soda. Mechanoreceptors located deeper in your hand can sense that your hand is stretching around the can, that pressure is being exerted to hold the can, and that your hand is grasping the can. Proprioceptors are also sensing the hand stretching as well as how the hand and fingers are holding the can in relation to each other and the rest of the body.

None of the sensations described above and felt by the somatosensory system would make any difference if these sensations could not reach the brain. The nervous system of the body takes up this important task. Neurons, which are specialized nerve cells that are the smallest unit of the nervous system, receive and transmit messages with other neurons so that messages can be sent to and from the brain. This allows the brain to communicate with the body. When your hand touches an object, the mechanoreceptors in the skin are activated, and they start a chain of events by signaling to the nearest neuron that they touched something. This neuron then transmits this message to the next neuron which gets passed on to the next neuron and on it goes until the message is sent to the brain. Now the brain can process what your hand touched and send messages back to your hand via this same pathway to let the hand know if the brain wants more information about the object it is touching or if the hand should stop touching it.

Vibration experiments have been conducted to test the effects of vibration, the results of such an experiment were published in 1961 in the Journal of Physiol. (1961), 159 pp. 391-409, entitled "Response of Pacinian Corpuscles to Sinousoidal Vibration, by M. Sato. In this experiment it was proven that vibrations can excite the nervous system similar to utilization of electrical stimulation.

Other experiments have shown that the 1st Node of Ranvier gaps can be excited by either mechanical transduction or acoustic stimulation. The 1st Node of Ranvier gaps are gaps formed between myelin sheaths between different cells.

In a 1967 publication entitled "The Relative Sensitivity to Vibration of Muscle Receptors of the Cat," M. C. Brown, I. Engberger and P. B. C. Matthews, Journal Physiol. (1967), 192 PP 773-800, the authors tested vibrations and concluded that vibratory effects persist as long as the vibration continues. Additionally, the authors cited another publication, 1966 Matthews, "Reflex excitation of the soleus muscle of the decerebrate cat caused by vibration applied to tendon" where vibration, was applied to a non-contracting muscle, provides a way of selectively activating nearly all of the nerve fibers from the primary endings to discharge repetitively. In contrast to electrical stimulation, vibration provides for a more selective activation.

Electrical stimulation will stimulate those nerves which are located in the close proximity to the electrical source, however, electrical stimulation will seek the lowest resistance pathway and is typically localized to the area of application. In contrast, vibrational stimulation carries the benefit of exciting afferent fibers at a distance from the location of the application of the vibration.

In 2000 a publication by Alfrey entitled "Characterizing the Afferent Limb of the Baroreflex" Rice University, Houston Tex., April 2000, UMI Microform 99-69-223. The author concluded that the baroreflex is the fastest autonomic reflex responding to changes in blood pressure. Baroreceptor nerve endings embedded in vessels throughout the circulatory system encode both mean pressure and rate of change of pressure as a frequency-modulated train of action potentials (spikes). Centers in the brainstem process the spike train information, integrating it with information from higher centers and providing a signal to the sinoatrial (SA) pacemaking node of the heart via efferent fibers in the vagus nerve. When blood pressure becomes too high, the resulting vagal signal triggers the release of acetylcholine at the SA node of the heart slowing heart rate and thus lowering blood pressure.

In another paper, published in 2004 by Syntichaki et al., entitled "Genetic Models of Mechanotransduction: The Nematode Caenorhabditis elegans" Physol Rev. 84: 1097-1153, 2004 10.1152/physrev.0043.2003, it was found that all vertebrates respond to similar mechanosensory stimuli, therefore it's likely that two humans would have similar response to the same wavelengths or frequencies.

Lastly, while there are number of different therapies available on the market and new therapies emerging, there are patient populations that cannot be treated through the use of the existing drugs or devices.

One such population is patients who develop high blood pressure during pregnancy. Health care practitioners are generally hesitant to prescribed pharmaceutical products in these situations as there may be unknown side effects to the mother and unborn child. Furthermore, many hypertensive pharmaceutical products have not been properly tested for use during pregnancy; therefore, there is much hesitancy on behalf of the prescribing physician to use such drug products due to potential untested side-effects as well as potential litigation arising from a side-effect. Pregnancy induced hypertension, gestational hypertension or preeclampsia may not be a permanent condition and may be resolve after delivery. Therefore, the use of permanent therapies, such as renal denervation, may not be warranted in this situation. Additionally, surgical procedures are not generally recommended during pregnancy.

There is yet another hypertensive population emerging in today's world is the hypertensive adolescent. Over the past 30 years, the number of adolescent hypertensives has risen to a rate of over 3.7% diagnosed hypertensive and 3.4% diagnosed pre-hypertensive. Only 1 in 4 adolescents are currently diagnosed. Many of the currently available pharmaceutical products have not been tested on an adolescent population, therefore, as described above, many physicians are hesitant to prescribe drug therapies due to unknown side effects or long term effects they may have. Furthermore, the adolescent population poses yet another difficulty in that they are still developing and undergoing puberty and bone growth. Therefore, there is a need for a non-invasive, non-pharmaceutical solution to address this growing patient population.

Thus, it would be desirable to provide improved methods, devices and systems for artificial and selective activation of a patient's baroreflex or nervous system in order to achieve a variety of therapeutic objectives, including the control of hypertension, renal function, heart failure, and the treatment of other cardiovascular disorders. It would be particularly desirable if such methods and systems were non-invasive, reversible, safe and/or external to the patient.

BRIEF DESCRIPTION

In accordance with the present invention there is provided a device for treatment of hypertension, comprising, a housing, the housing have a proximal end and a distal end; and a driver assembly within the housing, the driver assembly electrically coupled to an energy source, the energy source disposed within the housing.

In accordance with the present invention there is provided a device for imparting energy to a patient, comprising, a housing, the housing having a proximal end, a distal end and defining a volume therebetween; a driver assembly is disposed within the volume of the housing; an energy source coupled to the driver assembly; and an electronics module coupled to the driver assembly and the energy source, wherein the electronics module controls the driver assembly.

In accordance with the present invention there is provided a device for treating hypertension, the device comprising, a housing, the housing having a proximal surface and a distal surface, wherein the housing further includes a mounting system, the mounting system including a first member and a second member, the first member associated with the housing and the second member configured to be received by tissue; and a driver assembly within the housing.

In accordance with the present invention this is provided a device for imparting energy to a patient, the device comprising: a housing, the housing having a first surface and a second surface, the surfaces defining a volume therebetween, wherein the housing further includes a mounting system, the mounting system including a first member and a second member, the first member associated with the housing and the second member configured to be received by tissue; a driver assembly disposed within the volume of the housing; an energy source coupled to the driver assembly; and an electronics module coupled to the driver assembly and the energy source.

In accordance with the present invention there is provided a method of providing therapy, the method comprising: applying a therapy applying device to a collar bone of a patient; and activating a driver assembly within the therapy applying device.

DETAILED DESCRIPTION

Figure 1:
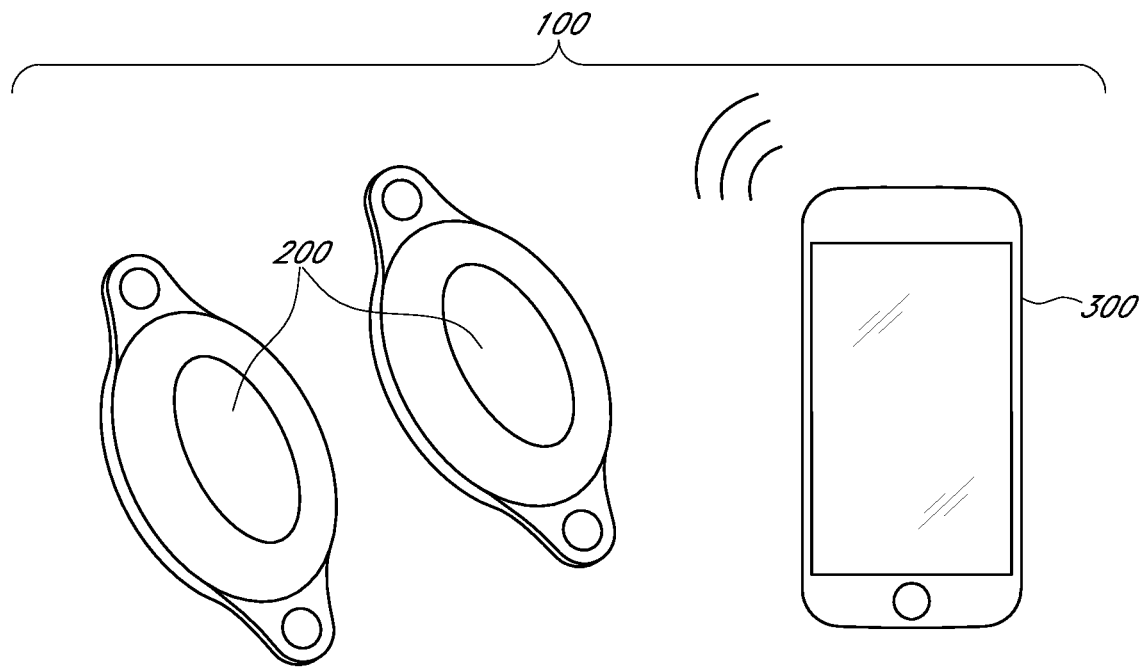
FIG. 1 is an exemplary embodiment of the therapy system in accordance with the present invention.

The following detailed description illustrates embodiments of the invention by way of example and not by way of limitation. The description clearly enables one skilled in the art to make and use the disclosure, describes several embodiments, adaptations, variations, alternatives, and uses of the disclosure, including what is presently believed to be the best mode of carrying out the disclosure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

In accordance with the present invention there is provided devices and methods for the treatment of hypertension. The device of the present invention is configured to be detachably attached to a user, wherein the device is aligned with a bone of the user's body. Once affixed to the patient, the device can be activated either manually or remotely, wirelessly or wired, through the use of a software program running on a computing device or a software program within the device. The activation may be timed to coincide with a patient's sleep pattern, such that therapy is provided by the device to the patient in the evening and again in the morning prior to the patient waking up. It is believed that providing therapy during a sleep cycle is beneficial.

In accordance with embodiments of the present invention the device is detachably attached to a patient's tissue and is intended to engage a portion of the patient's skeletal frame, particularly the clavicle. It shall be understood that although the present invention is described in reference to the collar bone or clavicle, it shall be understood that this should not be limiting in any manner. As described above, in a preferred embodiment the methods and devices of the present invention utilize the clavicle. However, the methods and devices of the present invention may be utilized with other dermal bones such as the skull, jawbone, knee cap (patella) or non-dermal bones such as the wrist bone, ribs, scapula. Methods and devices of the present invention can also be used above any portion of the body containing somatory sensors such as proprioceptors, nociceptors, mechanoreceptors or thermoreceptors. Dermal bones are unique in that dermal bone does not form from cartilage first and then calcify. Dermal bone is formed within the dermis and it grows by accretion only; that is, the outer portion of the bone is deposited by osteocytes. Dermal bones have been utilized to transmit sound for other devices such as in hearing aids.

Referring now to FIG. 1, there is shown the therapy system 100 in accordance with the present invention. As shown in FIG. 1, the therapy system 100 in accordance with the present invention may include a pair of therapy providing devices 200 and optionally a computing device 300. The therapy providing system 100 may further include a charging/storage system as will be described in detail below with reference to FIG. 11. Additionally, the therapy providing device 200 may further include an integrated or separate attachment system to detachably attach the system 100 to a user's skin as will be described in greater detail below.

As shown in FIG. 1, the computing device 300 in one aspect is configured to communicate with the therapy providing device 200 through a wireless communication protocol such as through the use of WIFI, BLUETOOTH, ZIGBEE, RFID, NFC, ANT+, cellular, infrared or other known wireless communication protocols. Alternatively, the computing device 300 and the therapy providing devices 200 may be communicatively coupled together using a physical connection such as an electrical wire, a plurality of electrical wires, electrical cable, fiber optic or using other known physical connections capable of transmitting signals between the devices. As shown in FIG. 1, it is contemplated that the methods of use in accordance with the present invention would utilize two therapy providing devices 200 as shown. If two therapy providing devices 200 are utilized, they are intended to be disposed on a user about the left and right clavicle. In accordance with the present invention a single therapy providing device 200 may be utilized for treatment according to the present invention, or multiple therapy providing devices 200 may be utilized for therapy. The two therapy providing devices 200 can be communicatively coupled together utilizing a physical connection or a wireless connection such as those described above.

Figure 2:
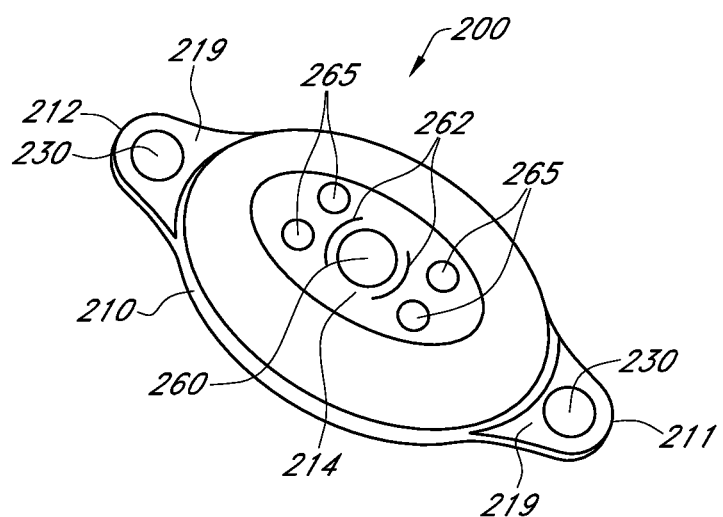
FIG. 2 is an isometric view of a therapy providing device in accordance with the present invention.

Referring now to FIG. 2, there is shown an isometric view of a therapy providing device 200. As shown in FIG. 2, the therapy providing device 200 includes a housing 210. The housing 210 defined by a proximal end 212 and a distal end 211, and first surface 214 and a second surface 215 (not shown), the proximal end, distal end and first and second surfaces and defining a volume therebetween, wherein the volume includes additional structures and components as will be described below. As shown in FIG. 2, the first surface 214 includes a power button 260, a LED indicator light 262, and at least one pair of charging pins 265. The multiple charging pins 265 may be including on the therapy providing device 200, whereas the multiple pins 265 are disposed symmetrically about an axis (not shown) passing through the power button 260. Placement of the charging pins 265 about an axis extending through the power button 260 allows for the therapy providing device 200 to be placed within a charger without care as to orientation as each side of the therapy providing device 200 includes charging pins 265, such that the therapy providing device 200 will engage the changing pins in the charging station in either orientation. Additional details with regard to a charging station/base will be described in greater detail below with reference to FIG. 11. Additionally, the housing 201 may further include magnets 230 or a metallic material disposed within recesses formed in the first and second ends 211, 212 of the housing 210. Alternatively, the magnets 230 may be integrally formed with the housing 210 during a manufacturing process such as injection molding.

The housing 210 may be formed of multiple pieces which may then be assembled using known assembly methods such as glue, ultrasonic welding, heat welding, rotational welding, snap-fit construction, use of fasteners such as screws or pins, or the like. In accordance with the invention, the housing 210 may be formed of two pieces or multiple pieces, wherein one section of the housing 210 includes all sides except the second surface 215, thereby forming a shell into which the components can be disposed, then the second surface 215 could be attached to the other portion of the housing 210 to form the therapy providing device 200. The housing 210 may be constructed of biocompatible materials such as polymers, plastics, fabrics or metals. The housing 210 may be formed using manufacturing processes such as machining, injection molding, 3-d printing, vacuum forming, deep drawing or the like. In accordance with the invention, the materials utilized in construction of the housing 210 of the therapy providing device 200 shall be chosen such that the materials have good biocompatibility as it is intended that the therapy providing device 200 will be placed in skin contact during use, where in certain usages the skin contact may be for prolonged time.

Further still, it is contemplated that the therapy providing device 200 may be wrapped with a biocompatible membrane. An example of a suitable membrane is available from 3M and sold under the tradename of TEGADERM.

Figure 3A:
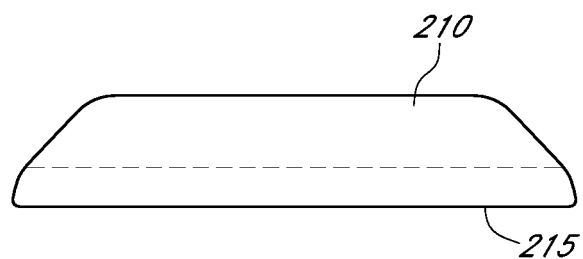
FIGS. 3A-3D are exemplary illustrations of housings of the therapy providing device in accordance with the present invention.
Figure 3B:
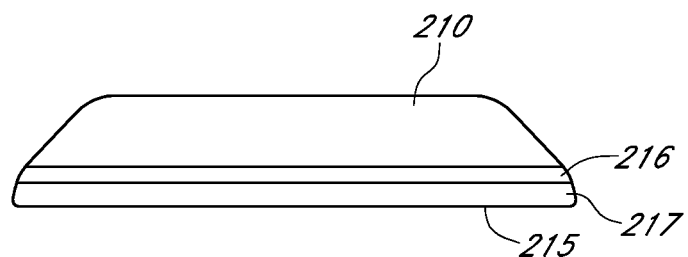

Referring now to FIGS. 3A-3D there are shown exemplary embodiment of the second surface 215 in accordance with the present invention. As shown in FIG. 3A, the second surface 215 may be formed as a planar surface. Referring now to FIG. 3B, in this figure, the second surface 215 is formed of multiple pieces, wherein one component 216 is configured to be received by the other portion of the housing and the second component 217 is configured to be received by a user's tissue, this portion 217 may be formed of a more pliable or conformable material than the first component 215, wherein the more pliable material 217 may conform or shape to the user's anatomy more readily. In accordance with the invention, the second component 217 may be formed of a compliant material such as and open or closed cell foam material, such that when the therapy providing device 200 is disposed upon a user for therapy, the compliant foam surface conforms to the user's anatomy. Additionally, the materials selected may be chosen such that they are anti-microbial/bacterial.

Figure 3C:
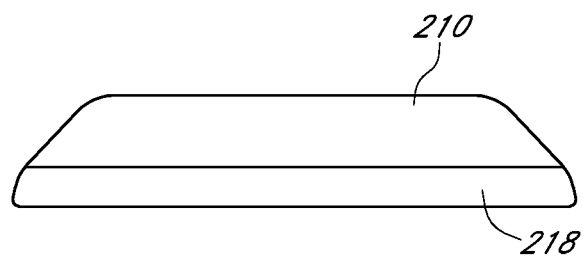
Figure 3D:
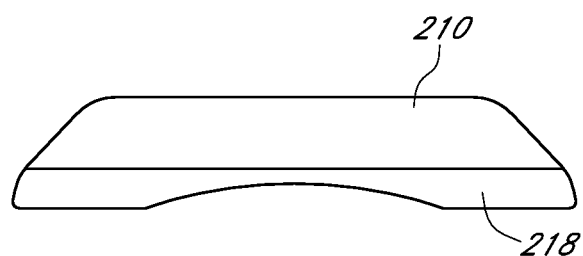

Referring now to FIGS. 3C and 3D there is shown another exemplary embodiment wherein the second surface 218 is shown having a first thickness, wherein the material of which the first surface 218 is formed is selected such that the material may be shaped or contoured to be received by a patient's skin, particularly in an area adjacent the patient's clavicle. The shaped surface may be in the form of a concave shape. Further still, the material 218 of FIGS. 3C and 3D may be selected such that the material defines a deformable structure, such that when the housing is placed over the patient's clavicle the housing conforms to the patient's anatomy as shown in FIG. 3D. In yet another embodiment, a portion of the housing may be custom formed to each individual user through the application of heat, whereby the housing or a portion of the housing is heated and then pressed onto the patient, the heated portion of the housing conforming to the patient's anatomy, or heated and molded by through an application of force. In another aspect, the second component 217 may be embodied in the form of a flexible membrane in which an expandable foam material may be injected into. In use, the therapy providing device would be placed on the user in a chosen location, the expandable foam material could then be injected into the flexible membrane while the therapy providing device is held against the user. As the foam expands and cures, the second component 217 would take the shape of the user's anatomy, thereby providing a customized fit. Lastly, it is further contemplated that the housing includes an enlarged or thickened surface that can be ground or machined away to conform to the patient's anatomy. Further still, a mold may be taken of the patient's anatomy, whereby a housing can then be manufactured from the mold taken from the user's anatomy, thereby customizing the fit of the therapy providing device to each user.

Figure 4A:
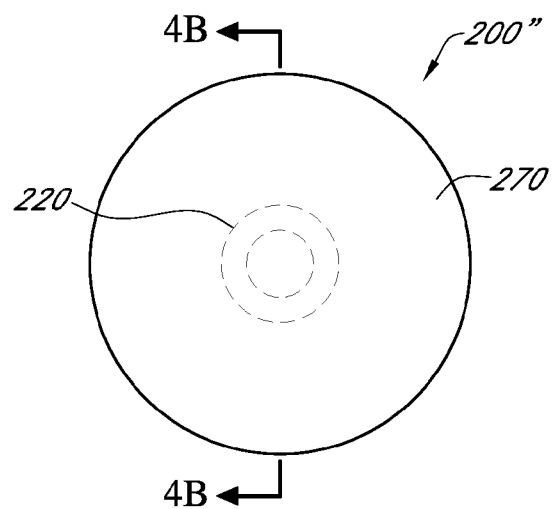
FIG. 4A is a top view of a housing of the therapy providing device in accordance with the present invention.
Figure 4B:
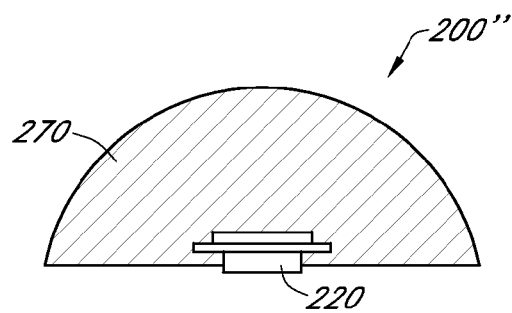
FIG. 4B is a cross-sectional view of the housing of FIG. 4A taken about line B-B.
Figure 4C:
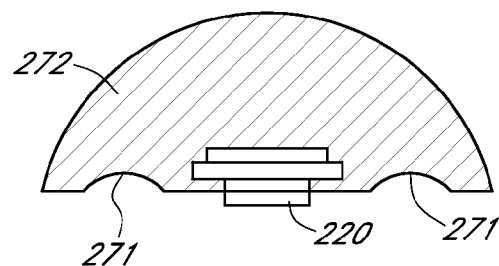
FIG. 4C is a cross-sectional view of another housing in accordance with the present invention.

Referring now to FIGS. 4A-C there are shown additional housing designs in accordance with the present invention. As shown in FIG. 4A the alternative housing is formed in a generally circular fashion, wherein the housing contains additional components as will be described in greater detail below. Also as shown in FIG. 4A, the housing 270 may further include a wire or cable connection extending from the housing 270 as described above. Referring now to FIG. 4B, there is shown a cross-sectional view of the housing 270 of the therapy providing device 200" of FIG. 4A taken about line B-B of FIG. 4A. As shown in the cross-sectional view, the alternative housing 270 is formed having a generally convex shape. Referring now to FIG. 4C there is shown a cross-sectional view of yet another alternative embodiment of a housing 272, in this embodiment the housing 272 has a generally convex shape as previously described, however, in this embodiment the housing 272 includes concave portions 271. In use, the housing 272 is placed on a user, adjacent to the user's clavicle, wherein a force can be applied to the housing 272 adjacent to each concave portion 271 forcing air out of the concave portions 271, thereby causing a vacuum to be formed thereby suctioning the housing 272 to the user's tissue. It is contemplated that the housings 270 and 272 shown in FIGS. 4A-4C may be constructed of a biocompatible flexible material, such that the housing conforms to the user's anatomy when placed thereupon. Examples of suitable materials of which the housings 270, 272 may be formed from are: silicone, urethanes, rubber, silicone, latex and the like.

Figure 5:
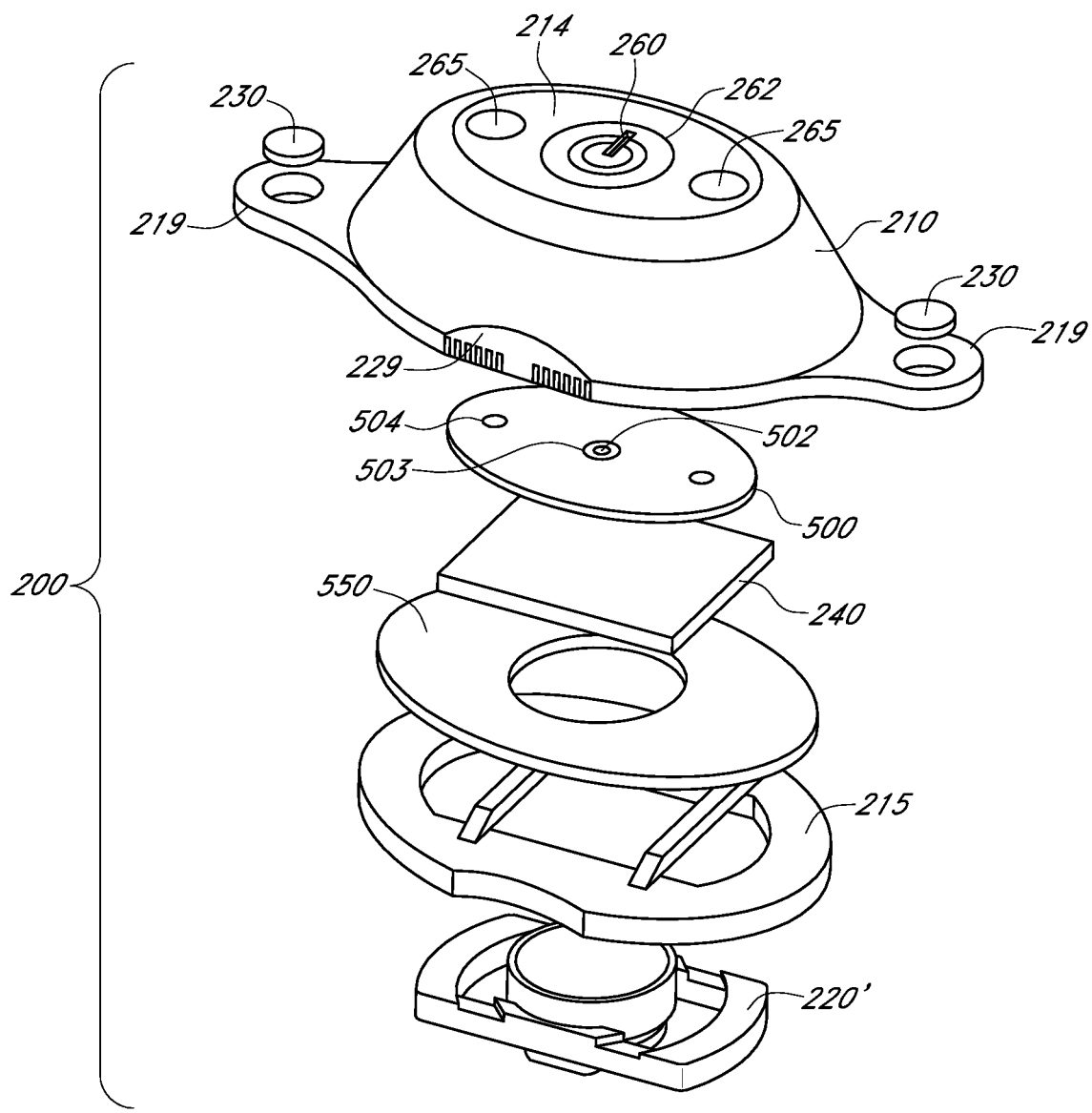
FIG. 5 is an exploded view of a therapy providing device in accordance with the present invention.

Referring now to FIG. 5, there is shown an exploded view of a therapy providing device 200 in accordance with the present invention. As described above and shown in FIG. 2-4, the therapy providing device includes a housing 210, wherein the housing includes provisions for a power switch 260 as well as provisions for LED indicators 262 and charging pins 265 as described above. The power switch 260 maybe a separate component disposed within the housing 210 or it may be embodied as a reduced thickness portion (not shown) of the housing 210 which can be formed to project slightly above the first surface 214 of the housing 210, whereby in use, a user can apply a light force to the raised portion to active a switch disposed beneath the raised portion. Forming a raised portion integral to the first surface of the housing 210 to be utilized as a switch simplifies construction, eliminates additional components, this construction also eliminates the need to form a hole within the first surface of the housing which may require sealing against liquids. Further, the provisions for the LED 262 and the charging pins 265 may be in the form of openings formed within the housing to receive such items. Alternatively, the LED 262 provision may be embodied in the form of an opaque or clear section within the housing 210 during manufacture to allow light to project therethrough from a LED 503 mounted on a circuit board 500 disposed below the housing 210. Additionally, it is contemplated that the charging pins 265 may also be integrally formed during the manufacture of the housing 210. For example, if the housing 210 is manufactured using an injection molding process, the charging pins 265 could be disposed within the injection mold as an insert, whereby the charging pins 265 would be captured in the housing 210 during the molding process. Alternatively, the housing 210 can include openings for charging pins 265 to project through. Further still, the housing 210 may include openings having tapered wall portions, forming pockets within the first surface 214, thereby providing access to charging pads/pins 504 disposed on a circuit board 500 disposed below the first surface 214 of the housing 210. The housing 210 may further include an indentation 229 formed therein or a plurality of indentations 229, allowing a user to grasp the housing 210.

As shown in FIG. 5, the therapy device 200 further includes a first circuit board 500 and a second circuit board 550. The first circuit board 500 is disposed adjacent to the first surface 214 of the housing 210, wherein the first circuit board 500 includes a power switch component 502, at least one indicator LED 503 configured to indicate the power status of the therapy providing device 200. The first circuit board 500 further includes charging pins/pads 504, wherein the charging pins/pads may be configured to project through the housing 210 as described above, or alternatively, the housing 210 may include openings formed therein to access the charging pins/pads 504. The power switch 502 may be embodied as a physical switch, such as a slide switch, or may be embodied as a touch sensitive or capacitive sensitive switch, or may be embodied as a pressure sensitive switch. The first circuit board 500 further includes a connector (not shown) which is configured to electrically connect the first and second circuit boards. The connector may be embodied as solder holes in which wires can be disposed into or may be embodied in the form of a plug or header assemble, wherein the plug/header are configured to accept a cable, wire, ribbon cable or a flexible pcb to facilitate electrical communication between the boards. The first and second circuit boards may be constructed of known materials and methods, whereby the boards may be hard rigid board assemblies or may be constructed using flexible board manufacturing technologies. Although, it is described above that the present invention utilizes two circuit boards, this should not be considered limiting in any manner, it is contemplated that the electronic components of the present invention may be embodied on a single circuit board or on multiple circuit boards.

As shown in FIG. 5, disposed below the first circuit board 500 is an energy source 240. The energy source 240 may be in the form of a battery pack. The battery pack may be a rechargeable pack or a single use pack which may be embodied as gel batteries or absorbed glass mat batteries. Suitable examples of batteries that may comprise the pack are lithium ion (Li-ion), lead-acid, nickel-cadmium (NiCd), nickel-zinc (NiZn), zinc-oxide, nickel metal hydride (NiMH), Lithium ferrous-oxide (LiFo) or other known battery technologies. It is further contemplated that instead of utilizing a battery for an energy source a capacitor and related circuitry could be utilized.

In the event that the energy source 240 is embodied as a battery pack, the battery pack may be embodied in the form of a fabricated pack, where individual cells are soldered together, or alternatively, the battery pack could be arranged to utilize conventional battery sizes such as AAA, AA, CR2032, LR44, 9-volt, A23 and the like.

It is further contemplated that the battery pack may be further divided into a primary battery pack and a backup battery pack. In use, the primary battery would be initially utilized, if the pack malfunctions or loses its charge or its charge is used, the backup battery pack would then be enabled to continue the therapy.

If the battery pack as described above is chosen to be a rechargeable, there is a need to provide a charging circuit within the circuit boards 500 or 550. The charging circuit may utilize either a physical connection to enable charging or may use a non-contact or inductive charging arrangement. If a physical connection is utilized, the plug may be a USB style plug, headphone style, spring loaded pins/contact pads or other types of plugs, such a plug can be integrated into the housing 210 and electrically connected to the battery through either circuit board. Alternatively, a plug may be directly mounted onto one of the circuit boards. It is further contemplated that the charging plug can also be utilized both for charging as well as communication between multiple therapy providing devices 200 or the computing module 300 as described above using a compatible cable.

As described above, the present invention may utilize pins or pads disposed on or coupled to the first circuit board to enable charging of the battery disposed within the device. It is further contemplated that a non-contact charging assembly could be utilized with the present invention. If a non-contact charging arrangement is selected, then the charging pins 265 and/or openings within the first surface of the housing 210 may not be necessary. Instead, the therapy providing device 200 would include a charging coil (not shown) disposed about the perimeter of the first circuit board 500. The use of a non-contact charging coil would further necessitate the inclusion of additional integrated circuits to enable and control the charging function. These additional circuits can be disposed on either of the two circuit boards. Suitable examples of a non-conductive or inductive charging would utilize an electromagnetic field to transfer energy between the charger and the battery pack. In this embodiment a charging station would be provided in which the therapy providing device 200 could be stored and charged simultaneously as will be described below. It is also contemplated that the storage/charging container may be a smart container that is it may contain a microprocessor and/or a wireless communication chipset. Thus, once the therapy device is removed from the storage container, the integrated wireless chipset within the storage container may cause the therapy device to power on. Suitable examples of components to enable non-contact charging are available from Wurth Electronics Inc., part numbers 760308201 wireless charging receiving coil and 760308101 wireless charging transmitting coil.

In accordance with the present invention, it is contemplated that the energy source 240 may be embodied in the form of an integrated generator, wherein the generator would be configured to create energy from movement of the therapy providing device 200, much like and automatic watch movement.

Figure 6:
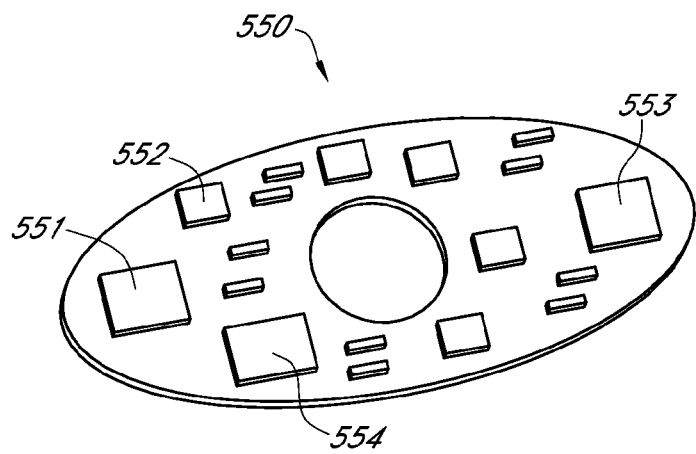
FIG. 6 is an isometric view of a circuit board in accordance with the present invention.

As described above, the therapy providing device 200 shown in FIG. 5 includes two circuit boards, 500 and 550. The circuit board 500 having been previously described above. Referring now to FIGS. 5 and 6 there are shown exemplary embodiments of the circuit board 550 in accordance with the therapy providing device 200 of the present invention. As described above, the second circuit board 550 is configured to be coupled with the first circuit board 500, wherein components may be disposed on either of the two boards and interconnected through an appropriate connection as previously described using a header or solder holes formed in the circuit board 550. Referring now to FIG. 6, there is shown a general schematic of the second circuit board 550, wherein the second circuit board 550 includes a processor 551, optional memory chip 552, an audio amplification circuit 553 and a communication port 554. The communication port 554 may embodied as a physical port such as a mini-usb, micro-usb, firewire, thunderbolt or other known similar communication ports. The audio amplification circuit 553 may include one or two audio amplifiers, wherein the incoming signal from the processor 551 is amplified such that the amplified signal can then be connected to a driver assembly 220 as described below. As shown in FIGS. 5 and 6, the second circuit board 550 may be shaped to be received within a shaped housing. As shown in FIGS. 5 and 6, the second circuit board is shown having an elliptical shape with an aperture formed through the center thereof. The aperture can be sized to receive a portion of the driver assembly 220, thereby allowing the overall size of the device to be reduced by allowing components to 'nest' when assembled. The second circuit board 550 may contain additional electronic components such as audio filters, booster circuits, timing circuit and data logging capability. In accordance with the present invention, the processor 551 may be sourced from CSR PLC, Churchill House, Cambridge Business Park, Cowley Road, Cambridge, CB4 0WZ Churchill House, Cambridge Business Park, Cowley Road, Cambridge, CB4 0WZ, having part number 8670.

The second circuit board 550 may further include a communications chipset (not shown) such: BLUETOOTH, WIFI, ZIGBEE, RFID, NFC, Ant+, infrared, 3G/4G, CDMA, TDMA or other known wireless communication protocols.

The first or second circuit board 500/550 may further include a clock circuit (not shown). The clock circuit generates and sets the timing of operations performing within the therapy providing device 200. The clock generator may be utilized to activate the therapy providing device 200, or may be utilized to record timed events, such as when the therapy providing device is on or off or in use.

Further still, either circuit board 500/550 may alternatively include an impedance sensor or pair of impedance sensors, the impedance sensors in association with the processor 551 can be used to determine if the housing 210 is coupled to a user's skin or if the housing is not coupled to the skin. If the housing 210 is coupled to a user's skin, then the impedance sensor would provide a signal to the processor 551 indicating such a condition, thereby the program stored in the memory of the processor or transmitted to the microprocessor could be initiated to conduct therapy according to the invention. If the impedance sensor is not coupled to the user's skin, then an open condition would occur, whereby the program would not be initiated and a visual signal may be generated through the program/processor to alert the user that the therapy providing device 200 is not placed properly and needs to be repositioned.

In yet another embodiment, the electronics module may include a microphone, whereby a test signal can be initiated and delivered by the driver assembly 220 or other audio/vibration device. The microphone would be utilized by the processor 551 to listen for a reflection of the test signal off of the user's clavicle, skin or other bone or structure to determine if the therapy providing device 200 has been placed properly. If the reflected sound matches that of one stored in memory, then the program can be run to provide therapy. If the reflected sound does not match the sound stored in memory, then an error message would be generated. The error message may be in the form of an audio signal or in the form of a visual signal such as a blinking light or a series of blinking lights.

Additionally, the microphone could be coupled with a blood pressure monitor, wherein the microphone would listen for Korotkoff sounds, whereby the data generated from the blood pressure monitor and specifically the Korotkoff sounds captured by the microphone can be utilized to enable a closed loop control system or closed loop feedback system. It is contemplated, that the therapy provided by the therapy providing device 200 can be dynamically modified in response to the data received from the microphone coupled to the processor 551.

The circuit board 500 or 550 may further incorporate a pressure sensitive switch coupled to the processor 551. In use, the pressure sensitive switch would be in a normally open position or off position. When the therapy providing device 200 is placed on the user's skin, the pressure sensitive switch would be depressed, thereby turning the therapy providing device 200 on. The actuation of the switch can also be associated with the clock circuit to associate a time with the on/off state of the switch. These events can be written to the memory of the processor 551 or other memory storage location. The data can then be transmitted, wired or wirelessly, to a personal computer for analysis/storage. By tracking the actual on/off time of the therapy providing device, user compliance may be tracked by the user or by a third party such as a health care provider.

In yet another embodiment, the circuit board 500 or 550 may include an optical sensor, wherein the optical sensor is utilized to detect whether the therapy providing device is affixed to a user's skin. In this embodiment, the optical sensor can include a light sensor, whereby when the therapy providing device 200 is affixed to the user's skin the light is blocked to the sensor. In another embodiment, the optical sensor can be a reflective sensor, wherein the color of the light reflected back indicates whether the device is affixed to a user's skin or not.

In another aspect of the present invention, the light sensor may be utilized to monitoring blood oxygen level, wherein data received from monitoring the user's blood oxygen level can be stored in memory or transmitted to another device such as a pulse-oximetry monitor or another computing device. Further still, the blood oxygen data may be utilized by a program of the therapy providing device to alter therapy provided to the user or otherwise control the therapy providing device 200.

In another aspect of the present invention, the light sensor may be used to measure alteration in blood-reflectance color, whereby the program controlling the therapy providing device may utilize this signal as a representation of heart rate or heartbeat. Accordingly the program controlling the therapy providing device 200 may use this data to determine blood pressure and accordingly provide therapy to the user based on the received data.

It is further contemplated, that an accelerometer and/or compass and/or tilt sensor and/or GPS sensor can be incorporated into either of the circuit boards described above. The inclusion of such a sensor can be utilized to determine the position and/or orientation of the device. In use, as described below, a user would affix the housing 210 to their person using an adhesive patch, harness, specialized clothing article as will be described below. In this embodiment, the accelerometer/compass in communication with the processor 551 can be utilized to determine when to activate the therapy providing device or devices 200. If the signal coming back from the accelerometer/compass/tilt sensor indicates that a therapy providing device 200 is in a vertical position, then the program contained within the memory of the processor 551 or computing device 800 would not be initiated. Once the signal from the accelerometer/compass/tilt/GPS sensor indicates that the user is in a prone position, likely a sleep position, then the program contained within the memory can be run. Additionally, the clock timer can be associated with the accelerometer/compass/tilt/GPS sensor such that a user's sleep pattern can be stored in memory of the processor 551 or computing device 800. Data generated from such sensors could be stored in memory, of either the therapy providing device or the computing device to track usage of the device as well as the physical location of the devices. Such data could be transmitted to a third party using know wireless communication methods.

The circuit boards or the housing or therapy providing device 200 may be provided with a unique identifier such as a serial number or patient information identifier so that the therapy providing device 200 may be tracked. Additionally, using the unique identifier it may be possible for a physician or a user to utilize a computer program, such as a website which when placed in communication with the therapy providing device, either wired or wirelessly, would allow continuous monitoring of usage of the device, such as date and time monitoring, duration of use, patient compliance and the like. The website could also provide information regarding hypertension and additionally be configured to communicate with other devices such as a scale to track the user's weight, a blood pressure monitor to track blood pressure measurements, a glucose meter, a heart rate monitor or other fitness tracking device such as FITBIT or BODYBUG. Each of these devices would be interfaced with the website, such that data collected from these devices could be uploaded to the website where the data could be presented to the user or alternatively, the data could be shared with anyone that the user chooses to do so. For example, the user may desire to share the data with their health care provider, dietician or other individual(s).

In accordance with the invention, it is contemplated that one or both circuit boards along with the battery may be housed within a separate housing from the therapy providing device 200. In this embodiment, the circuit board(s) and battery would be coupled to the therapy providing device either through a cable connection or through a wireless connection. If a wireless connection is utilized, then the therapy providing device would include the necessary electronics disposed within its housing to facilitate the communication between the electronics module and the therapy providing device as well as a power source such as the battery.

Figure 7:
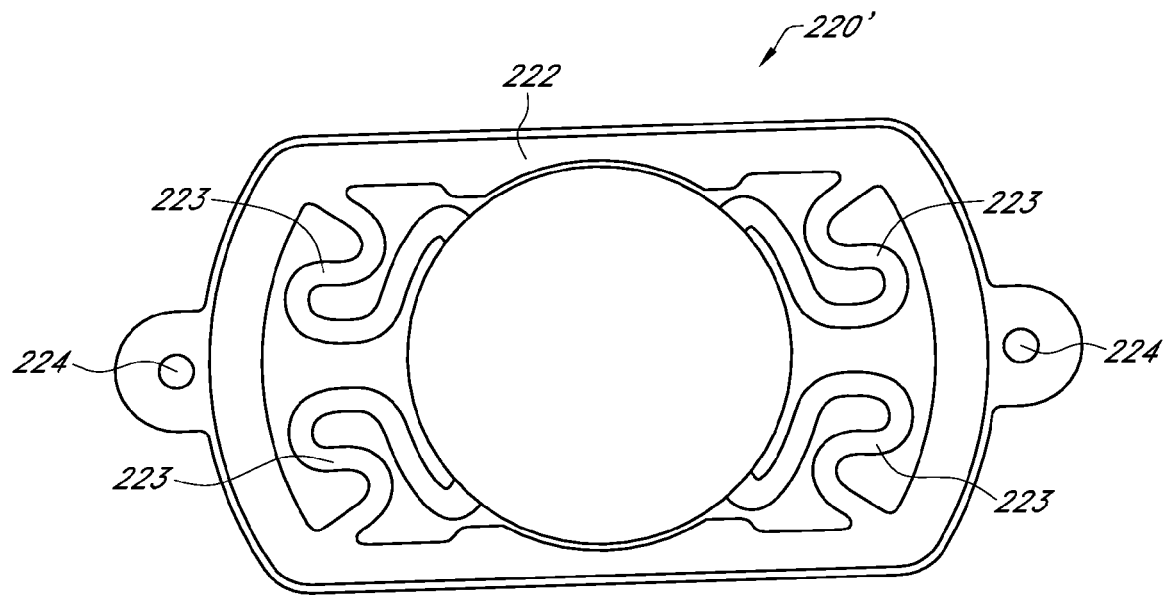
FIG. 7 is a plan view of a haptic speaker in accordance with the present invention.

Referring to FIG. 5, disposed below the second circuit board 550 is a driver assembly 220. The driver assembly 220 is disposed within the volume 213 of the housing 210. The driver assembly may comprise a conventional coil speaker, an ultrasonic generator, a piezoelectric speaker, a haptic speaker, a pneumatic device, a suction device, a mechanical vibratory device, a hydraulic actuation device, or a photo-acoustic excitation device. Examples of drivers assemblies 220 that can be used with the present invention may be purchased from HiWave Technologies PLC, Regus House, 1010 Cambourne Business Park, Cambourne, Cambridge CB23 6DP United Kingdom. Referring now to FIG. 7 there is shown an exemplary haptic speaker or haptic exciter 220' which may be utilized with the therapy providing device 200 of the present invention. As shown in FIG. 7, the haptic speaker 220' includes a frame member 221, a voice coil 222 and a plurality of flexible members 223. Additionally, the haptic speaker 220' includes electrical connections 224, thereby allowing the haptic speaker 220' to be electrically connected to the audio amplifier circuit as previously described. In use, the flexible members 223 allow the voice coil 222 of the haptic speaker 220' to translate relative to the frame 221, thereby producing sound or movement.

Figure 8:
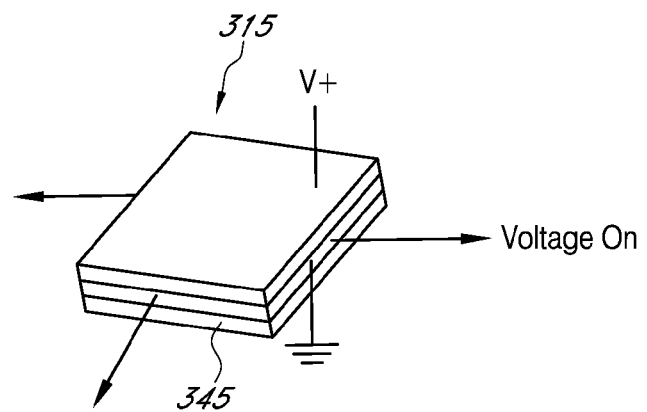
FIG. 8 is an isometric view of an electroactive polymer transducer in accordance with the present invention.
Figure 9:
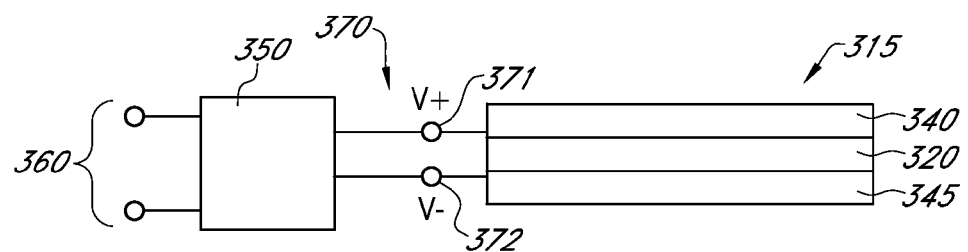
FIG. 9 illustrates a cross-sectional view of the electroactive polymer transducer of FIG. 8 in communication with a driver.
Figure 10:
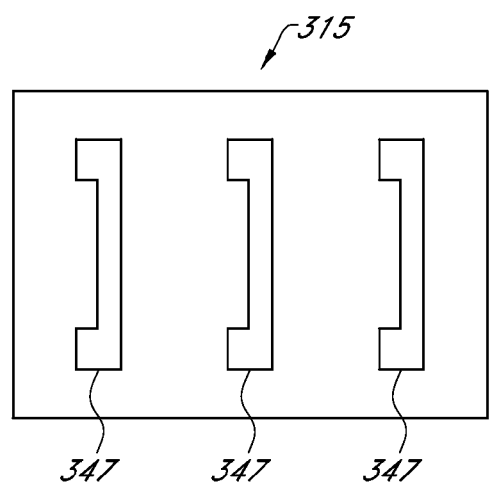
FIG. 10 is a plan view of an alternative embodiment of an electroactive polymer transducer in accordance with the present invention.

In yet another embodiment, the driver assembly 220 may be embodied as an electroactive polymer transducer 315 as shown in FIGS. 8-10. Electroactive polymer transducers are made up of a first thin elastic polymer 320, which is also referred to as a film or membrane, this is sandwiched between compliant electrodes 340 and 345. When voltage is applied across the electrodes, the unlike charges in the two electrodes are attracted to each other, these electrostatic attractive forces compress the polymer film 320 (along the z-axis). The repulsive forces between like charges in each electrode stretch the film in the plane (along the X and Y axis'). As the transducer 315 deflects, the deflection can be utilized to perform work. In the present invention, the work that is performed is the development of vibrations, wherein the vibrations being developed by the transducer 315 are developed within a certain frequency range as will be discussed in greater detail below. Additional information regarding electrostatic transducers can be found in U.S. Pat. No. 7,898,159 and U.S. Pat. No. 7,608,989, the entireties of which are hereby incorporated by reference.

It is further contemplated that the transducer 315 as described above may be further coupled to another assembly, wherein the other assembly would have an increased mass. Through use, the transducer would be activated by providing a voltage to the electrodes, thereby exciting the polymer, wherein the weighted assembly would be excited thereby delivering greater vibrational energy.

In accordance with another aspect of the present invention, the electroactive polymer transducer 315 can be formed to have a curved shape, or be attached to a housing having a curved shape, such that the housing or curved excited can be readily received by a user's anatomy, specifically the user's clavicle or collarbone.

The electroactive polymer transducer 315 of the present invention may be embodied in different geometric shapes. It is contemplated that the transducer 315 may be embodied in the form a circular shape, oblong shape, square, rectangular or other known geometric shapes. Further still, it is contemplated that the transducer may be formed with at least one bar-arm type of arrangement as shown in FIG. 3D. In this embodiment, the bar-arm 347 is configured to vibrate in response to the charge placed on the electrodes. The number of bars and shape of the bars can be configured to adjust the acoustic/vibrational properties of the assembly.

Use of an electroactive polymer transducer as described above further includes a circuit driver 350, the circuit driver 350 may be incorporated into the first or second circuit boards 500/550 as described above. Alternatively, the circuit driver 350 may be embodied as a separate circuit board (not shown) which may be electrically coupled with either the first or second circuit boards of the present invention. The circuit driver 350 further includes an audio input 360 and at least one output 370, but preferably a pair of outputs 371 and 372. The outputs 371, 372 are coupled to the electrodes 340, 345 of the transducer 315.

The circuit driver 350, may further include additional components such as an amplifier, a filter, a voltage step-up circuit, a charge controller, voltage step-down.

Further still it is contemplated that the driver assembly may be embodied as multiple elements, for example any combination of driver assemblies may be use, such as a combination of a haptic speaker and a piezo, a haptic speaker and an electro active polymer transducer, an electroactive polymer transducer and a piezo or multiples of the same driver type within the same housing. The examples provided herein should not be considered limiting in any manner. Alternatively, the driver assembly may be a vibrating motor or coin cell motor.

As described above and in accordance with the present invention, it is contemplated that two therapy providing devices 200 may be utilized together to provide therapy to a user, wherein the two therapy units may be interconnected with a physical connection. It is contemplated that one of the therapy devices may have a complete set of electronics disposed therein, wherein the complete set of electronics would include the communication, memory and other chipset(s) and associated circuitry. Wherein the other therapy providing module 200 could then include a simplified electronics module, wherein the simplified electronics module would not have the complete chipset of the complete electronics module. For example, the simplified electronics module would not need to have a battery charging circuit or other chips as well it may have less or no memory. By providing the other therapy providing device with a slimmed down electronics module a larger energy source may be fitted, through this arrangement the combined therapy providing devices 200 could be utilized for a longer time before the energy source would need to be replaced or recharged.

Figure 11:
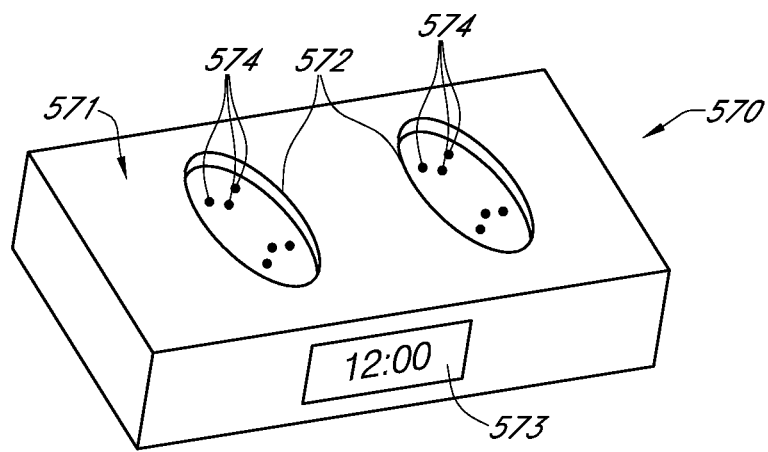
FIG. 11 is an isometric view of a charging/base station in accordance with the present invention.

Referring now to FIG. 11 there is shown a charging/base station 570 in accordance with the present invention. As shown in FIG. 11, the base station 570 includes a housing 571, wherein the housing 571 includes recessed portions 572 configured to receive the therapy providing device 200 therein. The recessed portions 572 are configured to include charging pins 574, which when the therapy providing device 200 is disposed within the recess will align with the charging pins/pads 265 of the therapy providing device. In addition to the charging pins 574, other pins may be included both on the base 570 and the therapy providing device 200 which may be used for other purposes such as downloading data stored within memory of the therapy providing device(s) 200. The base station 570 may further include a wired or wireless connection to the internet or other network such that the data received from the therapy providing device(s) can be transmitted or uploaded to a webpage as described above or transmitted to another location such as a health care provider or other location for storage. It is further contemplated that the base 570 may include additional features such as an alarm clock or clock 573, a cellular telephone or tablet charging station. As will be described in greater detail below with regard to FIGS. 16A and 16B, the therapy providing device may include extensions 219 extending from the housing 210 each extension 219 containing a magnet 230. It is contemplated that the recessed portions of the charging base 570 may be shaped to receive the extensions 219 of the housing 210 shown in FIG. 16A. The recessed portions 572 may be adapted to receive the extensions 219 or may further include a metallic member or a magnet disposed therein, such that when the therapy providing device is placed into the recessed portion, the magnets 230 within the housing 210 of the therapy providing device 200 are attracted to the metal or magnet of the charging station 570, thus, temporarily affixing the therapy providing device 200 to the charging station. In addition to temporarily affixing the therapy providing device 200 to the charging station 570, by temporarily affixing the therapy providing device 200 to the charging/base station 570 providing better contact between the therapy providing device 200 and the charging pins 574. It is contemplated that other arrangements to increase contact between the therapy providing device and the charging pins of the charging/base station may be utilized. For example, the charging pins 574 in the base station 570 may be configured to move linearly and be held with a spring force, whereby the charging pins 574 retract or partially retract when a therapy providing device 200 is placed into the recessed portion 572 for charging. Additionally, another member (not shown), such as a plate or weights may be placed onto the therapy providing devices after the therapy providing devices have been disposed within the recessed portions. Further still, the charging pins 574 may be disposed on a lid (not shown) of the charging base 570, such that the therapy providing device 200 is placed within a recessed portion 572 of the charging base 570 and the lid is closed, thereby completing the electrical connection between the charging pins 574 of the charging base and the charging pins/pads 256 of the therapy providing device 200.

In accordance with the invention, the base 570 may be further embodied as another medical device or incorporate other medical devices. It is contemplated that the base 570 may incorporate, or be incorporated into another medical device such as a pulse-oximetry meter, a blood pressure monitoring device, a glucose meter, an infusion pump, a glucose pump, sleep tracking device, temperature measuring device, or a sleep apnea device such as those offered by ResMed and Respironics. Presently, sleep apnea devices utilize a console which houses the electronics necessary to control a blower to deliver pressurized air to a patient interface. The patient interface may be embodied in the form of a full-face mask, nasal mask, oro-nasal mask, mouth mask, nasal prongs, or other suitable configurations know in the art. Also, any suitable headgear arrangements may be utilized to comfortably support the patient interface in a desired position.

Figure 12:
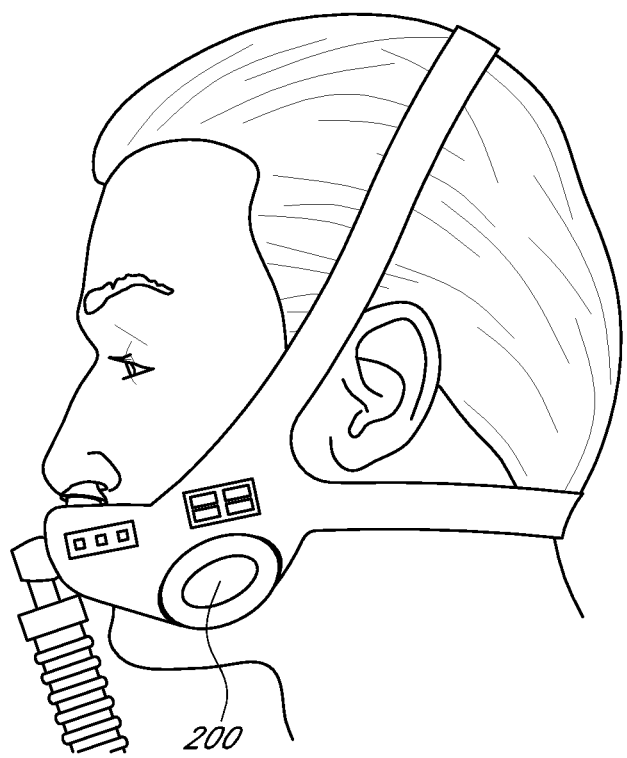
FIG. 12 is a side view of the therapy providing device of the present invention in combination with a CPAP mask assembly.

In yet another aspect of the present invention, referring now to FIG. 12 there is shown the therapy providing device 200 of the present invention, wherein the therapy providing device 200 has been adapted to interface with a sleep apnea patient interface. As shown in FIG. 12, the therapy providing device 200 is configured to be received or engage or is integrated into the headgear arrangement of a sleep apnea patient interface device, wherein the therapy providing device of the present invention is configured to engage the patient's jawbone or skull.

In yet another aspect of the present invention, the therapy providing device 200 may be incorporated into other devices which are configured to engage a patient's tissue and skeletal bones such as bone conduction hearing aids, one such example is being offered by Sonitus Medical under the tradename SOUNDBITE.

Referring now to FIGS. 13A, 14A, 14B, 15A, 15B, 16A and 16B there are shown multiple embodiments of the housing 210 of the therapy providing device 200 in accordance with the present invention. As shown in these figures, the housing 210 is shown having a variety of mounting assemblies that can be utilized to affix the therapy providing device 200 to the patient.

Figure 13A:
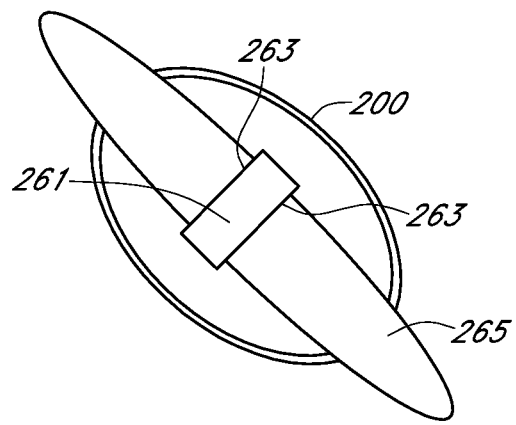
FIG. 13A is a bottom view illustrating a therapy device including an adhesive mounting system.
Figure 13B:
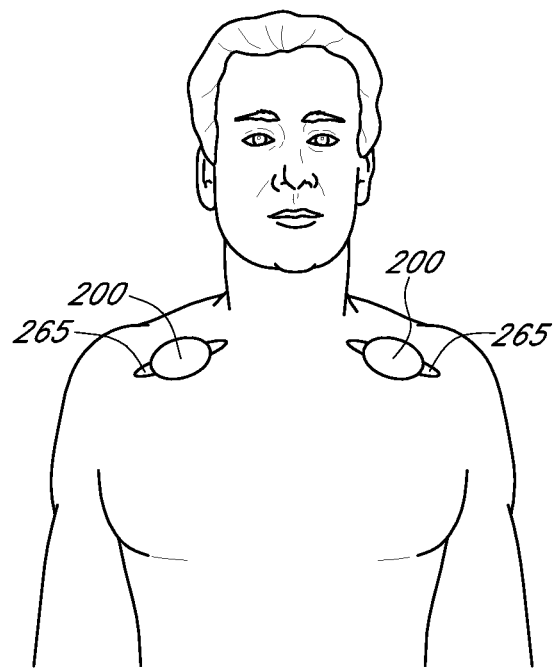
FIG. 13B illustrates the therapy device of FIG. 13A as disposed on a user.

As shown in FIG. 13A, one surface of the therapy providing device is provided with a slot 263. A bandage 265 can be passed through the slot 263, wherein a rib 261 formed by slot 263 retains the therapy providing device 200 onto the bandage 265. The bandage 265 further includes a biocompatible adhesive, such that the therapy providing device 200 can be affixed to the patient as shown in FIG. 13B. The bandage may be a one-time use construction, wherein the bandage is disposed of after a single use. Alternatively, the bandage 265 may be a multiple-use product, wherein the biocompatible adhesive is selected such that the bandage can be placed and removed from a user's skin multiple times. Additionally, it is contemplated that the biocompatible adhesive may be renewed. The adhesive may be renewed by spreading new adhesive over the existing adhesive, washing the adhesive surface with a substance to renew the surface or the adhesive may be embodied having multiple thin layers, wherein the user removes the used layers and disposes of the used layer, thereby exposing a new layer of adhesive for use again. A suitable example of an adhesive for a reusable bandage are hydrogel adhesives, similar to those utilized on electrodes for electrical muscle stimulation devices, otherwise known as a TENS unit. Such electrodes are manufactured and sold by 3M as well as others. It is contemplated, that a temporary marking may be applied to the user's body initially to indicate the location of where the therapy providing device. For example, the temporary marking may be in the form of a temporary tattoo or a henna tattoo.

Alternatively, a bandage large enough to cover the entire housing of the therapy providing device 200 may be utilized. In this embodiment, the bandage would hang over the edge of the housing by a sufficient amount, such that when the therapy providing device 200 is placed against the tissue of the user, the bandage could be affixed to the tissue to hold the therapy providing device in a desired position. In this embodiment, the bandage may include an aperture, an opaque section or otherwise transparent section, such that when the bandage is placed over the therapy providing device 200, the button 260, LEDs 262 and charging pins/ports 265 on the top surface of the housing 210 of the therapy providing device 200 described above are visible and accessible if the housing includes such components. Such a bandage may be constructed to further include a one-way membrane, wherein moisture under the bandage may be transported or migrate from the tissue surface through the bandage, however, the bandage would not allow fluid to pass from the outside to the therapy providing device 200 or the user's tissue.

Figure 14C:
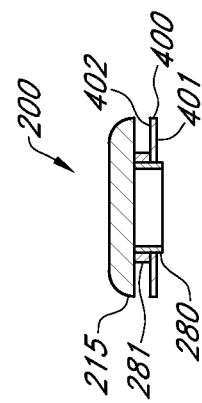
FIG. 14C is a cross-sectional view of the mounting system of FIGS. 14A and 14B.
Figure 14B:
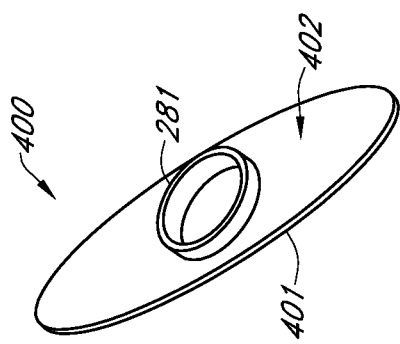
FIGS. 14A and 14B illustrate an alternative mounting arrangement for the therapy device of the present invention.
Figure 14A:
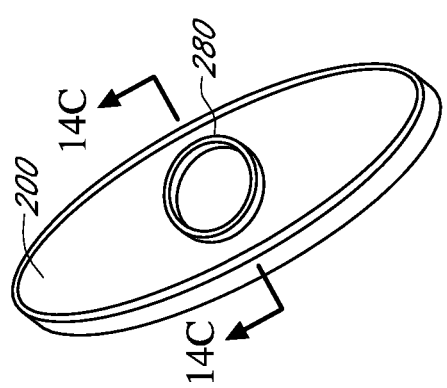

Referring now to FIGS. 14A-14C there is shown an alternative design for affixing the therapy providing device 200 to the patient. In this embodiment, one surface of the therapy providing device includes a first fitting 280 disposed on the second surface 215 of the housing 210. A bandage 400 is provided, wherein the bandage 400 has a proximal surface 402 and a distal surface 401. A biocompatible adhesive is disposed on the distal surface of the bandage 401. A second fitting 281 is disposed on the proximal surface 402 of the bandage 400. The first fitting 280 and the second fitting 281 are designed to be received by each other and to form a detachable locking attachment as shown in FIG. 14C. Suitable examples of such detachable fittings may be a screw thread, quarter turn fasteners, grooved pathways, a tapered fitting and the like. A safety lock (not shown) may be incorporated into either of the fittings, wherein the safety lock would engage after the two fittings are brought together in a locking arrangement. The safety lock would prevent the fittings from releasing without an additional application of force or motion to the safety lock to enable the fittings to be separated. The bandage 400 may be a single use product or may be a re-usable bandage as described above. In another aspect, the bandage of the present invention may be fabricated to include multiple layers, wherein each layer includes a new glue surface. After use, the layer of the bandage having been in contact with tissue is peeled off by the user and properly disposed of, thereby exposing a new glue layer for further use.

Figure 15B:
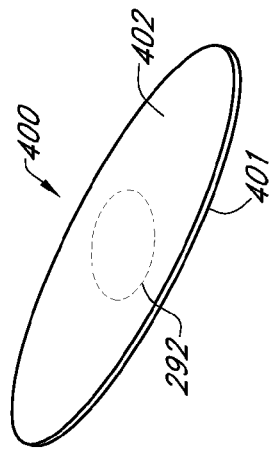
FIGS. 15A and 15B illustrate another mounting arrangement for the therapy device of the present invention.
Figure 15A:
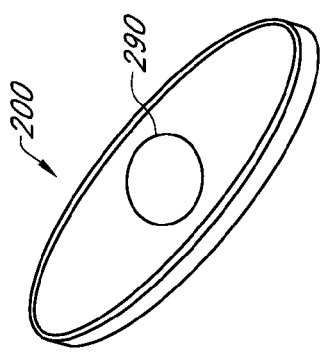

Referring now to FIGS. 15A and 15B there is shown another alternative design for affixing the therapy device 200 to a patient. In this embodiment, a surface of the therapy device 200 includes a magnet 290 disposed thereon or incorporated into the surface. As described above bandage 400 is provided, wherein the bandage 400 has a proximal surface 402 and a distal surface 401. A biocompatible adhesive is disposed on the distal surface of the bandage 401. A metallic member 292 is incorporated into the bandage 400 as shown in FIG. 15B. In use, the user would apply the bandage 400 to their body, wherein the center of the bandage would align with their clavicle. In one embodiment, the bandage 400 would be replaced daily. In another embodiment, the bandage 400 would be reused for a period of time and then replaced. Further still, in another embodiment, the glue surface of the bandage 400 may be refurbished after each use to prolong the useful life of the bandage 400. Once the bandage 400 is affixed to the user, the therapy providing device 200 as shown in FIG. 15A and described above would then be coupled to the bandage through the magnetic coupling between the magnet 290 of the therapy providing device 200 and the metallic member 292 of the bandage 400. It shall be understood that the combination of using a magnet 290 and a metallic member 292 could be reversed. For example, the bandage 400 may contain the magnet 290 and the therapy providing device 200 would have the metallic member 292. Alternatively, both the bandage 400 and the therapy providing device 200 may include a magnet 290, whereby the magnets 290 assist in self-aligning the therapy providing device to the bandage 400. Further still, it is contemplated that the magnet or metallic member of either the bandage 400 or the therapy providing device 200 may be offset from an axis extending through the center of the bandage 400, thereby providing for two different orientations in which the therapy providing device 200 may disposed upon the bandage 400 in for use. Further still, it is contemplated that the driver 220 of the therapy providing device may be offset within the housing 210 from an axis running longitudinally through the housing 210. Offsetting the driver 220 within the housing 210, achieves the same effect of providing multiple mounting orientations of the therapy providing device 200 during use. In yet another embodiment, the magnet 290 or metallic member 292 could be implanted under the user's skin, therefore eliminating the need for the bandage 400. In this embodiment, the therapy providing device 200 could be coupled to the patient's skin directly.

In another embodiment (not shown) the bandage may include an aperture formed therethrough, wherein the metallic member 292 would be disposed about the aperture. The aperture is sized to receive a portion of the therapy providing device 200 therein. It is further contemplated that the therapy providing device may include a second bandage or an enlarged surface similar in size to the bandage 400. The enlarged surface would contain magnets 290 as described above; therefore, when the therapy providing device 200 is disposed within the aperture of the bandage 400, the enlarged surface covers the bandage.

In further embodiments, the magnets and the metallic members may be interchanged, wherein the bandage contains the magnets and the housing may be a metallic member, a portion may be metallic or a portion may be magnetic. Additionally, instead of utilizing magnets and metallic members, other known detachable systems may be utilized, for example a hook and loop configuration or reusable adhesive surface.

Figure 16B:
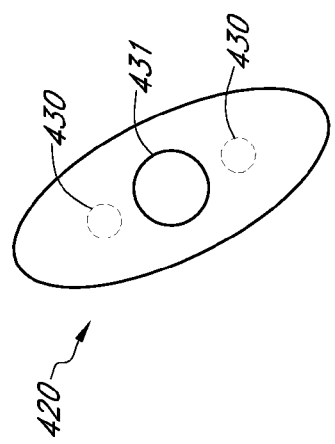
FIGS. 16A and 16B illustrate a magnetic mounting system in accordance with the present invention.
Figure 16A:
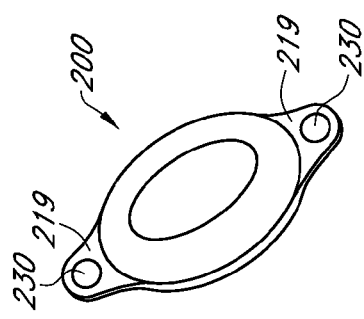

Referring now to FIGS. 16A and 16B there is shown a housing in accordance with the present invention, wherein the housing 210 includes extensions 219. The extensions 219 further include magnets 230 disposed therein. Referring now to FIG. 16B there is shown a bandage 420 to be utilized with the housing shown in FIG. 16A. The bandage 420 further includes an aperture 431 formed therethrough, the aperture sized to accept a portion of the therapy providing device 200. The bandage 420 further includes magnets 430 disposed therein. The bandage 420 may be formed of a multilayer construction, wherein the bandage may include a glue layer a glue support layer and a backing layer. It is contemplated that the magnets 430 could be disposed within the glue support layer, wherein the magnets 430 would be encapsulated in the bandage 420 by the glue layer and the backing layer. In use, the user would place the bandage 420 onto their skin, wherein the user can use the aperture 431 to properly align the bandage in the example where the therapy providing device is placed over the clavicle. The glue layer of the bandage 420 may be a re-usable adhesive, such as that described above and commonly utilized on tens electrodes, wherein the glue layer allows for repositioning of the bandage. After placement of the bandage 420, the therapy providing device, having a housing shown in FIG. 16A is disposed over the bandage. The magnets 230 of the housing extensions 219 and the magnets 430 of the bandage act to attach and center the therapy providing device to the bandage. In accordance with the invention, it is contemplated that either the magnets 230 of the housing or the magnets 430 of the bandage may be replaced by metallic members.

In yet another aspect of the invention, as described herein the magnets, which may be positioned in the device housing, the bandage or both, may be utilized to control the function of the therapy providing device 200. In this example, at least one of the magnets can be used as a switch to control or complete a power circuit. The power circuit can be activated such as to power the therapy providing device 200 on, thereby initiating therapy. If the magnetic connection is broken, then the therapy providing device would be powered off. It is further contemplated, that in addition to the above, the magnet within the device or bandage may be manufactured with specific properties, such that the therapy providing device will only operate with original equipment manufacturing products, thereby preventing the therapy providing device 200 from being utilized with non-approved or counterfeit bandages. A benefit of utilizing the magnets to switch the device on/off is that the user does not have to activate any buttons on the device, additionally, the device can be simplified through the eliminate of the button on the therapy providing device as described herein. Another benefit is the preservation of battery life of the device, as the device will be powered off as soon as the magnetic connection is broken. Additionally, if the therapy providing device is being utilized at night time during sleep and the device becomes dislodged from the user, the device will automatically power off, thus providing an additional safety feature.

Further still, it is contemplated, that the therapy providing device 200 and/or bandage may include a security feature, such as an optical scanner disposed within the therapy providing device, such that the optical scanner is configured to scan a QR code, bar code or other coded printed on the bandage or bandage packaging. As described above, this combination of a scanner and specific code can be utilized to control the activation of the therapy providing device 200. Additionally, the use of a security code/barcode can be combined with the magnetic activation of the therapy providing device 200 as described above to ensure that the bandage being utilized is an approved product that has been designed to be specifically utilized with the therapy providing device 200 and that the bandage is not a third-party un-approved product or a counterfeit product. It is contemplated that other types of security systems can be utilized to achieve the same or similar functions. For example, the bandage may include a protrusion (not shown) that projects above the surface of the bandage, the protrusion would be received within an aperture of the second surface of the housing where it would activate a switch within the housing. Another example would be the use of an electronic circuit or chip disposed upon or within the bandage, the circuit or chip would interface with the therapy providing device, thereby completing a circuit to enable activation of the therapy providing device.

Figure 17:
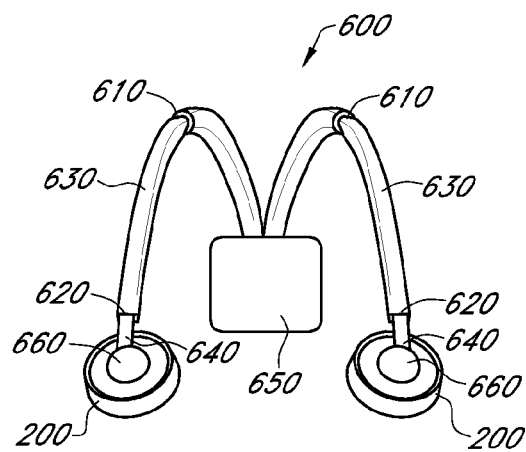
FIGS. 17 and 18 illustrate embodiments of support structures for use with the present invention.

Referring now to FIG. 17 there is shown an alternative design for a mounting device to be utilized with the therapy system 100 in accordance with the present invention. As shown in FIG. 17 there is shown a support structure 600. The support structure 600 can be configured to position therapy providing devices 200 according to the present invention in a preferred location over a user's clavicle. The user can also adjust the positioning of the location of the therapy providing devices 200 by adjusting both the angle of the arm about pivot 610 and buy adjusting the length through the telescoping assembly 620.

The support structure 600 further includes a ball and cup joint 660 at the distal ends 640 of the arms 630. The ball and cup joint 660 is arranged to hold the therapy providing device 200 and allows a user to align the therapy providing device 200 substantially parallel to a surface of the user at the desired location to insure that as much as possible of the therapy providing device 200 is in contact with the user.

The support structure 600 further includes a pad 650 connected to the arms 630. In accordance with embodiments of the present invention, the pad may contain the electronics module 320 and the power source.

The arms 630 of the support structure 600 can also be configured to include a spring force to push the therapy providing device 200 against the body. For example, the arms 630 of the support structure 600 depicted in FIG. 17 are curved and are configured to apply a spring force between the therapy providing units 200 and the pad 650 when the support structure 600 is placed over a user's shoulders.

Figure 18:
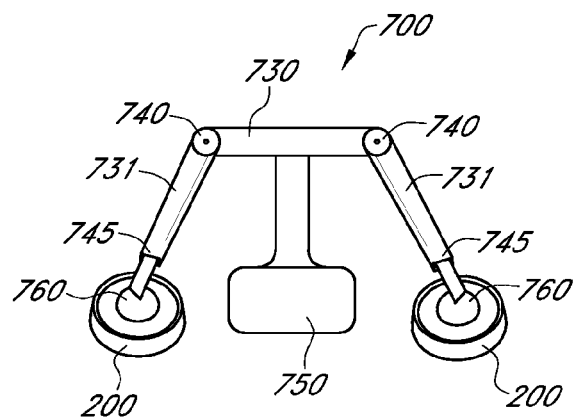

Referring now to FIG. 18 there is shown another example, of a support structure 700 in accordance with the present invention. As shown in FIG. 4H, the support structure 700 includes a pad 750, a first arm 730, and second arms 731. The support structure 700 further includes joints 740, the joints 740 join the first arm 730 to the second arms 731. The joints 740 are configured to allow for rotational motion between the first arm 730 and the second arms 731 in order to allow a user to align the therapy providing devices 200 in accordance with the methods of the present invention. The second arms 731 further include telescoping sections 745. The telescoping sections 745 allow the user to adjust the length of the second arms 731 to position the therapy providing units properly. The second arms 731 further include a ball joint assembly 760 disposed at their distal ends, the ball joint assemblies 760 couple the therapy providing units to the second arms 731. The ball joint assemblies 760 allow the therapy providing units to lay flat against the user's collar bones and account for differences in anatomy. The support structure 700 further includes a pad 750 coupled to the first arm 730. As described above the pad 750 may contain the electronics module 320 and the power source. In certain embodiments the electronics module and power source would be user replaceable. In other embodiments, the electronics module and battery would not be user replaceable and the entire assembly would be replaced including the therapy providing devices.

The support structures 600 and 700 can be made of an elastic material. The elasticity of the design provides for a spring or clamping force, such that the support structure and therapy providing devices remain in position during use.

The support structures described herein can be configured to fit snugly without being too compressive on the body, are straightforward to put on over the shoulders or around the torso, and can be worn underneath clothing without significantly altering the profile of the clothing.

Figure 19A:
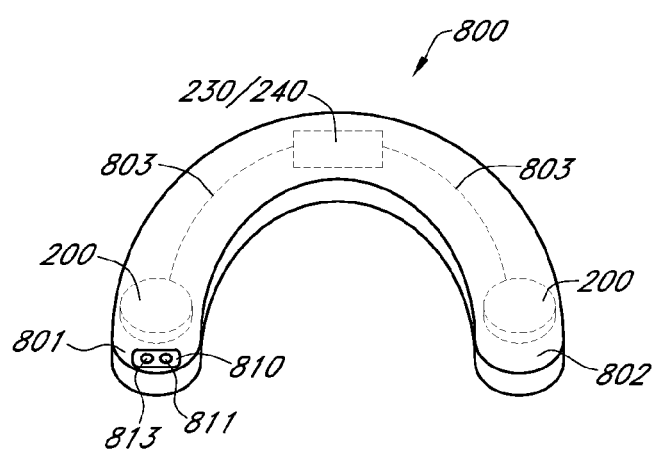
FIGS. 19A-19C illustrate another housing in accordance with the present invention, the housing configured to be received about a user's shoulders.
Figure 19B:
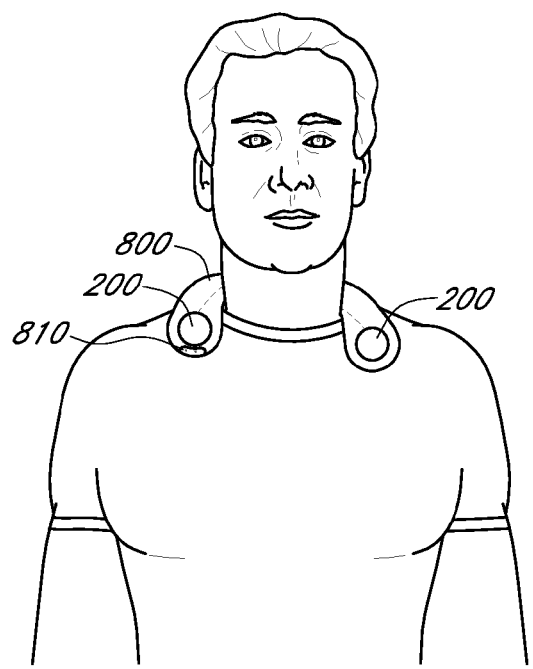
Figure 19C:
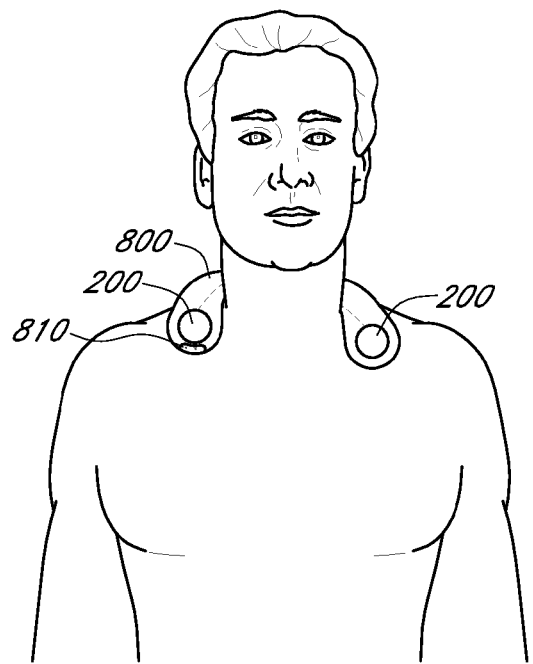

Referring now to FIGS. 19A-19C, there are shown additional embodiments of the present invention. As shown in FIGS. 19A-19C, the therapy providing device 200 of the present invention may be incorporated into a support structure 800, wherein the support structure 800 includes a proximal end 802 and a distal end 801 and an elongate member 803 extending between the two ends. The support structure further includes a control panel 810, wherein the control panel 810 may include an indicator such as a light or LED 811 to indicate the function of the therapy providing devices 200. The control panel 810 further includes a switch 813, the switch 813 being in electrical communication with the therapy providing devices 200 and the electronics module 230 and the energy source 240, each of which have been described above. The support structure 800 may be fabricated of fabric such as cotton, nylon, polyester or the like, wherein the body 803 is in the form of a tubular, square, rectangular or cylindrical shape, thereby forming an inner chamber. As shown in FIG. 19A, the therapy providing devices 200 and the electronics module 230 and energy source 240 are shown disposed within the inner chamber. These components may be held within the inner chamber through the use of pockets formed within the inner chamber. It is further contemplated that the inner chamber may be filled with a material to increase the weight of the overall device. Examples of materials that can be utilized to fill the chamber are rice, beans, sand, metallic materials, polymer materials and other such materials that are known to one skilled in the art.

As shown in FIGS. 19B and 19C, the support structure 800 can be worn around a user's neck and shoulders, wherein the therapy providing device 200 would be adjusted by the user to fall onto and make contact with the user's clavicle. The support structure 800 may be disposed over the top of a user's clothing as shown in FIG. 19B, or alternatively the support structure 800 may be disposed directly against a user's skin as shown in FIG. 19C.

In accordance with the embodiment shown in FIGS. 19A-19C, it is contemplated that the support structure may further include a removable cover (not shown), wherein the removable cover can be disposed about the support structure 800. The removable cover may include a zipper, velcro or snaps to open and close the cover. Additionally, the removable cover may include additional items such as pads placed along a portion or a length thereof. For example, a pad may be disposed on the cover near the user's neck area.

It is further contemplated that the support structure 800 in accordance with the present invention may include additional features. For example, a heating element may be incorporated into the support structure 800, whereby the heating element may be utilized by the user to address sore muscles or neck pain.

Figure 20A:
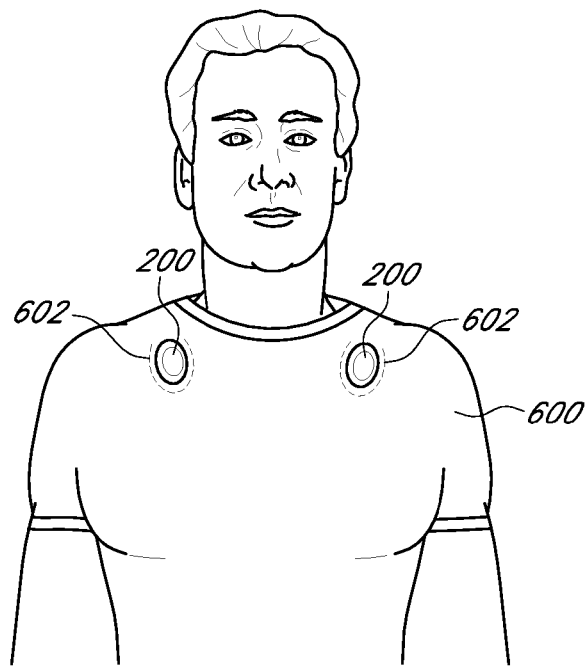
FIGS. 20A and 20B illustrate alternative clothing mounting arrangements for the therapy device of the present invention.
Figure 20B:
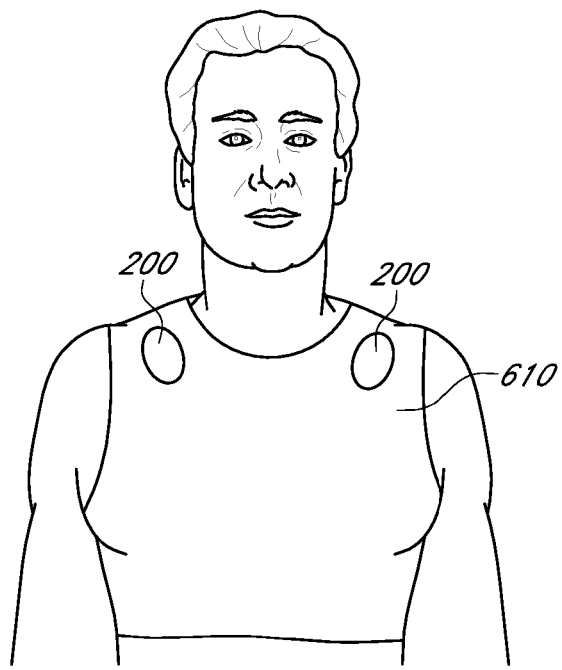

Referring now to FIGS. 20A and 20B, there are shown exemplary embodiments of clothing articles which can be utilized with the therapy providing device 200 of the present invention.

As shown in FIG. 20A, in one embodiment, the clothing article is embodied as a t-shirt 600, wherein the t-shirt 600 includes pockets 602 formed therein to receive the therapy providing device 200. The pockets 602 are aligned over the user's clavicle in order to provide treatment as will be described below.

Referring now to FIG. 20B there is shown an alternative embodiment of a piece of clothing configured to retain the therapy device 200 in accordance with the present invention. As shown in FIG. 5B the clothing can be embodied in the form of a sports bra 610. The sports bra 610 further includes pockets 612 configured to receive the therapy device 200. Alternatively, instead of pockets, other attachment mechanisms such as those described above, wherein instead of pockets, magnets, hook and loop fasteners, snap fasteners, twist and lock or similar types of fastening systems may be utilized to retain the therapy providing device 200 in position.

Additionally, the clothing devices described above may further include an additional pocket or pockets to receive the computing device, or in embodiments wherein the electronics or energy source are separate from the therapy providing device, pockets or other retention means to retain these additional components.

The clothing devices may further include a structure formed therein or attached thereto (not shown) wherein the structure is configured to apply a downward force upon the therapy providing device(s). Structures similar to those shown in FIGS. 17, 18 and 19 may be utilized.

In accordance with the present invention, the therapy providing device 200 may include addition features. One such additional feature can be the inclusion of a thermometer to track the user's temperature during use. Another additional feature can be the inclusion of a sleep sensor or sleep tracking program, wherein the therapy providing device can be utilized to track the user's sleep. For example, the sleep program may utilize the GPS/accelerometer of the therapy providing device to track movement during sleep, wherein the sleep program could further utilize the temperature data as well. Another aspect of the invention could be to utilize the therapy providing device to be further utilized to diagnose sleep apnea, wherein the therapy providing device could further include a microphone to enable audio recording of the user's breathing during sleep. Additionally, the microphone recording of the breathing can be combined with the accelerometer data or GPS/tilt data to correlate the breathing recordings to the specific user.

Figure 21A:
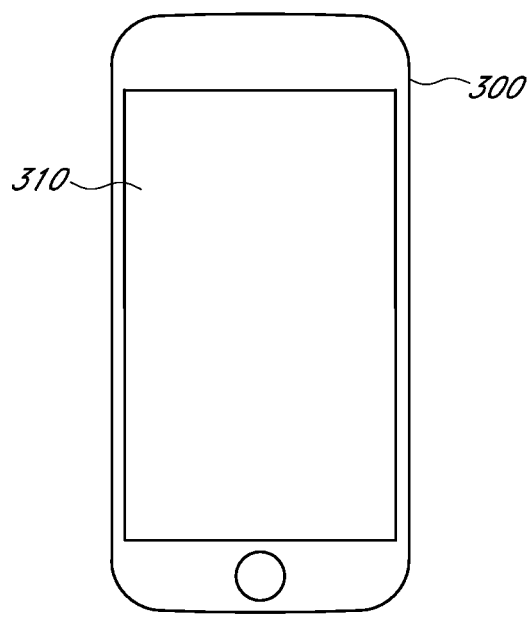
FIG. 21A illustrates an exemplary embodiment of a computing device in accordance with the present invention.
Figure 21B:
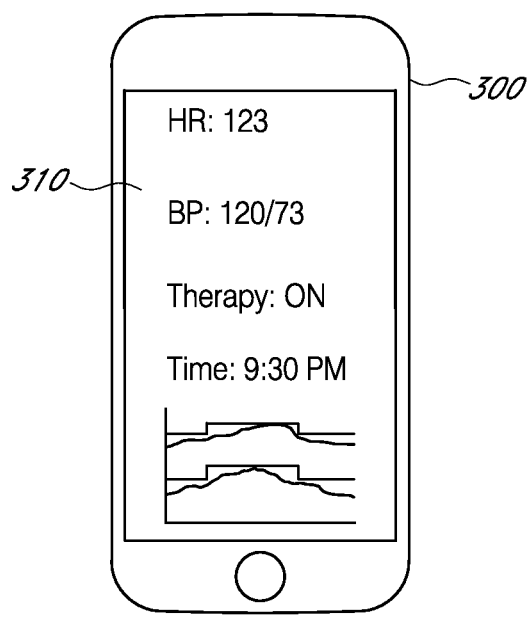
FIG. 21B illustrates and exemplary screen view of a program displayed on the exemplary computing device of FIG. 21A in accordance with the present invention.

Referring now to FIGS. 21A and 21B there is shown a computing device 300 in accordance with the present invention. The computing device 300 includes a processor, memory, energy source (such as a battery), and a display. The computing device may be a custom manufactured device for use with the therapy device 200 as described above, or alternatively, the computing device 300 may be a commercially available device such as a smartphone or tablet. Examples of such commercially available devices are iOS enabled devices such as the iPhone®, iPad®, iPod®, Android based phones and/or tablets, laptops or computers. As shown in FIG. 15B, the computing device may be configured to display a user's heart rate and blood pressure when connected to a therapy providing device having those measurement capabilities or where other compatible devices are utilized with the therapy providing device. Alternatively, the computing device may display data received from one or more therapy providing devices, this data may include start/stop times of therapy provided by the therapy providing device 200, battery status of one or more therapy providing devices and the like.

In accordance with the present invention, the computing device 300 is configured to run a program 820. In accordance with the present invention, the program 820 is configured to communicate with the therapy device 200. The communication between the program 820, computing device 300 and the therapy device 200 may be conducted using BLUETOOTH, WIFI, ZIGBEE, NFC, RFID, ANT+, 3G/4G, cellular connection or other known wireless communication protocols. Alternatively, the computing device may be coupled to at least one of the therapy devices through a cable connection.

In an alternative embodiment, the program 820 is stored on memory located within the memory of the therapy providing device 200. The program may be initiated manually through the use of a physical button pressed by the user. Alternatively, the program 820 may be initiated automatically by a timer located within the therapy providing device 200. The timer may further utilize data inputs from an accelerometer/compass or tilt sensor to indicate when the user is in a prone position to initiate the program 820. Further still, the timer may receive input from an impedance sensor indicating whether the therapy providing device 200 is in proper placement on the users body. The program would then be initiated based on the inputs received. The device may be activated further by the light sensor either from the darkness against the skin. The device may be activated from the reduced light from the users surroundings, for example when the user is sleeping.

In certain embodiments, the program 820 is pre-configured to deliver therapy using the therapy providing device through pre-programmed parameters. The HCP may adjust the therapy parameters within the program 820, such that the therapy provided to the user may be customized to the user. The customization of the therapy may be changes to the wavelength, amplitude, duration, start/stop times. The customization may be done by the HCP while providing services to the patient, for example, the HCP may apply the therapy providing device to the patient, initiate therapy and monitor the patient's response. Through this active monitoring, the HCP may change the parameters of the program to elicit a response in the patient. For example, it is contemplated that certain patients may have different bone densities; therefore the therapy provided by the device may need to be adjusted accordingly. It is further contemplated, that once programmed, the user cannot change the therapy parameters of the program, or alternatively, certain parameters or all parameters may be open to change by the end user or remotely. Alternatively, the HCP, after determining the best therapy parameters, can choose from multiple programs stored within memory of the therapy providing device. Further still, the HCP may be provided with a dedicated programming device, or may couple the device to a personal computer, smartphone, tablet or other internet enabled device, such that the HCP can utilize the dedicated programmer or download over a secure internet connection, programs to be uploaded into the therapy providing device.

Figure 22:
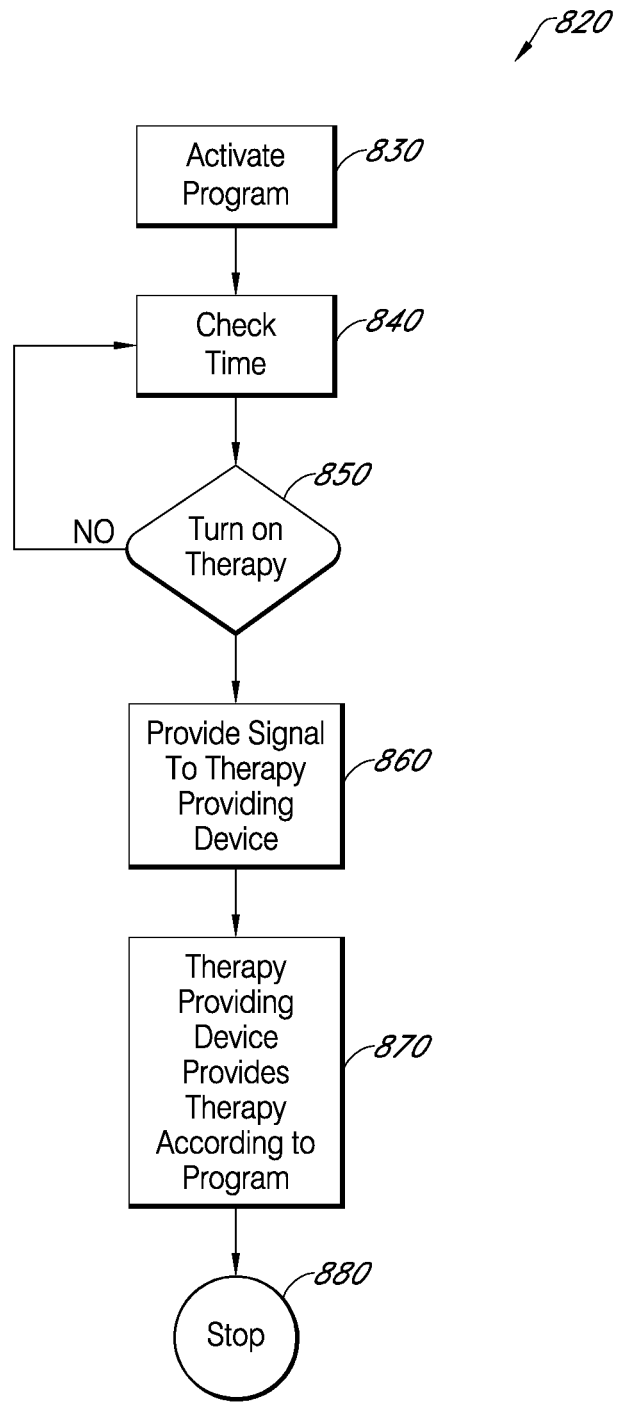
FIG. 22 illustrates a flow diagram for a software program in accordance with the present invention.

Referring now to FIG. 22, there is shown a flow diagram illustrating the program 820 in accordance with one embodiment of the present invention. As shown in FIG. 22, the program 820 may configured to be run on the computing device 800 to control the therapy applied to the user by the therapy providing device 200. Alternatively, it is contemplated that the program 820 may reside within memory within the therapy providing device 200 as described above.

At Box 830, the user activates the program on the computing device 800 or therapy providing device 200.

At Box 840, the program checks the time on the computing device 800 or internally from the clock circuit of the therapy providing device 200.

At Box 850, the program determines whether to turn the therapy providing device on based upon the time check in Box 840. If the time is before a pre-programmed time or a user set time, then the program returns to Box 840. If the time is after the pre-set time or user set time, then the program turns the therapy providing device on. In accordance with the invention, if the time is received from the computing device, a user may adjust the time of the computing device, for example if the computing device is moved from one time zone to another. Alternatively, the computing device may automatically update the time.

At Box 860, the therapy providing device 200 is provided with a signal generated by the program and transmitted from the computing device 800 through a selected transmission method. In alternative embodiments, the therapy providing device contains a processor and memory, wherein a program is retained within the memory of the therapy providing device. In this embodiment, the signal provided by the computing device 800, is a power on/off signal, wherein once powered on the program residing within the memory of the therapy providing device will begin to run.

At Box 870, the therapy device provides therapy to the patient. In the process of providing therapy, a signal is transmitted to the therapy device 200 by the computing device 800 through as directed by the program 820, or as described above, the program residing in the memory of the therapy providing device runs. In one embodiment, the therapy is applied for a set period of time. In alternative embodiments, the time duration of the therapy may be determined based upon data received from other sensors disposed upon the user or about the user. In yet another embodiment, the user may manually deactivate the therapy providing device/program.

At Box 880, the therapy is stopped. The therapy may be stopped based upon a time event, motion event, manually by the user, automatically by the program.

During each of the steps described above and shown in the flow diagram of FIG. 22, the user may be presented with displays on the screen 810 of the computing device. The screen 810 may display the start and stop times of the therapy, these times may be set by the user or may be set for the user by a health care provider. Alternatively, the times maybe automatically generated in response to data received from other sensors as will be described in detail below.

According to the invention, the program includes a non-transitory computer readable medium having computer executable program code embodied thereon, the computer executable program code configured to send appropriate signals to the circuit board(s) 500/550 to provide therapy in accordance with the methods of the present invention utilizing the therapy providing device 200 of the present invention.

Methods of Use

In accordance with the present invention, methods of use of the present invention will be described below. The methods described shall be considered to be exemplary and should not be considered limiting in any manner.

In accordance with one embodiment of the present invention, the therapy device includes a driver assembly, wherein the driver assembly is embodied as a speaker as shown in FIG. 5. The speaker may be a haptic speaker, a piezoelectric speaker, an electroactive polymeric transducer, or a magnetic coil speaker. The computing device 800 and program 810 are configured to provide a signal to the speaker to cause the speaker to vibrate at certain frequencies or to oscillate or translate through a range of frequencies.

In accordance with embodiments of the present invention, the frequencies contemplated for use with the present invention range between 0 Hz to 20,000 Hz, 0 Hz and 10,000 Hz, 0 Hz and 5,000 Hz, 0 Hz and 2,500 Hz, 0 Hz and 1,750 Hz, 0 Hz and 875 Hz, 0 Hz and 435 Hz, 0 Hz and 200 Hz, 0 Hz and 150 Hz, 1 Hz and 150 Hz, 2 Hz and 150 Hz, 3 Hz and 150 Hz, 4 Hz and 150 Hz, 5 Hz and 150 Hz, 6 Hz and 150 Hz, 7 Hz and 150 Hz, 8 Hz and 150 Hz, 9 Hz and 150 Hz, 10 Hz and 150 Hz, 11 Hz and 150 Hz, 12 Hz and 150 Hz, 13 Hz and 150 Hz, 14 Hz and 150 Hz, 15 Hz and 150 Hz, 16 Hz and 150 Hz, 17 Hz and 150 Hz, 18 Hz and 150 Hz, 19 Hz and 150 Hz, 20 Hz and 150 Hz, 21 Hz and 150 Hz, 22 Hz and 150 Hz, 23 Hz and 150 Hz, 24 Hz and 150 Hz, 25 Hz and 150 Hz, 26 Hz and 150 Hz, 27 Hz and 150 Hz, 28 Hz and 150 Hz, 28 Hz and 150 Hz, 29 Hz and 150 Hz, 30 Hz and 150 Hz, 31 Hz and 150 Hz, 32 Hz and 150 Hz, 33 Hz and 150 Hz, 34 Hz and 150 Hz, 35 Hz and 150 Hz, 36 Hz and 150 Hz, 37 Hz and 150 Hz, 38 Hz and 150 Hz, 39 Hz and 150 Hz, 40 Hz and 150 Hz, 41 Hz and 150 Hz, 42 Hz and 150 Hz, 43 Hz and 150 Hz, 44 Hz and 150 Hz, 45 Hz and 150 Hz, 46 Hz and 150 Hz, 47 Hz and 150 Hz, 48 Hz and 150 Hz, 49 Hz and 150 Hz, 50 Hz and 150 Hz, 51 Hz and 150 Hz, 52 Hz and 150 Hz, 53 Hz and 150 Hz, 54 Hz and 150 Hz, 55 Hz and 150 Hz, 56 Hz and 150 Hz, 57 Hz and 150 Hz, 58 Hz and 150 Hz, 59 Hz and 150 Hz, 60 Hz and 150 Hz, 61 Hz and 150 Hz, 62 Hz and 150 Hz, 63 Hz and 150 Hz, 64 Hz and 150 Hz, 65 Hz and 150 Hz, 66 Hz and 150 Hz, 67 Hz and 150 Hz, 68 Hz and 150 Hz, 69 Hz and 150 Hz, 70 Hz and 150 Hz, 71 Hz and 150 Hz, 72 Hz and 150 Hz, 73 Hz and 150 Hz, 74 Hz and 150 Hz, 75 Hz and 150 Hz, 76 Hz and 150 Hz, 77 Hz and 150 Hz, 78 Hz and 150 Hz, 79 Hz and 150 Hz, 80 Hz and 150 Hz, 81 Hz and 150 Hz, 82 Hz and 150 Hz, 83 Hz and 150 Hz, 84 Hz and 150 Hz, 85 Hz and 150 Hz, 86 Hz and 150 Hz, 87 Hz and 150 Hz, 88 Hz and 150 Hz, 89 Hz and 150 Hz, 90 Hz and 150 Hz, 91 Hz and 150 Hz, 92 Hz and 150 Hz, 93 Hz and 150 Hz, 94 Hz and 150 Hz, 95 Hz and 150 Hz, 96 Hz and 150 Hz, 97 Hz and 150 Hz, 98 Hz and 150 Hz, 99 Hz and 150 Hz, 100 Hz and 150 Hz, 101 Hz and 150 Hz, 102 Hz and 150 Hz, 103 Hz and 150 Hz, 104 Hz and 150 Hz, 105 Hz and 150 Hz, 106 Hz and 150 Hz, 107 Hz and 150 Hz, 108 Hz and 150 Hz, 109 Hz and 150 Hz, 110 Hz and 150 Hz, 111 Hz and 150 Hz, 112 Hz and 150 Hz, 113 Hz and 150 Hz, 114 Hz and 150 Hz, 115 Hz and 150 Hz, 116 Hz and 150 Hz, 117 Hz and 150 Hz, 118 Hz and 150 Hz, 119 Hz and 150 Hz, 120 Hz and 150 Hz, 121 Hz and 150 Hz, 122 Hz and 150 Hz, 123 Hz and 150 Hz, 124 Hz and 150 Hz, 125 Hz and 150 Hz, 126 Hz and 150 Hz, 127 Hz and 150 Hz, 128 Hz and 150 Hz, 129 Hz and 150 Hz, 130 Hz and 150 Hz, 131 Hz and 150 Hz, 132 Hz and 150 Hz, 133 Hz and 150 Hz, 134 Hz and 150 Hz, 135 Hz and 150 Hz, 136 Hz and 150 Hz, 137 Hz and 150 Hz, 138 Hz and 150 Hz, 139 Hz and 150 Hz, 140 Hz and 150 Hz, 141 Hz and 150 Hz, 142 Hz and 150 Hz, 143 Hz and 150 Hz, 144 Hz and 150 Hz, 145 Hz and 150 Hz, 146 Hz and 150 Hz, 147 Hz and 150 Hz, 148 Hz and 150 Hz, 149 Hz and 150 Hz, 150 Hz and 150 Hz, 60 Hz and 100 Hz, 61 Hz and 100 Hz, 62 Hz and 100 Hz, 63 Hz and 100 Hz, 64 Hz and 100 Hz, 65 Hz and 100 Hz, 66 Hz and 100 Hz, 67 Hz and 100 Hz, 68 Hz and 100 Hz 69 Hz and 100 Hz, 70 Hz and 100 Hz, 60 Hz and 99 Hz, 61 Hz and 99 Hz, 62 Hz and 99 Hz, 63 Hz and 99 Hz, 64 Hz and 99 Hz, 65 Hz and 99 Hz, 66 Hz and 99 Hz 67 Hz and 99 Hz, 68 Hz and 99 Hz, 69 Hz and 99 Hz and 70 Hz and 99 Hz, and 61 Hz and 98 Hz, 62 Hz and 98 Hz, 63 Hz and 98 Hz, 64 Hz and 98 Hz, 65 Hz and 98 Hz, 66 Hz and 98 Hz, 67 Hz and 98 Hz, 68 Hz and 98 Hz, 69 Hz and 98 Hz and 70 Hz and 98 Hz.

In a preferred embodiment the signal causes the driver assembly to vibrate at a frequency or sweep through a range of frequencies between about 40 Hz and 150 Hz, more preferably between 50 Hz and 125 Hz, most preferably between about 60 Hz and 115 Hz. In accordance with the present invention, a therapeutic response has been achieved utilizing a frequency range between 65 Hz and 100 Hz.

It is further contemplated that these frequencies may be doubled and still achieve the therapeutic lowering of blood pressure in accordance with the present invention. It is further contemplated that these frequencies may be halved and still achieve the therapeutic lowering of blood pressure in accordance with the present invention.

In additional embodiment of the present invention, the driver assembly may vibrate or sweep or step between frequencies of between 60 Hz, 61 Hz, 62 Hz, 63 Hz, 64 Hz, 65 Hz, 66 Hz, 67 Hz, 68 Hz, 69 Hz, 70 Hz, 71 Hz, 72 Hz, 73 Hz, 74 Hz, 75 Hz, 76 Hz, 77 Hz, 78 Hz, 79 Hz, 80 Hz, 81 Hz, 82 Hz, 83 Hz, 84 Hz, 85 Hz, 86 Hz, 87 Hz, 88 Hz, 89 Hz, 90 Hz, 91 Hz, 92 Hz, 93 Hz, 94 Hz, 95 Hz, 96 Hz, 97 Hz, 98 Hz, 99 Hz and 100 Hz.

Figure 23A:
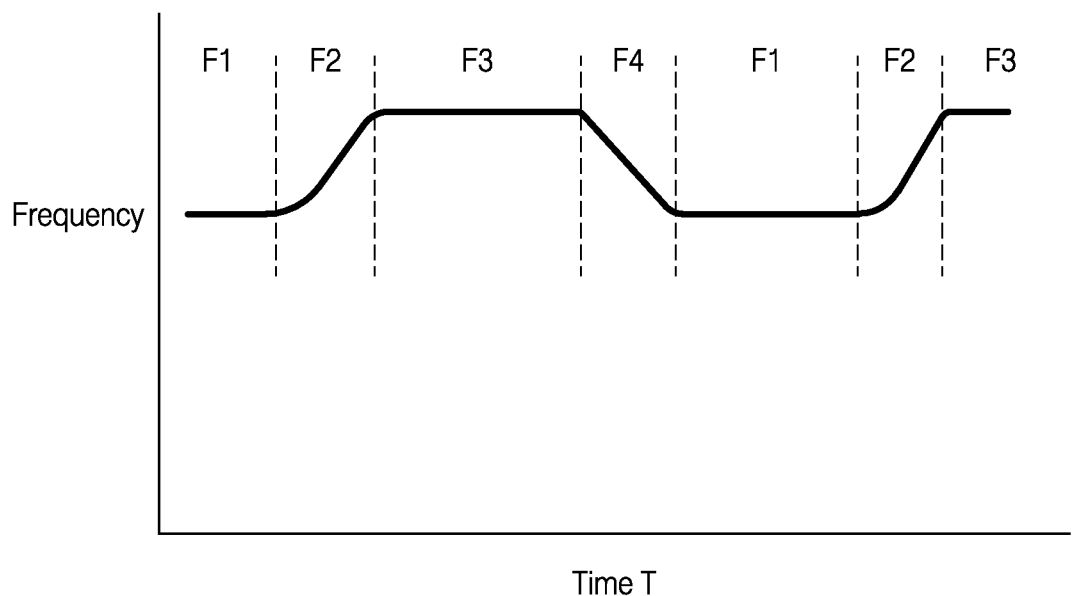
FIG. 23A illustrates a therapeutic frequency curve for the therapy provided by an exemplary embodiment of the present invention.
Figure 23B:
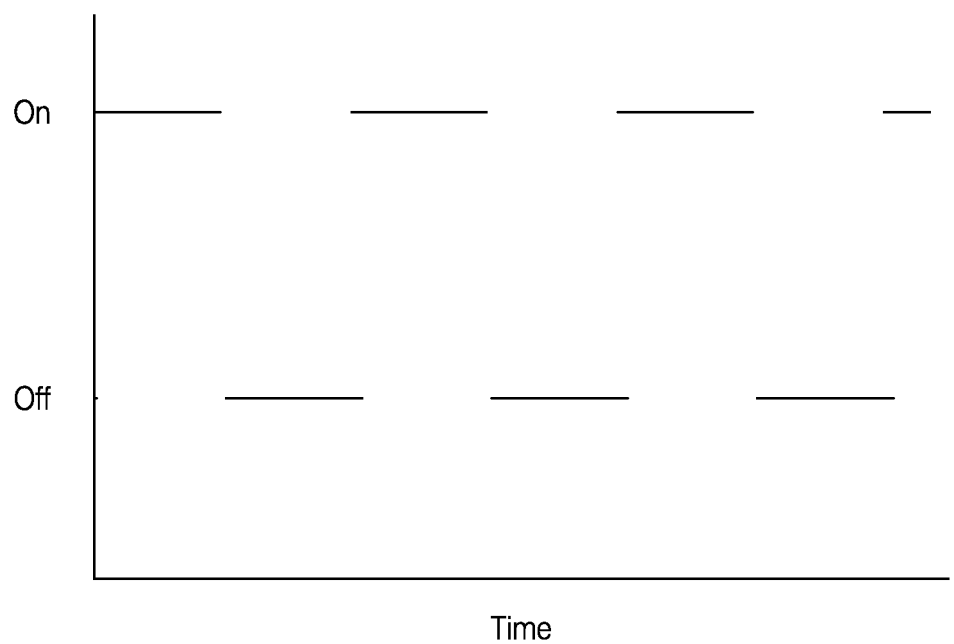
FIG. 23B illustrates a timed therapy sequence in accordance with an embodiment of the present invention.

Referring now to FIGS. 23A and 23B, there is shown a further embodiment wherein the therapy is provided utilizing a combination of single frequencies and a sweeping frequency. For example, the driver assembly would be driven to vibrate at a single frequency, F1, for a period of time, then driven to sweep through a range of frequencies, F2, then driven at a single frequency, F3, different than the first single frequency, F1, and then finally driven backwards through the sweep of frequencies above, F4. This cycle may be repeated for a set period of time, turned off for a period of time and then repeated again, until an overall time period of therapy is reached.

It is further contemplated that multiple signals utilizing separate frequencies may be transmitted by the program to the speaker. For example, one signal may be transmitted at one frequency and a second signal at another frequency. The signals may be transmitted simultaneously, independently or in an alternating fashion. If at least two therapy providing devices 200 are utilized, then one therapy providing device 200 may receive a first signal and the other receives a second signal.

In one embodiment, at least two therapy providing devices 200 are utilized. In use a signal will be sent to one of the two therapy providing devices 200, causing the speaker to emit a signal having a chosen frequency or range of frequencies. The signal is transmitted to a first therapy providing device 200 for a pre-determined period of time. After such time, the signal is terminated. Upon termination of the first signal, a second signal is generated and transmitted to the other therapy providing device. This second signal causes the speaker to emit a signal having a chosen frequency or range or frequencies. The chosen frequency may be the same as that transmitted to the first therapy providing device or it may be at a different frequency. The second signal will be transmitted to the second therapy providing device for a pre-determined period of time. After such time, the signal is terminated. The program will continued to run, however, during this time no signal will be transmitted to either therapy providing device 200, thereby creating a pause between activation of the therapy providing devices 200. After the pre-determined time period of the pause has passed, the program will then enter a loop and repeat the process described above. This pattern of therapy will repeat for as long as the program has been instructed to do so.

In the embodiment where two therapy providing devices 200 are utilized, each of the devices deliver a waveform to the user's left and right clavicle. The waveform is transmitted from the speaker in each of the therapy providing devices to the user's clavicles. The waveform is transmitted through the clavicle on the left and right side, where both waves meet at the sternum to create a standing wave.

Further still, in accordance with the present invention, the amplitude of the signal can be adjusted to adjust the sound pressure generated by the driver assembly 220 of the therapy providing device 200. It is contemplated that the amplitude may be doubled or increased even more to deliver the therapy in accordance with the present invention. In accordance with the invention, the therapy providing device 200 may be configured to provide a sound pressure between: 0 to 150 decibels, 0 to 100 decibels, 0 to 99 decibels, 0 to 98 decibels, 0 to 97 decibels, 0 to 96 decibels, 0 to 95 decibels, 0 to 94 decibels, 0 to 93 decibels, 0 to 92 decibels, 0 to 91 decibels, 0 to 90 decibels, 0 to 89 decibels, 0 to 88 decibels, 0 to 87 decibels, 0 to 86 decibels, 0 to 85 decibels, 0 to 84 decibels, 0 to 83 decibels, 0 to 82 decibels, 0 to 81 decibels, 0 to 80 decibels, 0 to 79 decibels, 0 to 78 decibels, 0 to 77 decibels, 0 to 76 decibels, 0 to 75 decibels, 0 to 74 decibels, 0 to 73 decibels, 0 to 72 decibels, 0 to 71 decibels, 0 to 70 decibels, 0 to 69 decibels, 0 to 68 decibels, 0 to 67 decibels, 0 to 66 decibels, 0 to 65 decibels, 0 to 64 decibels, 0 to 63 decibels, 0 to 62 decibels, 0 to 61 decibels, 0 to 60 decibels, 0 to 59 decibels, 0 to 58 decibels, 0 to 57 decibels, 0 to 56 decibels, 0 to 55 decibels, 0 to 54 decibels, 0 to 53 decibels, 0 to 52 decibels, 0 to 51 decibels, 0 to 50 decibels, 0 to 49 decibels, 0 to 48 decibels, 0 to 47 decibels, 0 to 46 decibels, 0 to 45 decibels, 0 to 44 decibels, 0 to 43 decibels, 0 to 42 decibels, 0 to 41 decibels, 0 to 40 decibels, 0 to 39 decibels, 0 to 38 decibels, 0 to 37 decibels, 0 to 36 decibels, 0 to 35 decibels, 0 to 34 decibels, 0 to 33 decibels, 0 to 32 decibels, 0 to 31 decibels, 0 to 30 decibels, 0 to 29 decibels, 0 to 28 decibels, 0 to 27 decibels, 0 to 26 decibels, 0 to 25 decibels, 0 to 24 decibels, 0 to 23 decibels, 0 to 22 decibels, 0 to 21 decibels, 0 to 20 decibels, 0 to 19 decibels, 0 to 18 decibels, 0 to 17 decibels, 0 to 16 decibels, 0 to 15 decibels, 0 to 14 decibels, 0 to 13 decibels, 0 to 12 decibels, 0 to 11 decibels, 0 to 10 decibels, 0 to 9 decibels, 0 to 8 decibels, 0 to 7 decibels, 0 to 6 decibels, 0 to 5 decibels, 0 to 4 decibels, 0 to 3 decibels, 0 to 2 decibels, 0 to 1 decibels, 0 to 0.5 decibels, 0 to 0.25 decibels, 10 to 100 decibels, 20 to 100 decibels, 30 to 100 decibels, 40 to 100 decibels, 50 to 100 decibels, 60 to 100 decibels, 70 to 100 decibels, 80 to 100 decibels, 90 to 100 decibels, 10 to 75 decibels, 20 to 75 decibels, 30 to 75 decibels, 40 to 75 decibels, 50 to 75 decibels, 60 to 75 decibels, 70 to 75 decibels, 10 to 65 decibels, 20 to 65 decibels, 30 to 65 decibels, 40 to 65 decibels, 50 to 65 decibels and 60 to 65 decibels, 20 to 30 decibels, 30 to 40 decibels, 40 to 50 decibels, 50 to 60 decibels, 60 to 70 decibels, 70 to 75 decibels, 80 to 90 decibels, 50 to 75 decibels and 50 to 65 decibels.

Further still, in accordance with the present invention, the standing wave may be of half-octave, double octave, or reflective incidence. Thus the frequencies delivered at the collarbone may independently collide across the breastbone or sternum and create a new frequency which is of a different or same frequency as the generating waves.

In accordance with the present invention, the frequency selected for therapy may be held constant while the sound pressure level can be increased or decreased, alternatively, the sound pressure level may be held constant and the frequency varied. The measurement of a sound pressure level is related to the displacement of a portion of the delivery device 220. The portion of the delivery device 220 may be displaced between: 0 mm and 20 mm, 0 mm to 10 mm, 0 mm to 9 mm, 0 mm and 8 mm, 0 mm to 7 mm, 0 mm to 6 mm, 0 mm to 5 mm, 0 mm and 4 mm, 0 mm and 3 mm, 0 mm and 2 mm, 0 mm and 1 mm, 0 mm and 0.5 mm, 0 mm to 0.05 mm, 0 mm to 0.005 mm, 0 mm to 0.0005 mm, 0.5 mm to 0.05 mm, 0.5 mm to 0.005 mm, 0.05 mm to 0.005. If the delivery device 220 is selected to be the haptic speaker 220', then the portion of the haptic speaker 220' being displaced is the coil of the haptic speaker.

In accordance with the present invention, it is contemplated that each therapy providing device may be activated to provide therapy for a time period between about 1 second and 24 hours. In other embodiments, the therapy providing devices may be activated to provide therapy for a time period of between about 1 second and 12 hours, 1 second and 11 hours, 1 second and 10 hours, 1 second and 9 hours, 1 second and 8 hours, 1 second and 7 hours, 1 second and 6 hours, 1 second and 5 hours, 1 second and 4 hours, 1 second and 3 hours 1 second and 2 hours, and 1 second and 1 hour, 1 second and 45 minutes, 1 second and 30 minutes, 1 second and 20 minutes, 1 second and 15 minutes, 1 second and 10 minutes, 1 second and 5 minutes and 1 second and 1 minute.

The overall therapy process may be conducted for a time period between 1 second and 24 hours, 1 second and 23 hours, 1 second and 22 hours, 1 second and 21 hours, 1 second and 20 hours, 1 second and 19 hours, 1 second and 18 hours, 1 second and 17 hours, 1 second and 16 hours, 1 second and 15 hours, 1 second and 15 hours, 1 second and 14 hours, 1 second and 13 hours, 1 second and 12 hours, 1 second and 11 hours, 1 second and 10 hours, 1 second and 9 hours, 1 second and 8 hours, 1 second and 7 hours, 1 second and 6 hours, 1 second and 5 hours, 1 second and 4 hours, 1 second and 3 hours, 1 second and 2 hours, 1 second and 1 hour, 1 second and 45 minutes, 1 second and 30 minutes, 1 second and 15 minutes, 1 second and 10 minutes, 1 second and 5 minutes, 1 second and 1 minute.

In an alternative embodiment, instead of activating one therapy providing device 200 at a time to conduct the therapy, both therapy providing devices 200 may be activated at the same time.

In accordance with the present invention, the therapy device may be factory programmed to utilize a certain frequency or range of frequencies to provide therapy. Alternatively, the frequencies may be selected and programmed or chosen from memory by a health care provider based upon a patient's response to a specific frequency or range of frequencies.

It is further contemplated that the computing device may be additionally in communication with other sensors, such as a blood pressure monitor, heart rate monitor, pulse oximetry monitor, electrocardiogram (EKG/ECG), or glucose sensor.

In one embodiment the computing device 800 would receive data from the blood pressure monitor, or other sensor, such that the user's blood pressure would be recorded before, during and after the application of therapy in accordance with the present invention. This data, along with the therapy data could be provided to the user and/or a health care provider. Based upon the data, the frequency or range of frequencies selected for therapy could be adjusted. The adjustments may be made automatically by the program, or by a health care provider or by the user themselves.

In another embodiment, the processor of the therapy providing device 200 may be in communication with other sensors, such as those described above, wherein the other sensors would be coupled in communication with the therapy providing device. The processor within the therapy providing device 200 can receive data from various other sensors, such as a blood pressure monitor. The data received from the blood pressure monitor may be utilized by the program within the memory of the electronics module to further control the therapy providing device 200.

The signals generated by the program and transmitted to the therapy providing device are preferably in the form of a sine wave. However, other wave forms may be utilized, such as a square waveform, sawtooth waveform or triangle waveform.

It is further contemplated that additional sensors maybe utilized with the methods and devices in accordance with the present invention. For example, a blood pressure monitor may be affixed to the patient as described above. Other sensors, such as a sleep sensor, movement sensor, pulse oximetry sensor, temperature sensor, heart rate monitor, EKG, microphone, digital stethoscope, light sensor, sleep apnea device (CPAP) or camera may be used in combination with the therapy system 100 in accordance with the present invention. The sensors listed above could be used separately or in combination to provide additional data to the user or a health care provider as to the health of the user as well as to the response of the user to the therapy provided by the therapy system 100.

It is further contemplated that any of the above sensors could be incorporated into the therapy providing device 200 in accordance with the present invention. If incorporated into the therapy providing device 200, the data from each of the additional sensors could be utilized by the program to alter the therapy provided based upon data received from the various sensors. In an alternative embodiment, the data from each of the additional sensors could be stored on the resident memory contained within the therapy providing device 200. The therapy providing device 200 could then be turned into a service center after a period of time, wherein the data contained within the memory can be retrieved and analyzed. In yet another embodiment, the data stored within the memory can be downloaded from the therapy providing device 200 each time the therapy providing device is placed on the inductive charging pad. The data can then be transmitted to a collection center and analyzed. Additionally, the data could be uploaded to a server or other internet/network connected personal computer, such that the data could be viewed by the user, a health care provider or others.

In another embodiment, the device will store the number of uses and durations of usage to allow the health care practitioner to determine compliance of the patient. As in sleep apnea devices, reimbursement is only allowed if the patient is 70 percent compliant, by tracking and recording the usage of the therapy providing device of the present invention, this data could be utilized for reimbursement purposes.

In another embodiment, the therapy system 100 of the present invention could be associated with a home health system, such as Honeywell's HOMMED system. In this embodiment, the therapy system 100 in accordance with the present invention would be coupled to a monitoring system. In this embodiment, a health care provider could remotely monitor users as well as their response to the therapy being provided. Further still, the therapy system 100 may be configured to recognize an emergency, such as excessively high blood pressure, excessively low blood pressure, high heart rate or low heart rate and generate an alert, such as an alarm or notification to an emergency response unit to request help for the user.

In accordance with the present invention, the therapy device 200 as described herein is disposed adjacent to or thereabout the clavicle just above the brachial plexus of the user. It is contemplated that the therapy providing device 200 may be placed at other locations on the user such as the sternum, jaw, scapula, kneecap, wrist or skull. When activated, the driver assembly 220 of the therapy device generates a frequency in the form of a sound wave; this sound wave is transmitted to the clavicle and the skin adjacent the clavicle. The sound waves transmitted to the clavicle are transmitted in the form of vibrations. The vibrations travel through the clavicle and into the skin, the arteries, vessels, nerves, sensory corpuscles, airways, bones near the clavicle, ligaments and tendons. As a result, the vibrations are eventually transmitted to the baroreceptors, the nociceptors, the proprioreceptors and other somatasory sensors. Here, the vibrations interact with the baroreceptors and other sensors in a manner to lower blood pressure. In a preferred embodiment, the clavicle is chosen because it's easily accessible location as well as its ability to transmit sound or vibrations. The clavicle is easy to identify by a health care provider and a patient as it resides close to the surface of the skin regardless of body mass.

In accordance with the methods and devices of the present invention, activation of both the carotid and aortic baroreceptors as well as other somatasory sensors can be achieved. It is believed that activation of both the carotid and aortic baroreceptors is beneficial in achieving lower blood pressure. It is believed that the methods provided according to the present invention mimic exercise, and therefore achieve a lowering of blood pressure.

In accordance with the invention, the therapy may be provided at night time either right before the patient enters a sleep cycle or during a sleep cycle of the patient. It may be beneficial to provide the therapy in accordance with the present invention at night time as it is believed that one of the most important times to lower blood pressure is during the night. By providing therapy at night time in accordance with the present invention, the therapy can be utilized to address nighttime hypertension. Additionally, at nighttime, systemic drug levels are at their lowest, therefore there is a need for additional blood pressure control at this time.

In accordance with another embodiment of the present invention, it is believed that through the use of a single therapy providing device instead of two therapy providing devices can be utilized to lower only Diastolic blood pressure, wherein the use of both therapy providing devices can be utilized to lower both Systolic and Diastolic blood pressure.

In accordance with the invention, the therapy may be provided prior to a user's sleep cycle and again in the morning either before they awake or shortly after they have woken up.

In accordance with the invention, the therapy providing device may be programmed with frequencies, wherein other frequencies may be utilized to raise blood pressure at such times whereby raising the blood pressure would be therapeutic and beneficial to a patient. It may be desirable to raise blood pressure after childbirth or to counteract episodes of hypotension.

It is further contemplated that the device and methods according to the present invention may be utilized at any time. For example, it may be desirable to utilize the device during the day time, where the device could be utilized in combination with a blood pressure monitor, or alternatively, incorporate a blood pressure monitor for closed loop control. In this embodiment, the program would monitor the user's blood pressure and apply therapy on an as needed basis. The user could select to turn the system off if desired, for example if they are planning to engage in physical activity which will raise their blood pressure.

Test Results

Figure 24A:
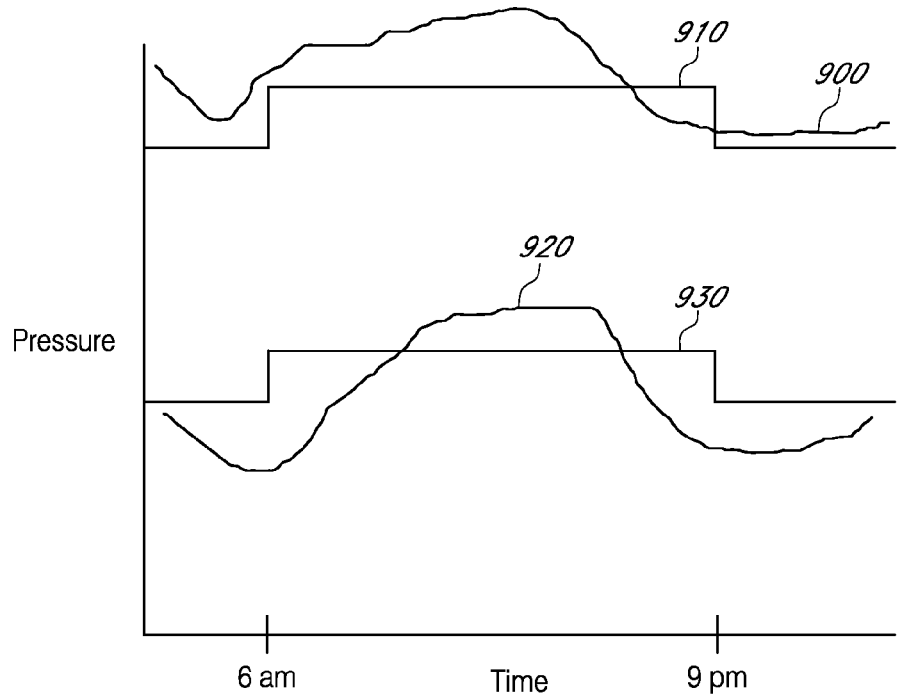
FIG. 24A illustrates a patient's blood pressure reading over a twenty-four hour period, showing a hypertensive patient.
Figure 24B:
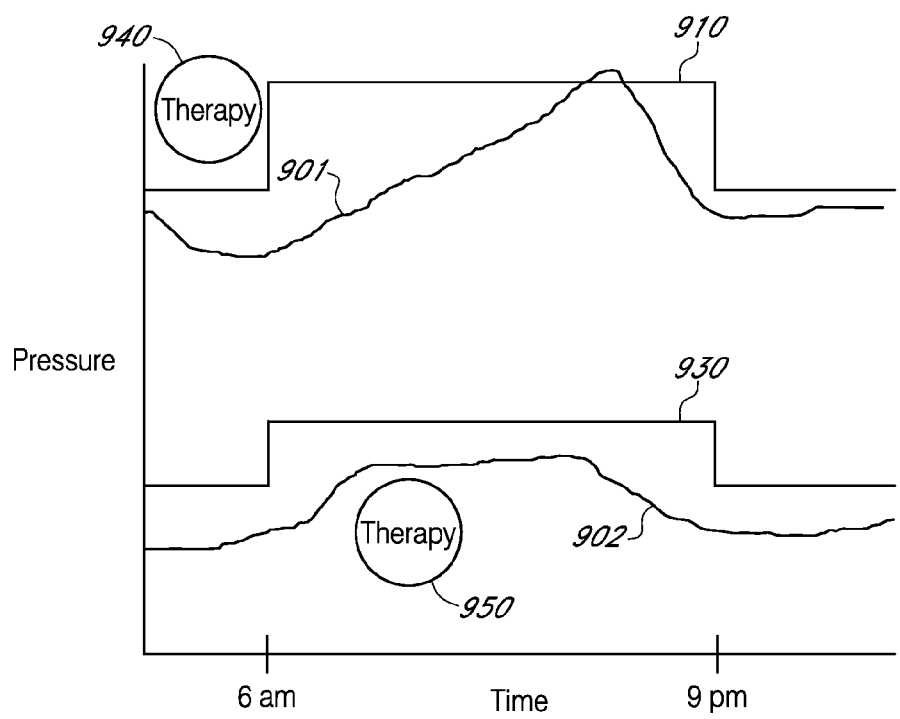
FIG. 24B illustrates the blood pressure of the patient of FIG. 24A after receiving therapy in accordance with the device and methods of the present invention.

In accordance with the present invention, and referring to FIGS. 24A and 24B, the following blood pressure results were achieved through use of the device and methods described herein. FIGS. 24A and 24B illustrate ambulatory blood pressure readings over a 24 hour period. Line 910 is the European Society of Hypertension (ESH), the UK National Institute for Health and Clinical Excellence (NICE) and American Society of Hypertension (ASH) recommended limits for Systolic blood pressure. Between the hours of 10 pm and 7 am a blood pressure of below 125 mmHg is considered to be at goal. During the daytime between the hours of 7 am and 10 pm, a blood pressure below 140 mmHg is considered to be at goal. Line 930 is the ESH, NICE and ASH recommended limits for Diastolic blood pressure, similar to the Systolic line 910, between the hours of 10 pm and 7 am an at-goal Diastolic pressure is considered to be 80 mmHg, and between the hours of 7 am to 10 pm a measurement of 90 mmHg is considered to be at goal.

As shown in FIG. 24A, lines 900 and 920 represent twenty-four (24) hour ambulatory blood pressure measurements of an individual, wherein blood pressure measurements were taken every fifteen (15) minutes. The user presented in FIG. 24B would be considered to be hypertensive, that is to have high blood pressure. This can be determined by looking specifically at lines 900 and lines 920, wherein any time these lines are above the recommend guideline pressures, lines 910 and 930 the user would be considered to be hypertensive.

Referring now to FIG. 24A there is shown a graph of the same user after having received therapy in accordance with the present invention. In this instance, the user received therapy at twice for two hours (2 hours) each time as depicted items 940 and 950. Comparing the user's actual blood pressure measurements, lines 900 and 920 of FIG. 24A, with the user's treated actual blood pressure measurements, lines 901 and 902 of FIG. 24A, it can be clearly seen that the user's blood pressure was significantly lowered through the application of therapy utilized the device and methods of the present invention.

To achieve the results depicted in FIG. 24A, two therapy providing devices were utilized, one on the left clavicle and one on the right clavicle. A frequency between 60 and 100 Hz was delivered by the speaker of each therapy providing device. The therapy providing devices were utilized for a total of 4 hours of therapy, wherein the frequency of 65 Hz was played for 8 seconds, followed by a sweep of frequencies from 65 Hz to 98 Hz lasting 1 second, afterwards 98 Hz was played for 8 seconds, followed by a sweep of frequencies from 98 Hz to 65 Hz lasting for 1 second. Therapy was provided, repeatedly for 120 minutes following this cycle. After 120 minutes the therapy was suspended for a period of 4 hours. After 4 hours of silence, an additional 120 minutes of therapy was delivered utilizing the cycle above.

Blood pressure measurements were taken before the application of the therapy, whereby the user's Systolic blood pressure averaged 131 mmHg at night time and 144 mmHg during the day. Diastolic blood pressure was 72 mmHg at night time and 87 mmHg during the day. After using the therapy for one evening (one 8 hour session as described above), Systolic blood pressure averaged 116 mmHg at nighttime and 131 mmHg at daytime and diastolic blood pressure averaged 66 mmHg at nighttime and 80 mmHg at daytime.

Method of Action

In accordance with the present invention, as described in detail above and with reference to the included publications, it is understood that baroreceptors and nerves affect blood pressure through a measured response generated by stretching or contraction of the arterial wall.

Nerve fibers, including baroreceptors, have the following input-output characteristics; threshold pressure, saturation, post-excitatory depression (PED), Asymmetric Rate Sensitivity and hysteresis.

As long as pressure within an artery remains below a certain level, no nerve firing occurs, this is referred to as the nerve threshold pressure. Above the threshold pressure, the fiber responds by producing action potentials, i.e., as signal. Individual fibers within humans and animals possess a wide range of pressure threshold values.

As pressure increases within the artery, the firing rate of individual fibers increases. However, at certain pressure, further increases in input yield no further increase in output frequency, thereby reaching the saturation of the baroreceptor nerve.

If pressure input within the artery is stepped from a low pressure, which is higher than the threshold pressure, to a higher pressure, then returning to a lower pressure level, will result in a brief period of shutoff, that is there will be no firing of the baroreceptor nerve, also referred to as post-excitatory depression (PED). The baroreceptor nerve will return to its original firing rate after time.

Baroreceptor nerve frequency response to rising pressure is more pronounced than the response to falling pressure, otherwise known as asymmetric rate sensitivity.

Lastly, periodic inputs produce looping in pressure-frequency plots, another indication of the asymmetry between responses to rising and falling pressures otherwise referred to as hysteresis.

In accordance with the present invention, utilization of the devices in accordance with the methods described herein cause an activation of the nervous system which affect blood pressure. The nerve terminal endings respond to stretch or acoustic vibration, and produce a frequency-modulated train of action potentials which can override the natural frequencies to elicit a response. Wherein the therapy provided by the invention, utilizes acoustic vibration of specific frequencies applied at specific time intervals to activate the body's nervous system to elicit a blood pressure response. The therapy of the present invention is applied in a cyclic manner as it is believed that the baroreceptors may become saturated if stimulated for too long of a period of time. If the therapy was applied continuously it is believed that the baroreceptors would stop responding.

According to a method of the present invention, the therapy providing device is disposed adjacent to a user's clavicle. The clavicle being a Dermal bone, is capable of transmitting vibrations. The clavicle lies above the cerviocoaxillary which holds auxiliary arteries, veins, airways and the brachial plexus of nerves that supply the upper limb of the arm. Vibrating the clavicle is believed to create micro-pulsations which travel to the Aortic Baroreceptors and the Carotid Bulb Baroreceptors. These micro-pulsations are believed to be perceived as an increase in heart rate by the baroreceptors which then send a signal to the brain. Thereby causing the body to lower blood pressure.

Selective stimulation of primary nerve endings can be obtained with careful control of the amplitude, displacement and the mode of application of the vibration or micro-pulsations.

What is claimed is:

1. A method of treating hypertension in a subject, the method comprising:
   applying vibratory energy with at least one speaker to at least one clavicle of the subject at a first vibration frequency; and
   applying vibratory energy with at least one speaker to the at least one clavicle at a second vibration frequency different from the first vibration frequency,
   the applying steps being performed for time periods sufficient to lower the subject's blood pressure.

2. The method of claim 1, wherein the first and second vibration frequencies are each between about 1 Hz and 20,000 Hz.

3. The method of claim 1, wherein the first and second vibration frequencies are each between 35 Hz and 150 Hz.

4. The method of claim 1, wherein the first and second vibratory energies are applied with first and second speakers, respectively.

5. The method of claim 1, wherein the first and second vibratory energies are applied with a first speaker to a right clavicle and to a left clavicle with a second speaker.

6. The method of claim 1, further comprising applying vibratory energy with the at least one speaker to the at least one clavicle at a plurality of vibration frequencies between the first vibration frequency and the second vibration frequency.

7. The method of claim 6, wherein the step of applying vibratory energy with the at least one speaker to the at least one clavicle at a plurality of vibration frequencies comprises stepping between the plurality of vibration frequencies.

8. The method of claim 6, wherein the step of applying vibratory energy with the at least one speaker to the at least one clavicle at a plurality of vibration frequencies comprises sweeping between the plurality of vibration frequencies.

9. The method of claim 1, further comprising, prior to the first applying step, placing the at least one speaker over at least one clavicle.

10. The method of claim 9, wherein the placing step comprises adhesively coupling the at least one speaker over at least one clavicle.

11. The method of claim 9, further comprising adhesively attaching a bandage to a skin surface over the at least one clavicle, the placing step comprising coupling the at least one speaker to the bandage.

12. The method of claim 11, wherein the attaching step comprises magnetically coupling the at least one speaker to the bandage.

13. The method of claim 1, wherein the applying steps comprises applying the first and second vibration frequencies in a cyclic manner sufficient to activate a baroreflex response.

14. A method of treating hypertension in a subject, the method comprising:

adhesively disposing at least one speaker over at least one clavicle of the subject; and using the at least one speaker to apply vibratory energy for a time period sufficient to lower the subject's blood pressure.

15. The method of claim 14, wherein the vibratory energy is applied at a vibration frequency of between 1 Hz and 20,000 Hz.

16. The method of claim 14, wherein the vibratory energy is applied at a vibration frequency of between 35 Hz and 150 Hz.

17. The method of claim 14, wherein the vibration frequency is a first vibration frequency, the method further comprising using the at least one speaker to apply vibratory energy to the at least one clavicle at a second vibration frequency different from the first vibration frequency.

18. The method of claim 17, comprising using the at least one speaker to apply the first and second vibration frequencies in a cyclic manner sufficient to activate a baroreflex response.

19. The method of claim 14, wherein the step of using the at least one speaker to apply vibratory energy comprises stepping between a plurality of vibration frequencies.

20. The method of claim 14, wherein the step of using the at least one speaker to apply vibratory energy comprises sweeping between a plurality of vibration frequencies.

* * * * *